(12) United States Patent
Bharmi et al.

(10) Patent No.: US 8,262,578 B1
(45) Date of Patent: Sep. 11, 2012

(54) SYSTEM AND METHOD FOR DETECTING PHYSIOLOGIC STATES BASED ON INTRACARDIAC ELECTROGRAM SIGNALS WHILE DISTINGUISHING CARDIAC RHYTHM TYPES

(75) Inventors: Rupinder Bharmi, Stevenson Ranch, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 1706 days.

(21) Appl. No.: 11/558,787

(22) Filed: Nov. 10, 2006

Related U.S. Application Data

(63) Continuation-in-part of application No. 11/416,317, filed on May 1, 2006, now Pat. No. 7,361,146, which is a continuation-in-part of application No. 11/127,389, filed on May 11, 2005, now abandoned.

(60) Provisional application No. 60/631,111, filed on Nov. 24, 2004.

(51) Int. Cl.
*A61B 5/08* (2006.01)
*A61B 5/02* (2006.01)
*A61B 5/04* (2006.01)

(52) U.S. Cl. ........ 600/484; 600/483; 600/500; 600/513; 600/510

(58) Field of Classification Search .................. 600/481, 600/483, 484, 529, 508, 509, 513, 515–518, 600/521

See application file for complete search history.

(56) References Cited

U.S. PATENT DOCUMENTS

| | | | |
|---|---|---|---|
| 4,089,959 A | 5/1978 | Diamond | |
| 4,757,815 A | 7/1988 | Strandberg et al. | |
| 5,056,519 A | 10/1991 | Vince | |
| 5,476,483 A | 12/1995 | Bornzin et al. | |
| 5,713,367 A * | 2/1998 | Arnold et al. ................. | 600/517 |
| 5,911,218 A | 6/1999 | DiMarco | |
| 6,128,534 A | 10/2000 | Park et al. | |
| 6,331,536 B1 | 12/2001 | Radulovacki et al. | |
| 6,415,183 B1 | 7/2002 | Scheiner et al. | |
| 6,432,956 B1 | 8/2002 | Dement et al. | |
| 6,449,509 B1 | 9/2002 | Park et al. | |
| 6,466,821 B1 | 10/2002 | Pianca et al. | |
| 6,480,733 B1 | 11/2002 | Turcott | |
| 6,512,952 B2 | 1/2003 | Stahmann et al. | |
| 6,519,493 B1 | 2/2003 | Florio et al. | |
| 6,525,073 B2 | 2/2003 | Mendel et al. | |

(Continued)

FOREIGN PATENT DOCUMENTS

EP 192971 B1 1/2005

(Continued)

OTHER PUBLICATIONS

J Allergy Clin Immunol. Nov. 1995; 96(5 Pt 2): 707-870.

(Continued)

*Primary Examiner* — Navin Natnithithadha

(57) ABSTRACT

Techniques are provided for tracking patient respiration or other physiologic states based upon intracardiac electrogram (IEGM) signals. In one example, respiration patterns are detected based upon cycle-to-cycle changes in morphological features associated with individual cardiac cycles while taking into account different cardiac rhythm types within the patient, such as predominantly paced or predominantly intrinsic rhythm types. Once respiration patterns have been identified, episodes of abnormal respiration, such as apnea, hyperpnea, nocturnal asthma, or the like, may be detected and therapy automatically delivered. In addition, techniques for detecting abnormal respiration using a pattern classifier are described, wherein the pattern classifier is trained while distinguishing the different cardiac rhythm types of the patient.

18 Claims, 33 Drawing Sheets

U.S. PATENT DOCUMENTS

| | | |
|---|---|---|
| 6,527,729 B1 | 3/2003 | Turcott |
| 6,586,478 B2 | 7/2003 | Ackman et al. |
| 6,600,949 B1 | 7/2003 | Turcott |
| 6,628,988 B2 | 9/2003 | Kramer et al. |
| 6,643,546 B2 | 11/2003 | Mathis et al. |
| 6,697,672 B2 | 2/2004 | Andersson |
| 6,731,985 B2 | 5/2004 | Poore et al. |
| 6,830,548 B2 | 12/2004 | Bonnet et al. |
| 6,942,622 B1 | 9/2005 | Turcott |
| 6,999,817 B2 | 2/2006 | Park et al. |
| 7,025,729 B2 | 4/2006 | de Chazal et al. |
| 7,130,681 B2 * | 10/2006 | Gebhardt et al. ............... 607/6 |
| 7,177,686 B1 | 2/2007 | Turcott |
| 7,184,817 B2 | 2/2007 | Zhu et al. |
| 7,206,636 B1 | 4/2007 | Turcott |
| 7,361,146 B1 * | 4/2008 | Bharmi et al. ............... 600/484 |
| 7,435,221 B1 * | 10/2008 | Bharmi et al. ............... 600/484 |
| 7,610,094 B2 * | 10/2009 | Stahmann et al. ............ 607/42 |
| 7,787,946 B2 * | 8/2010 | Stahmann et al. ............ 607/3 |
| 7,869,878 B1 * | 1/2011 | Koh ............................... 607/20 |
| 2003/0216789 A1 | 11/2003 | Deem |
| 2004/0134496 A1 | 7/2004 | Cho et al. |
| 2006/0184056 A1 | 8/2006 | de Chazal et al. |

FOREIGN PATENT DOCUMENTS

WO      WO2004/062484 A2     7/2004

OTHER PUBLICATIONS

NonFinal Office Action, mailed Sep. 6, 2007: Related U.S. Appl. No. 11/127,389.

NonFinal Office Action, mailed Aug. 23, 2007: Related U.S. Appl. No. 11/416,317.

NonFinal Office Action, mailed Sep. 6, 2007: Related U.S. Appl. No. 11/558,819.

Ayas, Najib T., et al.; A Prospective Study of Self-Reported Sleep Duration and Incident Diabetes in Women; Diabetes Care, 26:380-384, 2003.

de Chazal, Philip, et al.; Automated Processing of the Single-Lead Electrocardiogram for the Detection of Obstructive Sleep Apnoea; IEEE Transactions on Biomedical Engineering, vol. 50, No. 6, Jun. 2003.

Fichter, Joachim, et al.; Sleep-Related Breathing Disorders Are Associated With Ventricular Arrhythmias in Patients With an Implantable Cardioverter-Defibrillator; Chest 2002; 122:558-561.

Fietze, Ingo, et al.; Sleep Apnea Syndrome in Patients with Cardiac Pacemaker; Respiration 2000; 67:268-271.

Gottlieb, Daniel J., et al.; Association of Sleep Time With Diabetes Mellitus and Impaired Glucose Tolerance; Arch Intern Med/vol. 165, Apr 25, 2005.

Haskell, Joan; Practice Parameters for the Diagnosis and Treatment of Asthma; The Journal of Allerby, and clinical Immunology. vol. 96, No. 5, part 2. Nov. 1995.

Jones, Alice Y.M., et al.; Body Position Change and its effect on hemodynamic and metabolic status; Heart & Lung, vol. 33, No. 5, Sep./Oct. 2004.

Meslier, N., et al.; Impaired glucose-insulin metabolism in males with obstructive sleep apnoea syndrome; Eur Respir J 2003; 22: 156-160.

Moody, George B., et al.; Clinical Validatian of the ECG-Derived Respiration (EDR) Technique; Computers in Cardiology 1986, vol. 13, pp. 507-510.

Redmond, Stephen J., et al.; Cardiorespiratory-Based Sleep Staging in Subjects with Obstructive Sleep Apnea; IEEE Transactions on Biomedical Engineering, vol. 53, No. 3, Mar. 2006.

Sarai, R. Bharmi, et al.; Post depolarization integral based detection of breathing patterns using paced intracardiac electrograms; Europace Supplements, vol. 7, Jun. 2005.

Spiegel, Karine, et al.; Impact of sleep debt on metabolic and endocrine function; The Lancet, vol. 354, Oct. 23, 1999.

Stein, Duntley S., et al.; Sleep Apnea Monitoring Using Sleep Disordered Heat Rate in an Implanted Device; Sleep 2005;28 (suppl.);A326.

Yasuma, Fumihiko, et al.; Respiratory Sinus Arrhythmia—Why Does the Heartbeat Synchronize With Respiratory Rhythm?; Chest, 125, Feb. 2, 2004.

Yeragani VK, et al.; Effect of posture and isoproterenol on beat-to-beat heart rate and QT variability; Neuropsychobiology. 2000;41(3):113-23.

* cited by examiner

SYSTEM AND METHOD FOR DETECTING PHYSIOLOGIC STATES BASED ON INTRACARDIAC ELECTROGRAM SIGNALS WHILE DISTINGUISHING CARDIAC RHYTHM TYPES

CROSS REFERENCES TO RELATED APPLICATIONS

This application is a continuation-in-part (CIP) of U.S. patent application Ser. No. 11/416,317, filed May 1, 2006, entitled "System And Method For Detecting Abnormal Respiration Via Respiratory Parameters Derived From Intracardiac Electrogram Signals", which was a CIP of U.S. patent application Ser. No. 11/127,389, filed May 11, 2005, entitled "System and Method for Detection of Respiration Patterns via Intracardiac Electrogram Signals", which claimed the benefit of U.S. Provisional Patent Application Ser. No. 60/631,111, filed Nov. 24, 2004. This application is also related to co-pending U.S. patent application Ser. No. 11/558,819, filed contemporaneously herewith, entitled "System and Method for Detecting Abnormal Respiration based on Intracardiac Electrogram Signals using a Pattern Recognition Device" (A06P1126). Each of these applications is incorporated by reference herein.

FIELD OF THE INVENTION

The invention generally relates to implantable medical devices, such as pacemakers or implantable cardioverter/defibrillators (ICDs), and in particular, to techniques for detecting respiration or other physiologic states within a patient in which a medical device is implanted, including abnormal respiration states such as apnea, hypopnea or nocturnal asthma.

BACKGROUND OF THE INVENTION

It is highly desirable to reliably track respiration within patients having pacemakers and ICDs. Tracking patient respiration permits potentially dangerous respiratory disorders, such as apnea, hypopnea, hyperpnea, nocturnal asthma, and Cheyne-Stokes Respiration (CSR), to be detected. Apnea and hypopnea are abnormal respiration patterns characterized by periods of significantly reduced respiration. With hypopnea, respiration is reduced but still present. With apnea, however, respiration may cease completely for 10 seconds or longer. One common form of apnea is sleep apnea, in which hundreds of individual episodes of apnea can occur during a single night. Accordingly, patients with sleep apnea experience frequent wakefulness at night and excessive sleepiness during the day. In addition, apnea can exacerbate various medical conditions, particularly hypertension. Apnea can also exacerbate congestive heart failure (CHF), a condition wherein the patient suffers from poor cardiac function. Indeed, the aberrant blood chemistry levels occurring during sleep apnea are a significant problem for patients with CHF. Due to poor cardiac function caused by CHF, patients already suffer from generally low blood oxygen levels. Frequent periods of sleep apnea result in even lower blood oxygen levels.

Episodes of apnea can also occur during CSR, which is an abnormal respiratory pattern often occurring in patients with CHF. CSR is characterized by alternating periods of hypopnea and hyperpnea (i.e. fast, deep breathing.) Briefly, CSR arises principally due to a time lag between blood $CO_2$ levels sensed by the respiratory control nerve centers of the brain and the blood $CO_2$ levels. With CHF, poor cardiac function results in poor blood flow to the brain such that respiratory control nerve centers respond to blood $CO_2$ levels that are no longer properly representative of the overall blood $CO_2$ levels in the body. Hence, the respiratory control nerve centers trigger an increase in the depth and frequency of breathing in an attempt to compensate for perceived high blood $CO_2$ levels—although the blood $CO_2$ levels have already dropped. By the time the respiratory control nerve centers detect the drop in blood $CO_2$ levels and act to slow respiration, the blood $CO_2$ levels have already increased. This cycle becomes increasingly unbalanced until respiration alternates between hypopnea and hyperpnea. The periods of hypopnea often become sufficiently severe that no breathing occurs between the periods of hyperpnea, i.e. periods of frank apnea occur between the periods of hyperpnea. The wildly fluctuating blood chemistry levels caused by alternating between hyperpnea and apnea/hypopnea can significantly exacerbate CHF and other medical conditions. When CHF is still mild, CSR usually occurs, if at all, only while the patient is sleeping. When it becomes more severe, CSR can occur while the patient is awake.

Abnormal respiration during sleep may also arise due to nocturnal asthma. With asthma, the linings of the airways swell and become more inflamed. Mucus clogs the airways and the muscles around the airways tighten and narrow. Hence, breathing becomes difficult and stressful. During an asthma attack, rapid breathing patterns similar to hyperpnea occur, though little or no oxygen actual reaches the lungs. An asthma attack may be triggered by allergens, respiratory infections, cold and dry air, or even heartburn. The majority of asthma attacks occur during the night, between 3:00 a.m. and 5:00 a.m. Nocturnal asthma has been associated with factors such as decreased pulmonary function, hypoxemia and circadian variations of histamine, epinephrine, and cortisol concentrations. Asthma attacks at night may also be triggered directly by sleep apnea. Nocturnal asthma attacks may be fatal, particularly within patients also suffering from CHF.

In view of the significant adverse consequences of apnea/hypopnea, nocturnal asthma, or CSR, particularly insofar as patients with CHF are concerned, it is highly desirable to provide techniques for detecting such conditions. Tracking actual patient respiration provides perhaps the most direct and effective technique for detecting respiratory disorders. For patients with pacemakers and ICDs, respiration is conventionally tracked based on thoracic impedance as measured via pacing/sensing leads implanted within the heart. Sensing of the intracardiac electrogram (IEGM) of the patient is temporarily suspended during each cardiac cycle so as to sense an impedance signal, from which respiration patterns are derived. See, for example, U.S. Pat. No. 6,449,509 to Park, et al., entitled "Implantable Stimulation Device Having Synchronous Sampling for a Respiration Sensor."

Although impedance-based techniques are useful, it would be desirable to provide alternative techniques for tracking respiration, particularly for the purposes of detecting episodes of abnormal respiration, wherein respiration is derived solely from the IEGM signal so as to eliminate the need to detect or process impedance. Additionally, this eliminates need for additional sensors, and the sensing electrodes can be thus used for IEGM based breathing pattern detection and hence, the ease of implementability in current platforms. One technique for deriving respiration from an IEGM signal is set forth in U.S. Pat. No. 6,697,672 to Andersson, entitled "Implantable Heart Stimulator", which is incorporated by reference herein. Briefly, Andersson provides a technique to extract parameters related to patient respiration from an analysis of intervals between various events detected within a ventricular-IEGM (i.e. V-IEGM) signal. For example, cycle-to-cycle variability is tracked in R-R intervals or in the amplitude of S-T intervals. In other words, the technique of Andersson exploits interval-based morphological features of the V-IEGM to track respiration. Although not discussed in the Andersson reference, autonomic variability arising during respiration causes the interval-based changes in the IEGM. R-waves (also referred to as QRS-complexes) are electrical signals representative of the depolarization of ventricular muscle tissue. The subsequent electrical repolarization of the ventricular tissue appears within the IEGM as a T-wave. Electrical depolarization of atrial muscle tissue is manifest as a P-wave. Strictly speaking, P-waves, R-waves and T-waves are features of a surface electrocardiogram (EKG or ECG). For convenience, the terms P-wave, R-wave and T-wave are also used herein (and in the literature) to refer to the corresponding internal signal component.

Although the interval-based variability technique of Andersson is effective, it is desirable to provide additional or alternative IEGM-based techniques for trending and tracking respiration and for detecting episodes of abnormal respiration. This general goal was achieved by the techniques of patent application Ser. No. 11/127,389, cited above. Briefly, respiration patterns are detected based upon cycle-to-cycle changes in morphological features associated with individual electrical events with the IEGM signals. For example, slight changes in the peak amplitudes of QRS-complexes, P-waves or T-waves are tracked to identify cyclical variations representative of patient respiration. Alternatively, the integrals of the morphological features of the individual events may be calculated for use in tracking respiration. Once respiration patterns have been identified, episodes of abnormal respiration, such as apnea, hyperpnea, nocturnal asthma, or the like, may be detected and therapy automatically delivered.

Hence, the techniques of patent application Ser. No. 11/127,389, which are also described herein below, are not limited to analyzing interval-based features of a V-IEGM, as with certain predecessor techniques. Instead, the techniques of the parent application examine changes within individual features of cardiac cycles over time. In this regard, it has been observed that respiration causes slight variations in the size and shape of individual electrical events of the IEGM signals, such as QRS-complexes, and that those changes are correlated with respiration. This differs from changes in intervals (such as R-R intervals), which, as noted, appear to arise due to autonomic variability. In one specific example, changes in the integrals of the QRS-complex derived from a V-IEGM channel signal are examined, alone or in combination with, integrals of P-waves derived from an atrial IEGM (A-IEGM) channel signal. Interval-based parameters, such as variations in A-A, R-R or AV intervals, may be additionally used to aid in tracking respiration but are not required. That predecessor application also presented techniques for detecting episodes of abnormal respiration based on respiration patterns derived from IEGMs, such as episodes of such as apnea, hypopnea, nocturnal asthma, or CSR.

Patent application Ser. No. 11/416,317 provided further improvements in the area of abnormal respiration detection based on IEGM signals. These improvements, which are also described herein below, are particularly directed to exploiting respiratory parameters such as inter-breath interval, respiration depth, and respiration power in the detection of abnormal respiration, with each of the respiratory parameters conveniently derived from IEGM signals. These techniques are particularly well suited to detecting episodes of abnormal respiration during sleep. In this regard, normal respiration during sleep is characterized by an almost constant respiration depth (corrected for patient posture and other non-respiratory factors). Hence, significant changes in respiration depth or other parameters associated with the respiratory cycles are indicative of a transition from normal respiration to some form of abnormal respiration. Further analysis of the respiratory parameters is used to identify the particular form of abnormal respiration. The technique can also be used to track and trend sleep disorder breathing or, in general, disordered breathing. Depending upon the capabilities of the implanted device, appropriate therapy may then be delivered. For example, an alarm device may be triggered to alert the patient upon detection of an episode of apnea/hypopnea. The alarm device may be, e.g., an implanted device such as a "tickle" voltage warning device or a bedside warning system that emits an audible alarm. In this manner, if the patient is asleep, the patient is thereby awakened so as to prevent extended episodes of apnea/hypopnea from occurring, which can cause significant variances in blood chemistry that can exacerbate other medical conditions such as CHF.

Although the techniques of the predecessor applications cited above are quite useful, room for still further improvement remains. In particular, it has been found by the present inventors that improvements in tracking respiration and in discriminating normal respiration from abnormal respiration can be achieved by taking into account the predominant cardiac rhythm type of the patient. That is, some patients have a cardiac rhythm that is predominantly paced; whereas other patients have a cardiac rhythm that is predominantly intrinsic (i.e. the patient's heart beats mostly on its own.) Also, it has been found that the use of pattern classifiers (such as pattern classifiers of the type described in U.S. Pat. No. 7,025,729 to de Chazal, et al., entitled "Apparatus for Detecting Sleep Apnea using Electrocardiogram Signals") are helpful in discriminating normal respiration from abnormal respiration. Accordingly, various aspects of the present invention are directed to distinguishing cardiac rhythm types during respiration detection and during the discrimination of normal respiration from abnormal respiration. Further aspects of the invention are directed to distinguishing cardiac rhythm types during the training of an abnormal respiration pattern classifier and during its subsequent use. Still other aspects of the invention are directed to more broadly exploiting cardiac rhythm types in the detection of other physiologic states besides respiration.

SUMMARY

In one embodiment, a method is provided for detecting physiologic states within a patient using an implantable medical device while distinguishing among different cardiac rhythm types. To this end, the predominant cardiac rhythm type of the patient is initially determined. In one example, following implant, the device determines whether the heartbeats of the patient are predominantly paced or are instead predominantly intrinsic. In other examples, the device further distinguishes among four different cardiac rhythms: AR (paced atrial beats/intrinsic ventricular beats); AV (paced atrial beats/paced ventricular beats); PR (intrinsic atrial beats/intrinsic ventricular beats); and PV (intrinsic atrial beats/paced ventricular beats). That is, the device determines which of the four basic cardiac rhythm types is predominant. This determination can be periodically updated so as to account for any changes within the patient occurring due to, e.g., disease progression, medications usage, ischemic attacks, changes in device programming, etc. In one particular example, the physiologic state to be detected is respiration. To actually detect patient respiration, the device senses cardiac electrical signals and identifies individual cardiac cycles (i.e. heartbeats) therein. The device also determines whether or not the individual cardiac cycles correspond to the predominant rhythm type. The device then detects patient respiration based on cycle-to-cycle changes in morphological parameters associated with the individual cardiac cycles while distinguishing between cardiac cycles of the predominant rhythm type and cardiac cycles of other rhythm types. Other physiologic states that may be detected, tracked and discriminated include apnea, hypopnea, hyperpnea, asthma, CSR, hypoglycemia, hyperglycemia, diabetes, renal failure, hypertension, ischemia, hyperkalemia, hypokalemia, obesity, stroke, chronic obstructive pulmonary disease (COPD), pulmonary edema, edema, anemia, heart failure, exertion induced dyspnea, and tachypnea with hypoglycemia. That is, the implantable device is equipped to detect a variety of cardiac disease comorbidities.

By distinguishing cardiac cycles based on rhythm type, the device can more accurately detect patient respiration or other physiologic states. In this regard, the cycle-to-cycle changes in morphological parameters of the cardiac cycles caused by respiration may differ depending upon the rhythm type of the cardiac cycles. That is, cyclical variations in the parameters extracted from paced beats may differ from cyclical variations in parameters extracted from intrinsic beats. In one particular example, the device tracks respiration based only on cardiac cycles of the predominant rhythm type while ignoring all other cardiac cycles. This is particularly effective if almost all cardiac cycles are of the predominant type with relatively few other cardiac cycles (such as may occur if the patient is subject to continuous overdrive pacing.) In another particular example, the device instead uses all cardiac cycles to track respiration but processes the cycles of different rhythm types separately, such as by using one or more pattern classifiers that have been separately trained. Detection of respiration using these techniques may potentially be employed for any of a variety of purposes by the implanted device. However, the techniques are particularly well suited for use in detecting episodes of abnormal respiration, such as apnea, CSR, and the like.

In a first illustrative abnormal respiration detection embodiment, the device preprocesses cardiac cycles based on cardiac rhythm type before attempting to discriminate between normal and abnormal respiration. Upon activation, the abnormal respiration detector inputs an indictor from memory specifying the predominant cardiac rhythm type within the patient, AR, AV, PR or PV, which has already been ascertained. The abnormal respiration detector then begins tracking individual cardiac cycles while identifying the rhythm type of each cardiac cycle, i.e. AR, AV, PR or PV. For any cardiac cycles that are not of the predominant type, i.e. for any secondary-type cycles, the abnormal respiration detector then determines whether the secondary cycle is "spurious". A spurious cycle is a single cycle not part of a sequence of other like cycles, such as a single AV beat amid a sequence of PR beats. Any spurious cycles of secondary rhythm types are ignored for the purposes of abnormal respiration detection. Non-spurious secondary cycles (i.e. secondary cycles that appear as couplets or runs of cycles) are retained for abnormal respiration detection. However, these cycles are renormalized.

Then, the abnormal respiration detector determines whether the patient is undergoing an episode of abnormal respiration based on an analysis of all cardiac cycles of the predominant rhythm type as well as any renormalized cardiac cycles of secondary rhythm types. The analysis may exploit, for example, inter-breath intervals, respiration depth, and respiration power. In other examples, the analysis uses a linear discriminant pattern classifier or other device that has been trained to discriminate normal respiration from abnormal respiration. If so, the pattern classifier is preferably trained to recognize abnormal respiration by employing cardiac cycles that have been pre-processed in the same manner, i.e. by detecting and then ignoring spurious cycles. Whenever abnormal respiration is detected, the implanted device might generate warning signals and/or deliver appropriate therapy. In other examples, the implanted device simply records diagnostic data for subsequent physician review.

In a second illustrative abnormal respiration detection embodiment, the device uses a pattern classifier or other device that has been trained to ignore any cardiac cycles not of the predominant type. Training is performed prior to device implant by inputting morphological parameters derived from numerous patient IEGMs to the pattern classifier while also inputting an indication of whether each of the particular IEGMs was obtained while the corresponding patient was undergoing normal or abnormal respiration. An external system is used to detect abnormal respiration within test patients for use in training the pattern classifier of the implanted device. Once the pattern classifier has been trained using the predominant cardiac cycles (and tested to verify that it can accurately and reliably detect abnormal respiration), it is installed within implantable devices such as pacemakers for use within patients.

Thereafter, the pattern classifier discriminates between normal and abnormal respiration based on predominant cardiac cycles. That is, any cycle of a secondary type is discarded for the purposes of abnormal respiration detection. Also, preferably, the device detects and ignores preatrial contractions (PACs), preventricular contractions (PVCs), and any cardiac cycles arising during atrial bigeminy that transitions to atrial fibrillation (AF), at least for the purposes of abnormal respiration detection. The device also ignores the first cycle immediately following any PAC or PVC, as the morphology of these beats may be affected by the preceding PAC or PVC. Furthermore, the abnormal respiration detector is preferably deactivated during ventricular bigeminy/trigeminy, atrial tachycardia (AT) and/or AF and following any mode switch to a nontracking mode. Assuming that an episode of abnormal respiration is detected by the pattern classifier, the abnormal respiration detector also preferably evaluates the severity of the episode so that appropriate therapy, warnings and diagnostics can be generated.

Thus, by taking into account cardiac rhythm types, improvements in the detection and discrimination of various physiologic states can be achieved. These improvements are preferably implemented within implantable medical devices to permit the device to detect abnormal physiologic states and respond promptly. However, principles of the invention are also applicable to external devices when used in conjunction with implanted devices. For example, an external programmer device may be equipped to detect abnormal physiologic states within a patient based on IEGM data sensed by a device implanted within the patient and sent via telemetry to the programmer for processing.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
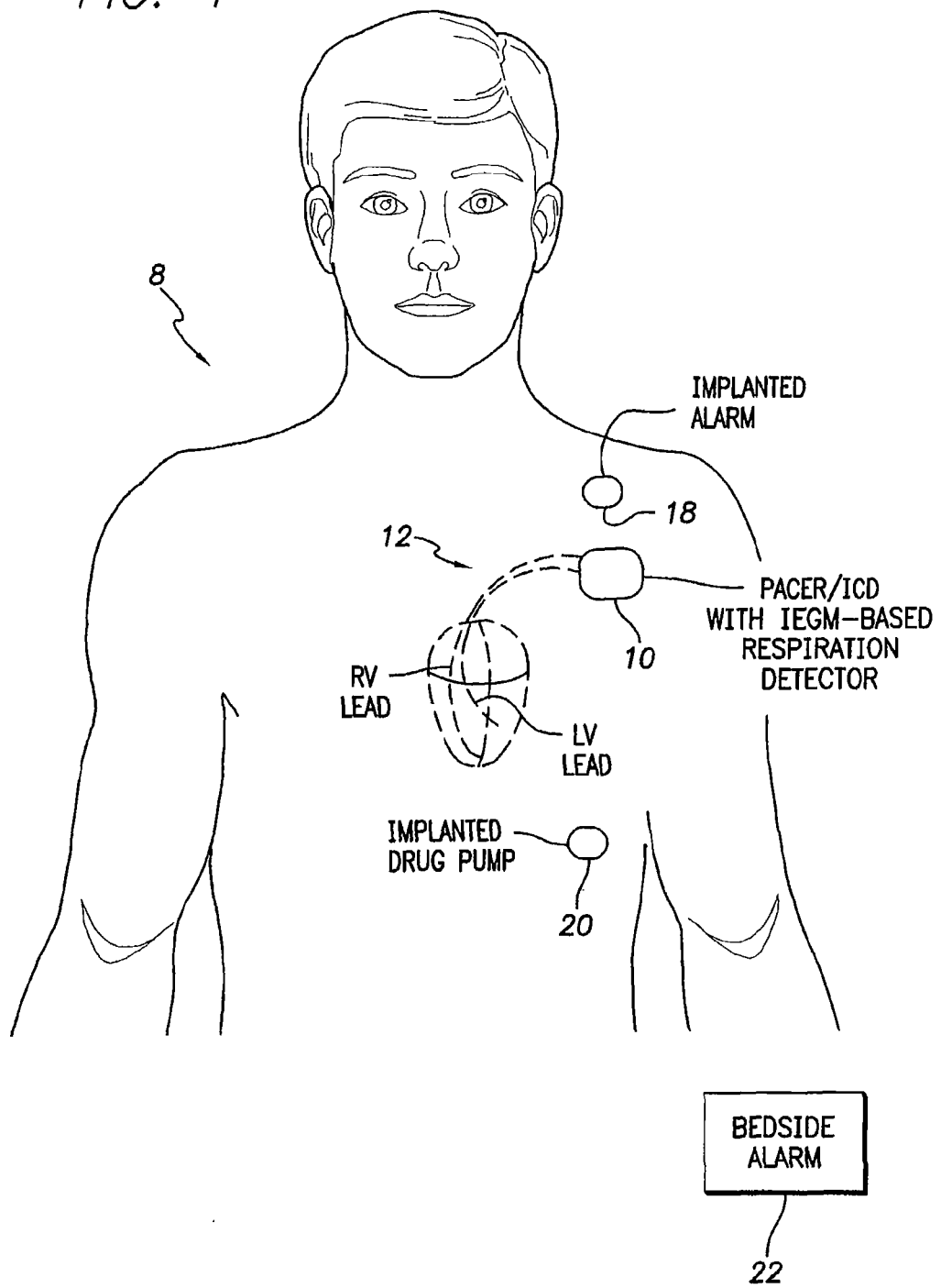
FIG. 1 illustrates pertinent components of an implantable medical system having a pacer/ICD capable of: tracking respiration patterns based on IEGM signals detected via leads mounted in the heart; detecting episodes of abnormal respiration based on the respiration patterns; and delivering therapy or warning signals in response thereto.
Figure 16:
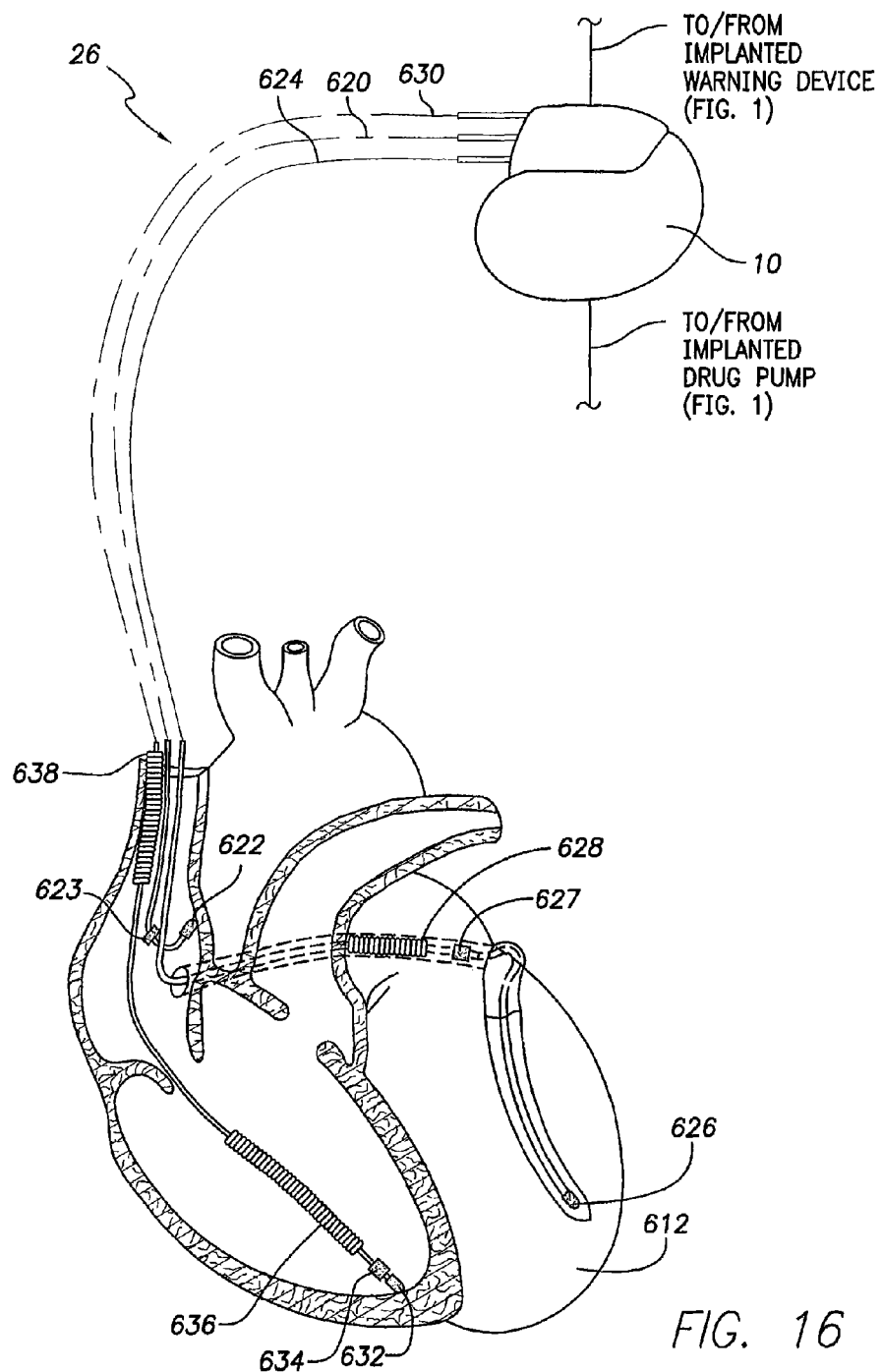
FIG. 16 is a simplified, partly cutaway view, illustrating the pacer/ICD of FIG. 1 along with a complete set of leads implanted in the heart of a patient.

FIG. 1 illustrates an implantable medical system 8 having a pacer/ICD capable of tracking respiration based on IEGM signals, identifying episodes of abnormal respiration and delivering appropriate therapy. To this end, pacer/ICD 10 receives voltage signals from various cardiac pacing leads (only two of which are shown in the FIG. 1) from which various channels of IEGM signals are derived including, for example, unipolar or bipolar A-IEGM signals and unipolar or bipolar V-IEGM signals. A complete set of exemplary pacing leads are shown in FIG. 16 from which a wide variety of specific channels of IEGM signals may be derived. Based on the IEGM signals, the pacer/ICD detects parameters associated with patient respiration using a technique broadly summarized below with reference to FIG. 2. Examples that are more specific are set forth in FIGS. 3-13. Based on the respiration parameters, the pacer/ICD then also detects individual episodes of abnormal respiration, such as apnea, asthma or CSR.

Once an episode of abnormal respiration has been detected, the pacer/ICD uses additional implanted components (if so equipped) to deliver appropriate therapy or warning signals. For example, if apnea/hypopnea is detected, the pacer/ICD may activate an internal alarm 18 or an external bedside alarm 22. Internal alarm 18 may be a vibrating device or a "tickle" voltage device that, in either case, provides perceptible stimulation to the patient to alert or awaken the patient so as to terminate the episode of apnea/hypopnea. The bedside alarm may provide audible or visual alarm signals of sufficient magnitude to alert or awaken the patient. If an activity sensor is provided within the pacer/ICD, the form of the alarm may be controlled based on patient activity. For example, if the activity level indicates that the patient is asleep, a more noticeable alarm may be employed than if the patient is deemed to be awake. In addition, while the patient is asleep, the intensity of the alarm signal can be periodically increased until the patient awakens, as detected by the activity sensor. Additionally, or in the alternative, the system may include a drug pump 20 capable of the delivering medications in an attempt to prevent the onset of additional episodes of apnea/hypopnea. Discussions of exemplary medications are provided below. In addition, the pacer/ICD may deliver atrial overdrive pacing for the purposes of preventing additional episodes of apnea/hypopnea from occurring.

Thus, FIG. 1 provides an overview of an implantable system for tracking respiration, detecting episodes of abnormal respiration and for delivering therapy in response thereto. Although a pacer/ICD is illustrated in FIG. 1, it should be understood that the detection techniques of the invention may be implemented within other implantable devices, including dedicated respiration detection devices not necessarily capable of providing cardiac stimulation therapy. Note also that internal signal transmission lines for interconnecting the various implanted components are not shown. Alternatively, wireless signal transmission may be employed. In addition, it should be appreciated that systems provided in accordance with invention need not include all the components shown in FIG. 1. In many cases, for example, the system will include only the pacer/ICD and its leads. Other implementations will employ internal or external alarms but no drug pumps. These are just a few exemplary embodiments. No attempt is made herein to describe all possible combinations of components that may be provided in accordance with the general principles of the invention. Also, note that the particular locations of the implanted components are merely exemplary.

Overview of Technique for Tracking Respiration Using IEGM

Figure 2:
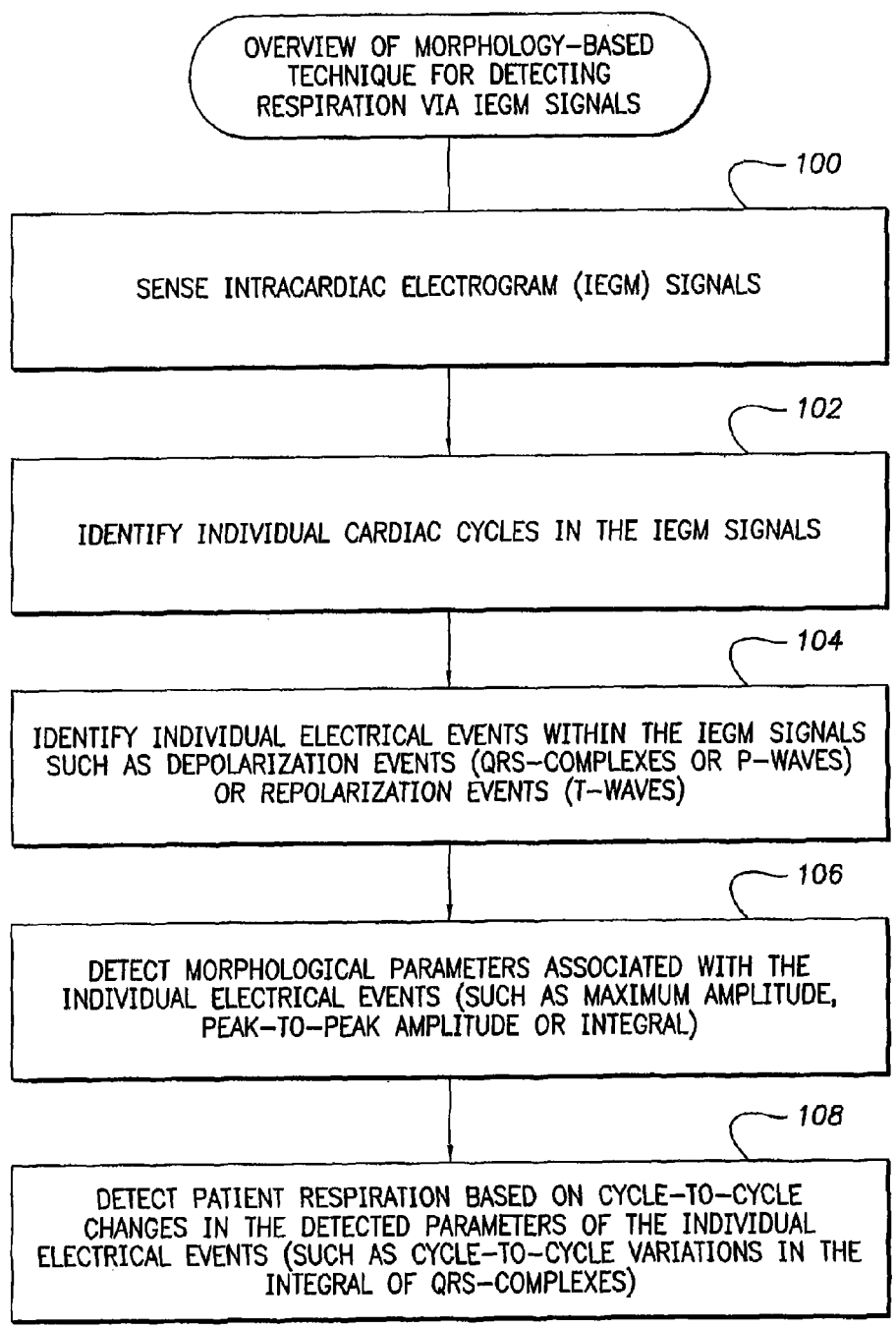
FIG. 2 is a flow chart providing an overview of the method for tracking respiration patterns based on IEGM signals, which may be performed by the system of FIG. 1.
Figure 3:
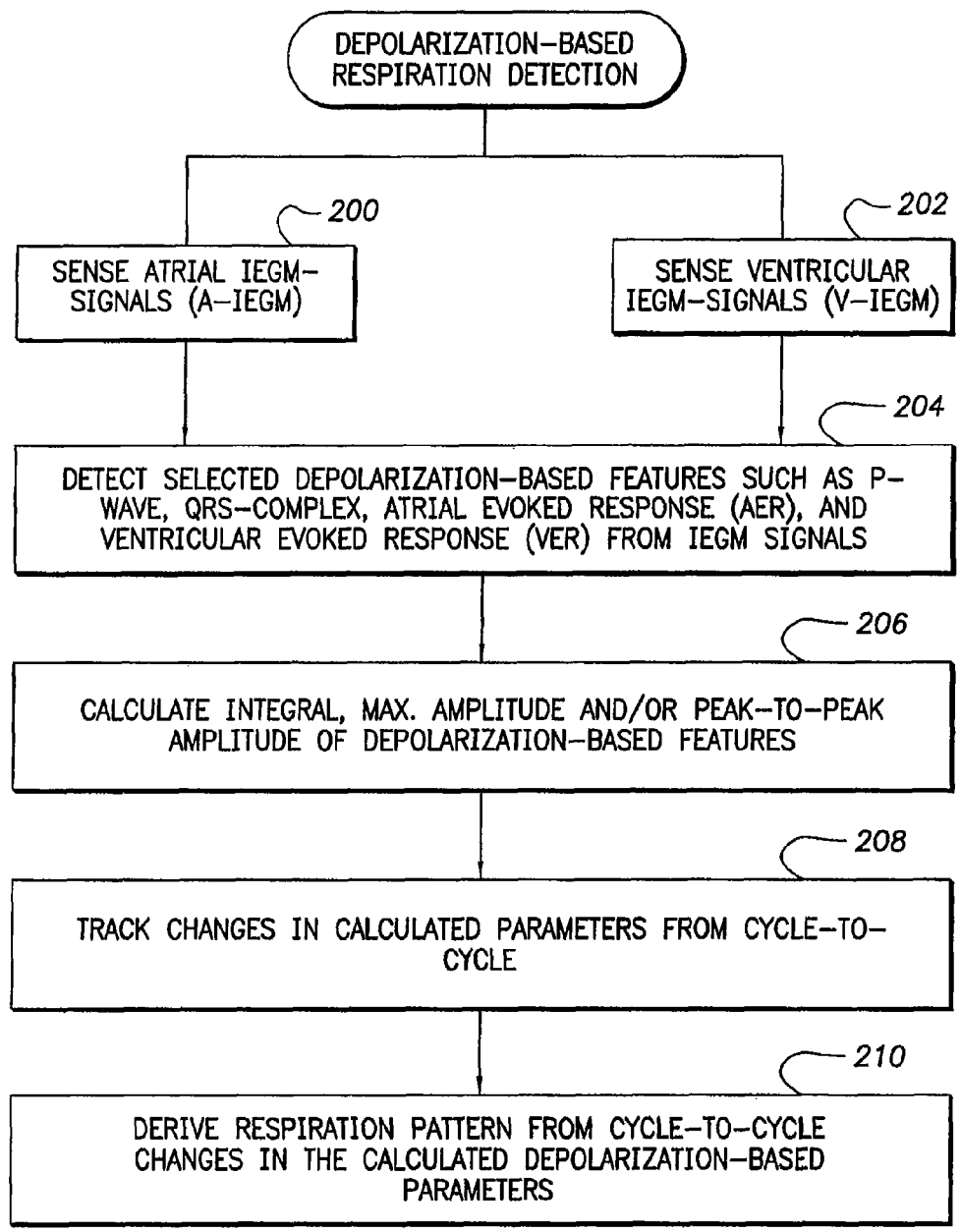
FIG. 3 is a flow chart specifically illustrating depolarization-based respiration detection techniques, which may be performed by the system of FIG. 1.

FIG. 2 provides an overview of the techniques of the invention for tracking respiration patterns via morphological features of IEGM signals. Initially, at step 100, IEGM signals are sensed by an implantable medical device, such as the pacer/ICD of FIG. 1. As will be explained in greater detail with reference to the specific examples below, the IEGM signals may be atrial channel signals, ventricular channel signals, cross chamber signals, or some combination thereof. In any case, at step 102, individual cardiac cycles are identified within the IEGM signals using otherwise conventional detection techniques, which typically operate to detect cardiac cycles based on QRS-complexes. At step 104, selected electrical events are identified within the IEGM signals, such as depolarization events (e.g. QRS-complexes or P-waves) or repolarization events (i.e. T-waves). At step 106, morphological parameters associated with the individual events are detected—such as the maximum amplitude of the event, the peak-to-peak amplitude of the event, or the numerical integral of the event (i.e. the total energy associated with the event). As will be explained, multiple parameters may be detected for each individual event (e.g. both the maximum amplitude and integral of an event may be detected) and different parameters may be detected for different events (e.g. the peak-to-peak amplitude may be determined for P-waves whereas an integral may be calculated for T-waves.)

Then, at step 108, patient respiration is detected based on cycle-to-cycle changes in the morphological parameters (such as cycle-to-cycle variations in the integral of the QRS-complexes or cycle-to-cycle changes in the maximum amplitudes of P-waves). In other words, changes in morphology of a given parameter from one beat to another are tracked for the purposes of detecting respiration patterns. This differs from changes in intervals (such as R-R intervals), which, as noted above, appear to arise due to autonomic variability.

The slight variations in the morphology of individual events within the IEGM are tracked from cycle-to-cycle so as to detect the cyclical changes associated with normal respiration. Otherwise conventional filters may be used to isolate cyclical patterns appearing at frequencies associated with respiration. Additionally, an analysis of changes in the intervals between beats may be used to enhance the reliability of the respiration detection technique of step 108. In particular, the techniques described in the above-referenced patent to Andersson may be employed. Variability in AV or A-A intervals may also be employed. In other words, both interval-based and individual feature-based techniques may be employed to enhance detection specificity.

Depolarization-Based Respiration Detection Examples

Turning now to the FIGS. 3-7, examples of the technique specifically directed to the use of depolarization-based parameters (i.e. P-waves and QRS-complexes) will now be described. Beginning at steps 200 and 202, the pacer/ICD (or other implanted medical device) senses A-IEGM and V-IEGM channel signals. The signals may be derived from a lead configuration that may be unipolar, bipolar or cross-chamber (i.e. signals sensed between electrodes is separate chambers such as between A-tip to V-tip.) The specific channel used may be right atrium, right/left Ventricle. Far field QRS or T-waves can be analyzed in the atrial channel i.e. far-field R-waves and ventricular repolarization (T-waves). Additionally, the Ventricular channel near-field QRS and T-waves can be used. In any case, at step 204, selected depolarization-based features are detected within the IEGM signals. Examples include P-waves, QRS-complexes, atrial evoked responses (AERs) and ventricular evoked responses (VERs). Different features may be detected within different IEGM channel signals. For example, P-waves and AERs may be detected within A-IEGM channel signals; whereas QRS-complexes and VERs may be detected within V-IEGM channel signals. At step 206, the pacer/ICD calculates the numerical integral, the maximum amplitude and/or the peak-to-peak amplitude of the detected features or other suitable morphological parameters. Maximum or peak amplitude of an event represents the maximum of the absolute value of the respective IEGM channel signal during the event. Peak-to-peak amplitude instead represents the difference between the highest and lowest values of the respective IEGM channel signal during the event. With a baseline voltage of zero, the peak-to-peak amplitude thereby represents the difference between the largest positive and largest negative values of the IEGM signal during the event. Insofar as integrals of paced events are concerned, a paced depolarization integral (PDI) is preferably calculated. Otherwise conventional techniques for calculating PDIs may be employed. See, for example, U.S. Pat. No. 6,731,985 to Poore, et al., entitled "Implantable Cardiac Stimulation System and Method for Automatic Capture Verification Calibration.") For paced beats, the PDI is more useful than QRS amplitude because the PDI provides an improved signal-to-noise ratio. In any case, at step 208, the pacer/ICD tracks changes in the calculated parameters from cycle-to-cycle (typically over at least a few dozen cardiac cycles) and, at step 210, derives respiration parameters from those changes.

Figure 4:
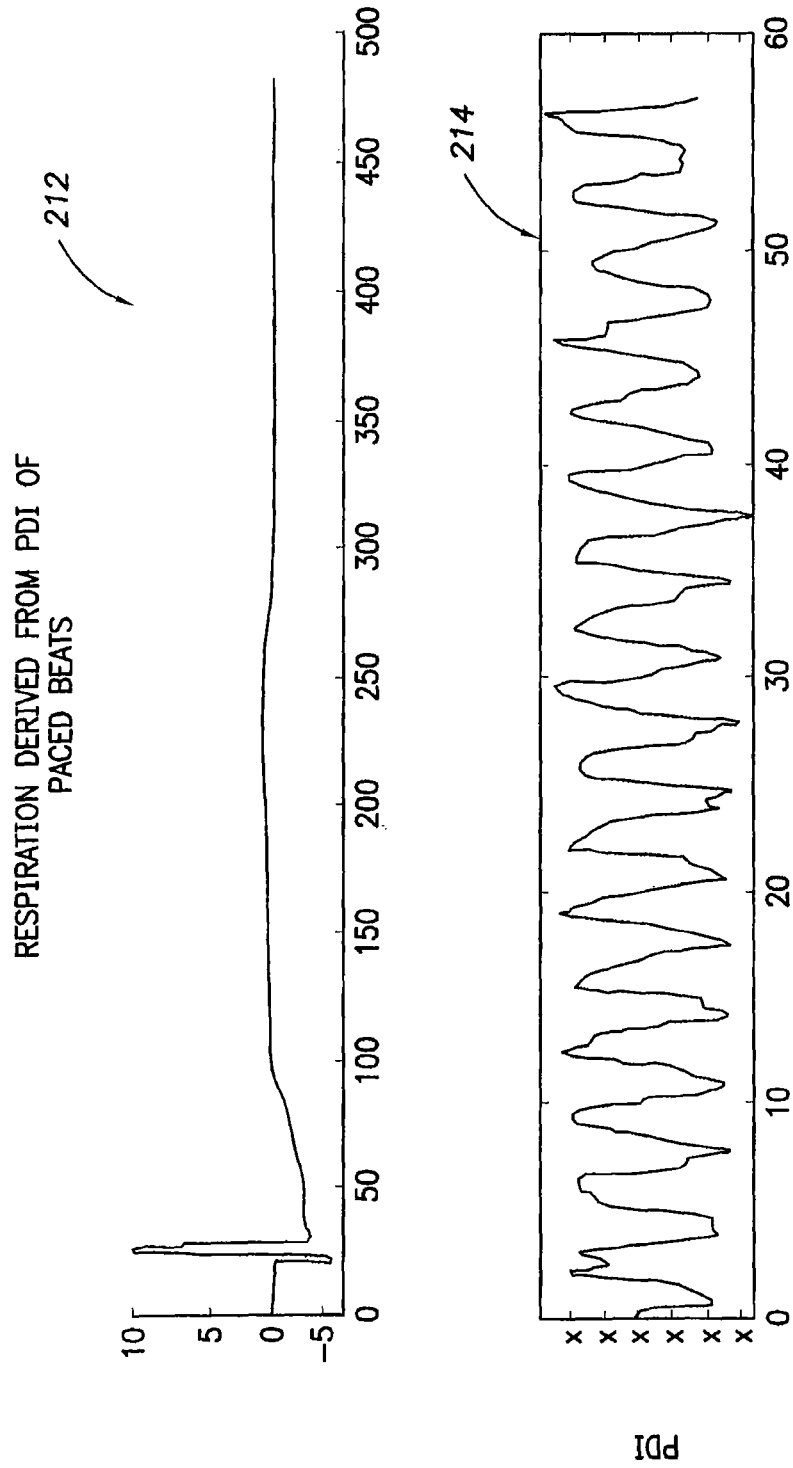
FIG. 4 is a graph illustrating exemplary unipolar IEGM patterns and resulting respiration patterns derived from an analysis of the integrals of QRS complexes generated via the method of FIG. 3.
Figure 5:
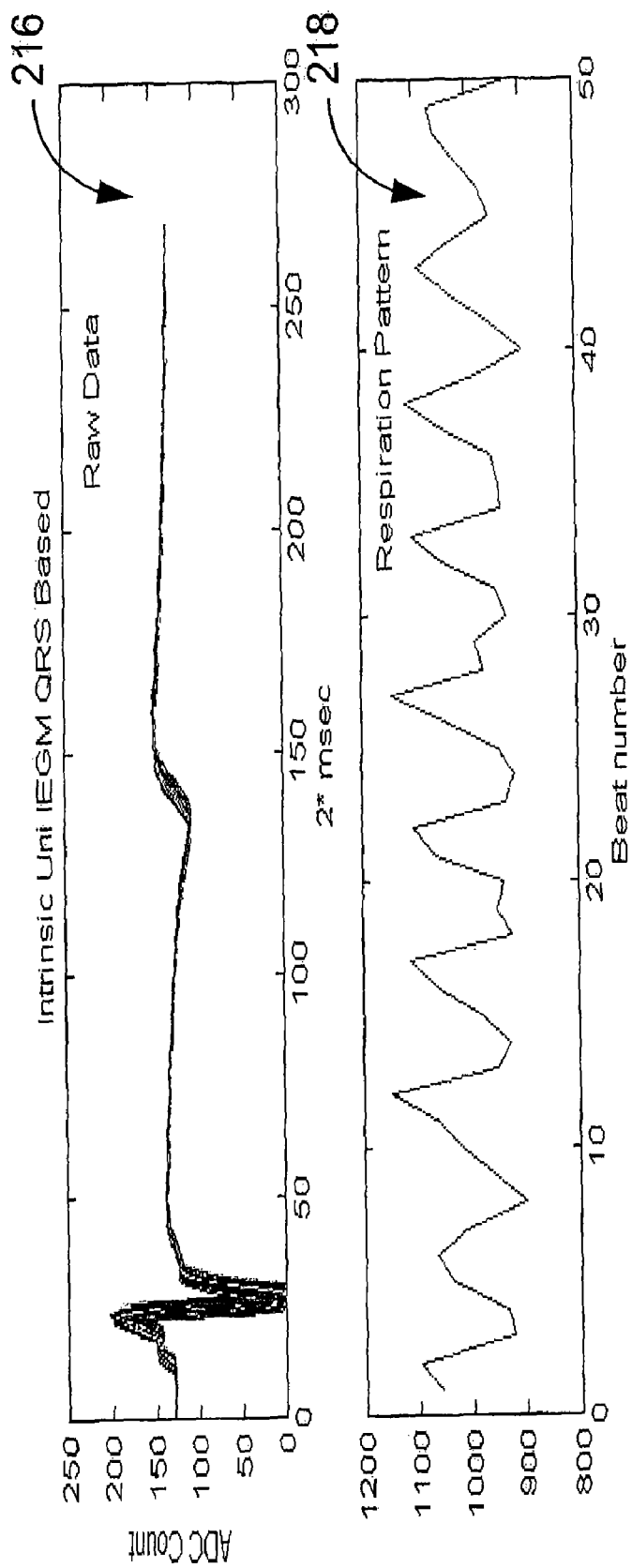
FIG. 5 is a graph illustrating exemplary unipolar IEGM patterns (shown superimposed on one another) and resulting respiration patterns derived from an analysis of the integrals of QRS-complexes generated via the method of FIG. 3.

Specific examples are illustrated in FIGS. 4-7. Within FIG. 4, a first graph 212 illustrates a unipolar V-IEGM signal for a canine test subject paced at 90 beats per minute (bpm). The vertical axis of the graph illustrates the output of an analog-to-digital converter (ADC) applied to the unipolar IEGM signal. The output ADC count is represented on arbitrary numerical scale (scaled to have only positive values), which is generally representative of the voltage associated with the unipolar IEGM signals, scaled so that all values are positive. FIG. 4 shows the IEGM signals associated with a plurality of cardiac cycles superimposed one upon the other so as to particularly illustrating slight variations in the shape of the patterns from cycle-to-cycle. The horizontal axis represents time within the individual cardiac cycles in milliseconds from a common starting point. A second graph, 214, illustrates the integrals of the VERs associated with each ventricular pacing pulse. In other words, the VER within each individual cardiac cycle of graph 212 was numerically integrated to obtain a single value, then those values were plotted as a function of time to produce graph 214. (The integrals of VERs are also referred to as PDIs.) Within graph 214, the vertical axis represents the integral value in arbitrary numerical units. The vertical horizontal axis represents time in seconds.

The integrals from the VERs of graph 212 have been connected by an interpolated line so as to provide a smooth representation of the respiration pattern of the canine test subject. More complex methods may be used to interpolate by using curve fitting of functions or by using a reconstruction filter. When a patient is awake/active, curve fitting can instead be used to provide smooth representation to calculate the breathing rate. As can be seen, there is clearly a cyclical pattern composed of alternating peaks and nadirs, from which respiration information may be derived. In particular, the rate of respiration may be derived (using otherwise conventional signal processing and analysis techniques) based upon the interval from one peak to another or the interval from one nadir to another. The relative amplitude of respiration may be derived based on comparison of the amplitude of the respective peaks and nadir of a given respiration cycle. Hence, although the respiration pattern of graph 214 does not necessarily closely represent an actual canine respiration pattern (which is typically more sinusoidal, particularly during fairly fast-paced respiration), the respiration pattern of graph 214 is nevertheless sufficient to obtain gross information pertaining to respiration, such as rate and relative amplitude from which episodes of abnormal respiration may be detected.

A second depolarization-based example is shown in FIG. 5, again for a canine test subject (although in this case, using intrinsic beats rather than paced beats). A first graph 216 illustrates QRS-complexes (as well as T-waves) derived from a unipolar ventricular lead. The IEGM signals associated with a plurality of cardiac cycles are superimposed one upon the other. Again, the vertical axis illustrates voltage in terms of an ADC count. The horizontal axis represents time within the individual cardiac cycles in milliseconds from a common starting point. The graph 218 shows a resulting, smoothed respiration pattern derived by integrating the QRS complexes shown in graph 216. Again, a cyclical pattern appears, which is representative of the respiration of the canine test subject. Gross information pertaining to respiration may be derived, including respiration rate and relative amplitude.

Figure 6:
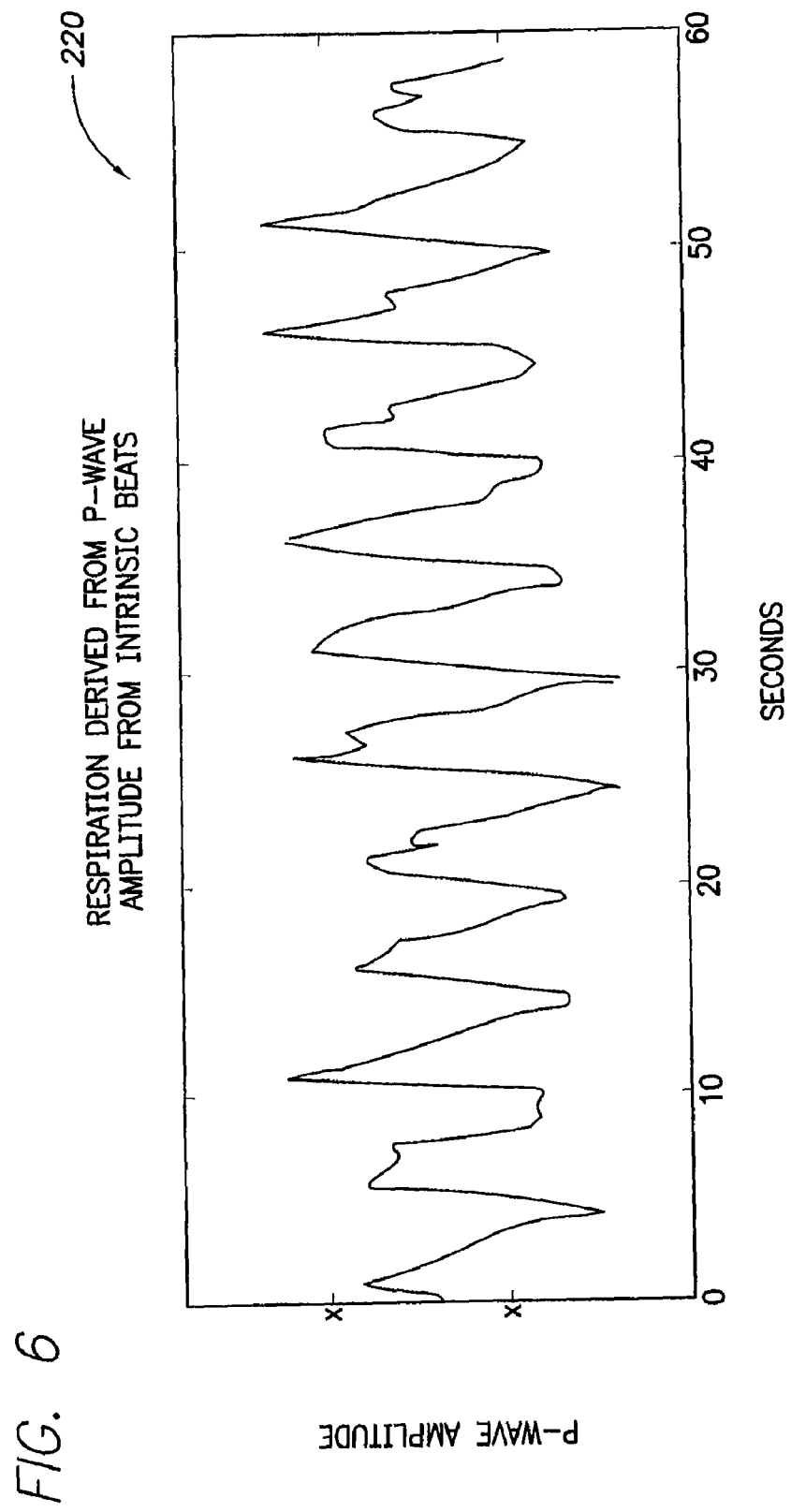
FIG. 6 is a graph illustrating respiration patterns derived from an analysis of the peak-to-peak amplitudes of P-waves generated via the method of FIG. 3.
Figure 7:
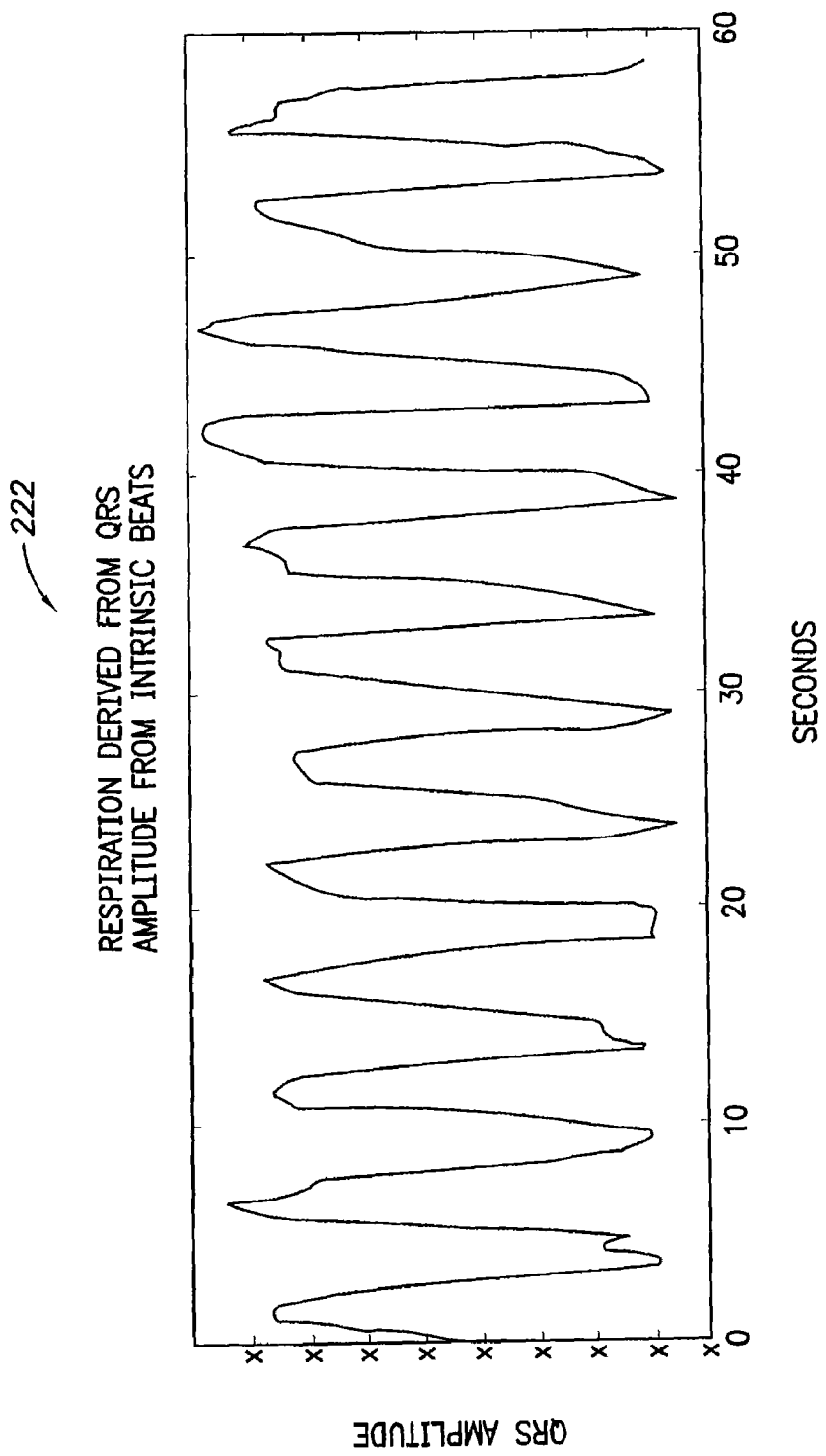
FIG. 7 is a graph illustrating respiration patterns derived from an analysis of the peak-to-peak amplitudes of intrinsic QRS-complexes generated via the method of FIG. 3.
Figure 8:
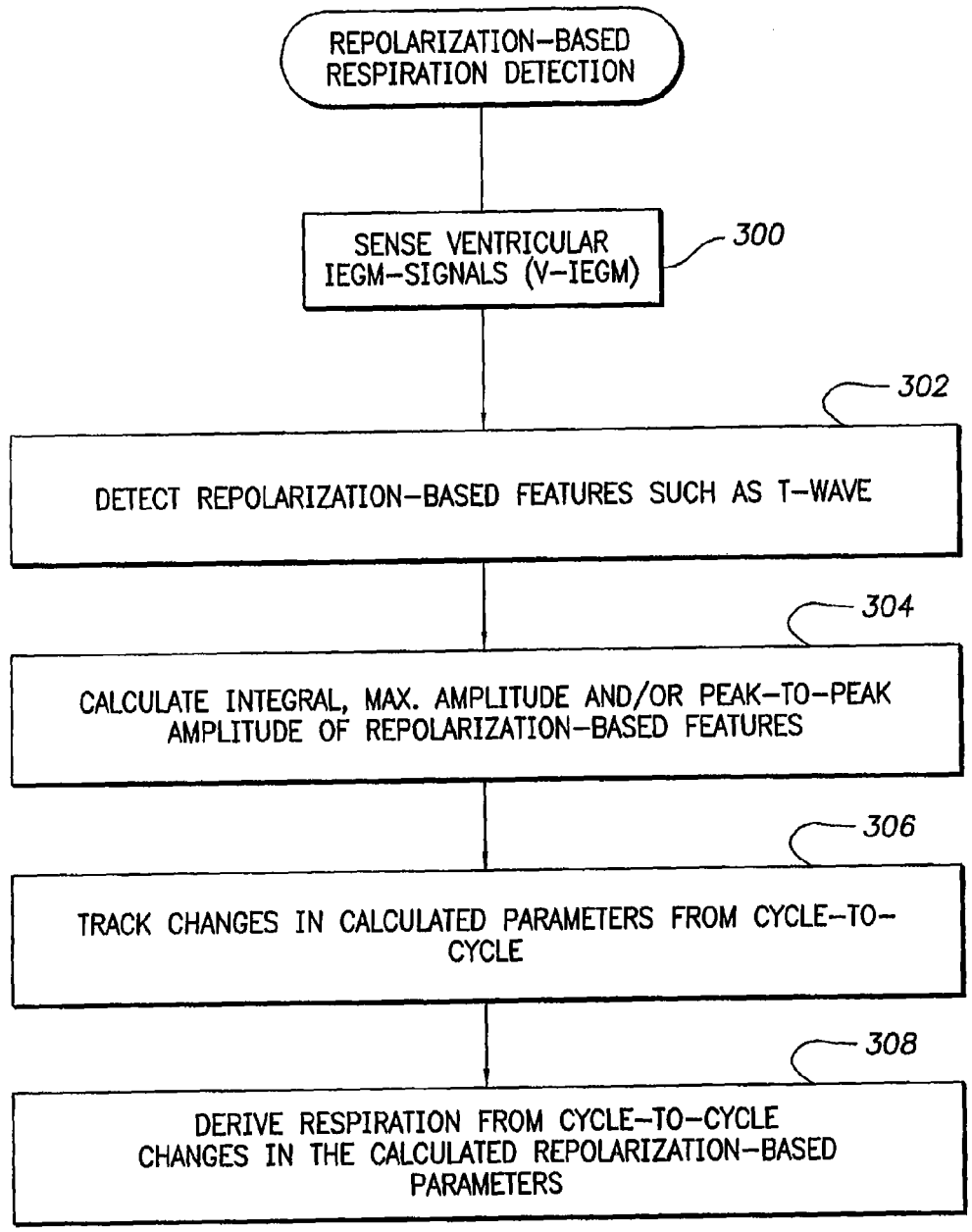
FIG. 8 is a flow chart specifically illustrating repolarization-based respiration detection techniques, which may be performed by the system of FIG. 1.

Another depolarization-based example is shown in FIG. 6, this one based on P-wave maximum (or peak) amplitude. In FIG. 6, only the resulting respiration pattern is shown (by way of graph 220), not the P-waves themselves. The vertical axis represents peak amplitude on an arbitrary voltage scale; whereas the horizontal axis illustrates time in seconds. The data was derived from a canine test subject based on atrial unipolar IEGM channel signals. The peak amplitude of each P-wave within each cardiac cycle was detected and the resulting plot of P-wave amplitude as a function of beat number smoothed. As with the other plots, a cyclical pattern is apparent, which is representative of respiration. A final depolarization-based example is shown in FIG. 7, which illustrates a respiration pattern (via graph 222) derived from QRS-complex maximum amplitudes sensed via a unipolar ventricular lead for a canine test subject. The maximum or peak amplitude of the QRS-complex of each cardiac cycle was detected, plotted along a time axis, and the resulting graph smoothed. Again, the gross features of the canine respiration pattern are clearly evident.

Thus, FIGS. 4-7 illustrate various examples of respiration patterns derived by separately plotting various depolarization-based features of IEGM signals. It is possible to also use two or more separate parameters to track respiration to improve accuracy. For example, respiration plots may be generated based upon QRS complexes derived separately from different channels, with the separate plots then merged to yield a single respiration plot (using, for example, otherwise conventional interpolation techniques). Alternatively, respiration patterns derived from different parameters, such as one from QRS-complexes and one from P-waves may be merged and combined to form a smooth time domain interpolation of breathing pattern. Additional morphological parameters, such as the peak slope of an event, might be suitable as well. Otherwise routine experimentation may be performed to determine which additional parameters might be suitable for tracking respiration and to identify the optimal combinations of various parameters to be combined so as to most reliably track patient respiration.

Repolarization-Based Respiration Detection Examples

Turning now to the FIGS. 8-12, examples specifically directed to the use of repolarization-based parameters (i.e. T-waves) will now be described. Many of the features of these techniques are similar to the depolarization-based techniques already described and so only pertinent differences will be described. Beginning at step 300 of FIG. 8, the pacer/ICD senses V-IEGM signals (or senses cross-chamber signals having strong ventricular components.) At step 302, a repolarization-based feature is detected within the IEGM signals, typically the ventricular T-wave. Potentially, atrial repolarization events may also be detected and used to track respiration. However, atrial repolarization events are typically of low amplitude and difficult to detect and thus are not optimal for use in tracking respiration. Hence, the use of atrial repolarization events will not be described in any great detail herein.) At step 304, the pacer/ICD calculates the numerical integral, the maximum amplitude and/or the peak-to-peak amplitude of the detected T-waves. At step 306, the pacer/ICD tracks changes in the calculated T-wave parameters from cycle-to-cycle and, at step 308, derives respiration based on changes in the T-waves. In this regard, far-field ventricular depolarization events as detected in the atrium can be used to aid in tracking repolarization.

Figure 9:
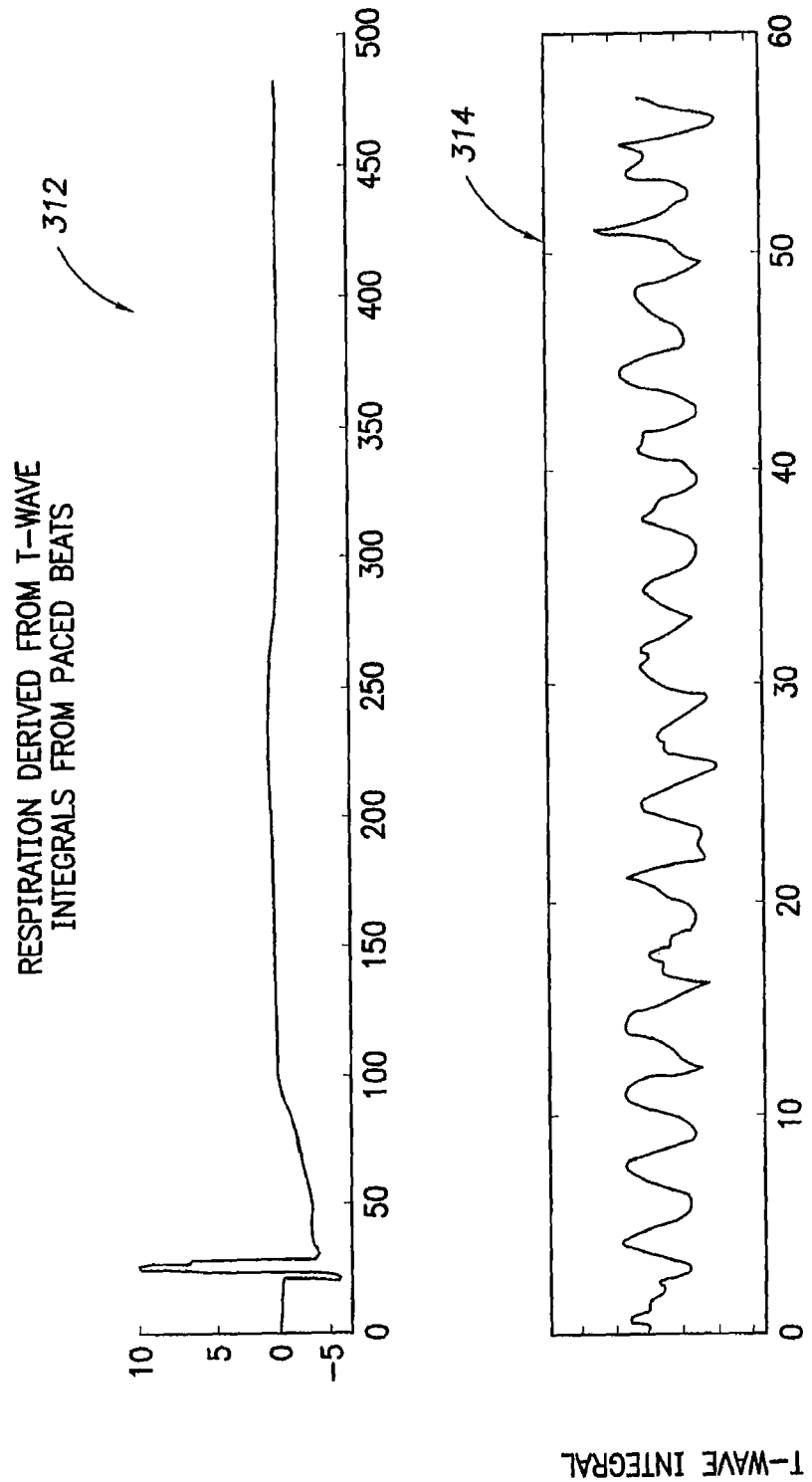
FIG. 9 is a graph illustrating exemplary unipolar ventricle paced IEGM patterns and resulting respiration patterns derived from an analysis of the integrals of T-waves generated via the method of FIG. 8.
Figure 10:
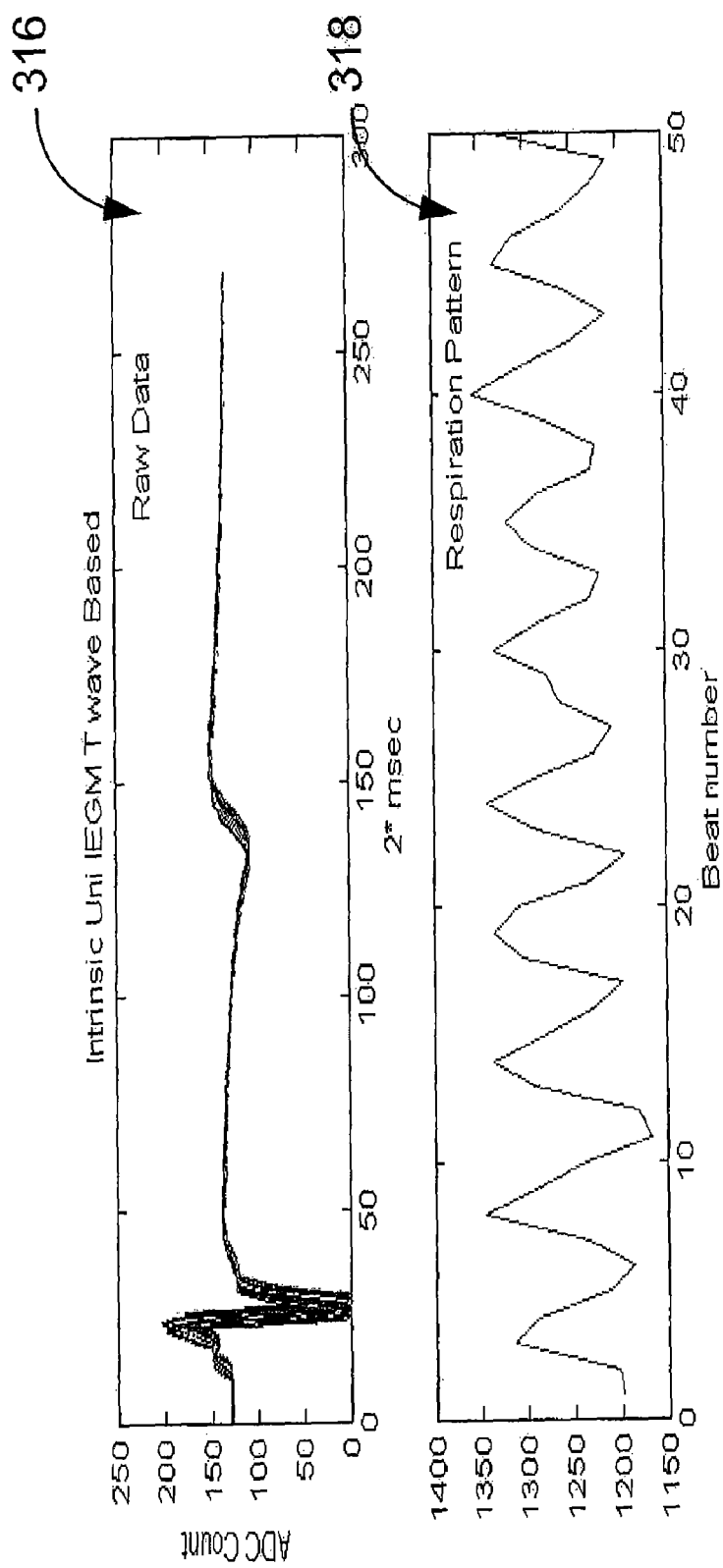
FIG. 10 is a graph illustrating exemplary unipolar intrinsic Ventricular IEGM patterns (shown superimposed on one another) and resulting respiration patterns derived from an analysis of the integrals of T-waves generated via the method of FIG. 8.

Specific T-wave-based examples are illustrated in FIGS. 9-12 for a canine test subject. Within FIG. 9, graph 312 illustrates a unipolar V-IEGM signal for a canine test subject paced at 90 bpm. FIG. 9 shows the IEGM signals associated with a plurality of cardiac cycles superimposed one upon the other. The horizontal axis represents time within the individual cardiac cycles in milliseconds from a common starting point. Graph 314 illustrates the integrals of the T-waves from cycle-to-cycle. The individual data points derived by integrating the T-waves of graph 312 have been interpolated so as to provide a smooth representation of the respiration pattern of the canine test subject. A cyclical pattern appears, from which respiration information may be derived. Although the respiration pattern of graph 314 does not closely represent an actual respiration pattern, graph 314 is nevertheless sufficient to obtain gross information pertaining to patient respiration, such as rate, depth and effort.

A second repolarization-based example is shown in FIG. 10, again for a canine test subject (although in this case, using intrinsic beats rather than paced beats). A first graph 316 illustrates T-waves (as well as QRS-complexes) derived from a unipolar ventricular lead, with the T-waves superimposed one upon the other. Graph 318 shows the resulting, interpolated respiration pattern derived by integrating the T-waves. Again, a cyclical pattern appears, representative of the respiration of a canine test subject from which gross information pertaining to respiration may be derived, including respiration rate and relative amplitude.

Figure 11:
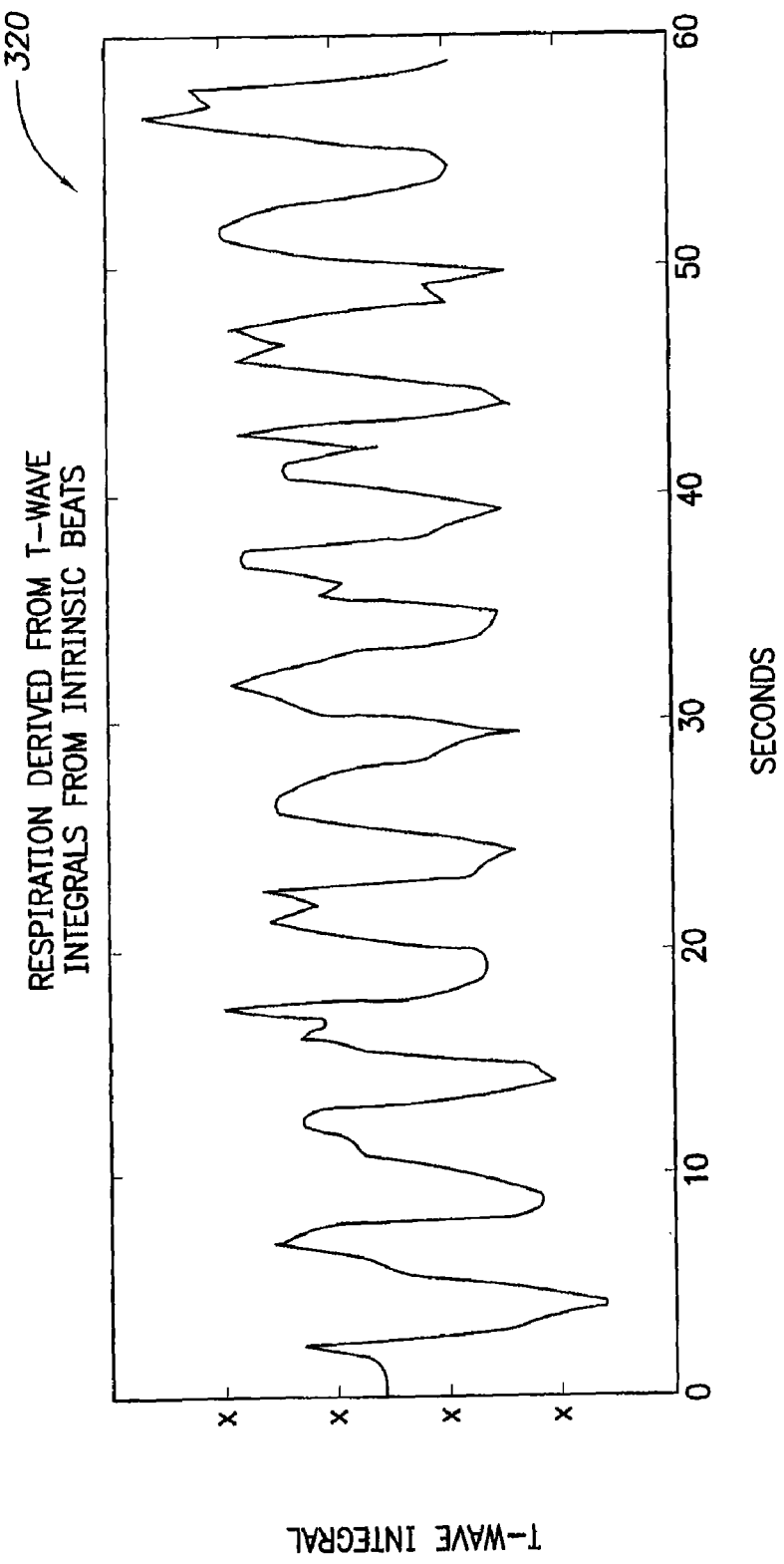
FIG. 11 is a graph illustrating respiration patterns derived from an analysis of the peak-to-peak amplitudes of T-waves generated via the method of FIG. 8.
Figure 12:
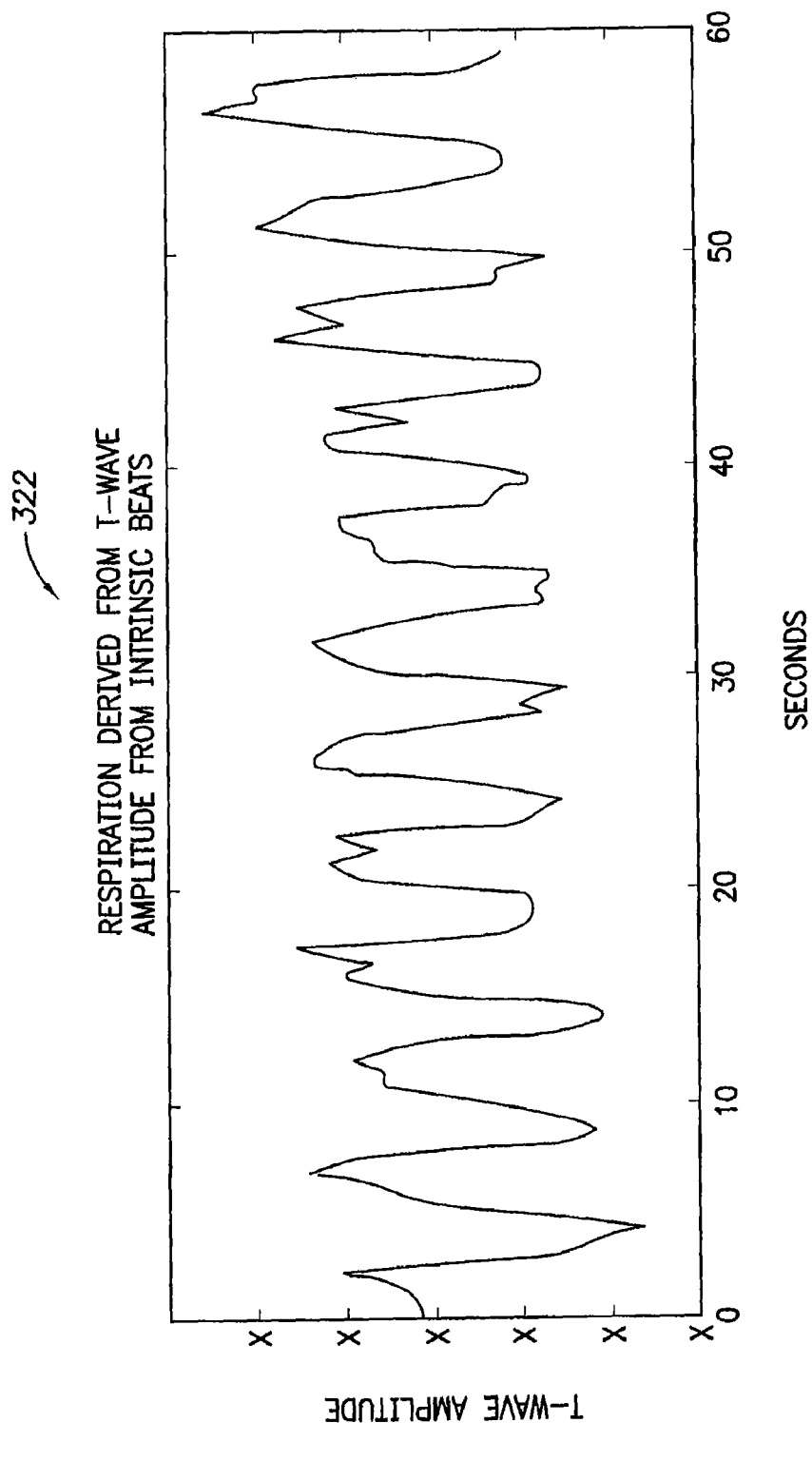
FIG. 12 is a graph illustrating respiration patterns derived from an analysis of the maximum amplitudes of T-waves generated via the method of FIG. 8.
Figure 13:
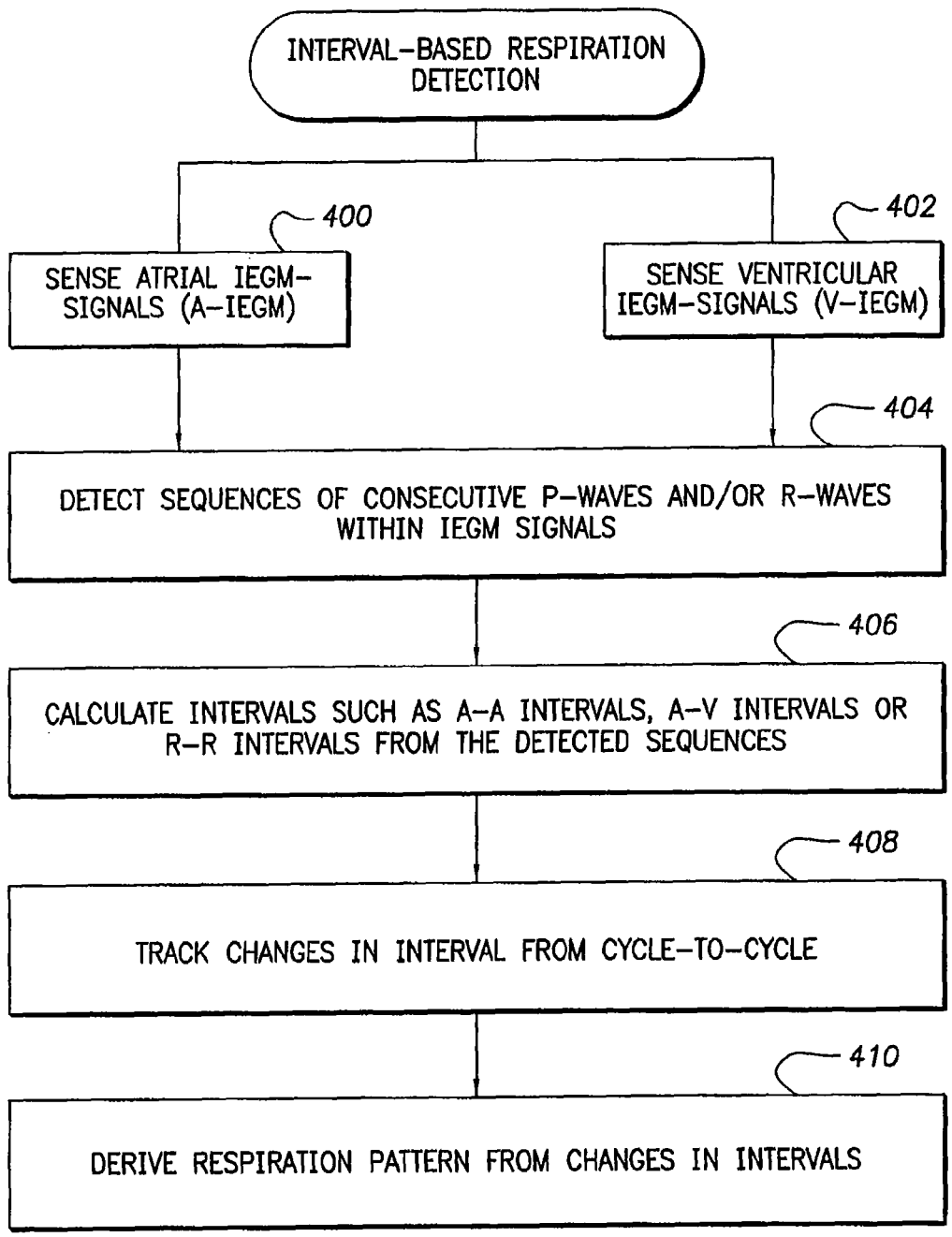
FIG. 13 is a flow chart specifically illustrating interval-based respiration detection techniques, which may be performed by the system of FIG. 1.

Another repolarization-based example is shown in FIG. 11, this one based on T-wave maximum amplitude. In FIG. 11, only the resulting respiration pattern shown (by way of graph 320), not be the T-waves themselves. The peak amplitude of each T-wave within each cardiac cycle was detected and the resulting plot of T-wave amplitude as a function of beat number is smoothed. As with the other plots, a clearly cyclical pattern appears, representative of respiration. A final repolarization-based example is shown in FIG. 12, which illustrates a respiration pattern (via graph 322) derived from T-wave maximum amplitudes. The maximum amplitude of the T-wave of each cardiac cycle was detected, plotted along a time axis, and the resulting graph smoothed. Again, the gross features of the respiration pattern of the canine test subject are clearly evident.

Thus, FIGS. 8-12 illustrate various examples of respiration patterns derived by separately plotting various repolarization-based features of IEGM signals. It is possible to also use two or more separate T-wave parameters to track respiration, such as both maximum amplitude and peak-to-peak amplitude. Alternatively, respiration patterns derived from different events, such as one from QRS-complexes and one from T-waves may be merged. Using multiple parameters or multiple IEGM channel signals may enhance the specificity with which respiration may be tracked. Otherwise routine experimentation may be performed to determine optimal combinations of the parameters to be combined so as to most reliably track patient respiration.

Interval-Based Respiration Detection Examples

In addition to the aforementioned beat-by-beat tracking techniques, which seek to track respiration based on changes in morphology, intervals between successive beats (or between successive features of an individual beat) may additionally, or alternatively, be employed. This is summarized in FIG. 13. Beginning at steps 400 and 402, the pacer/ICD senses A-IEGM and V-IEGM signals. At step 404, pacer/ICD then detects sequences of consecutive P-waves and/or R-waves within the IEGM signals. At step 406, selected intervals are calculated, e.g., A-A intervals, AV intervals or R-R intervals. A-A intervals, which represent the intervals between consecutive P-waves, are preferably derived from A-IEGM signals; whereas R-R intervals, which represent the intervals between consecutive QRS-complexes, are preferably derived from V-IEGM signals. Typically, a pacer/ICD calculates these intervals as part of its routine operations. In any case, at step 408, the pacer/ICD then tracks changes in the intervals from cycle-to-cycle and, at step 410, derives respiration from changes in the intervals over time, typically, over at least a few dozen cardiac cycles. For example, a given interval value, such as an A-A interval derived from an A-IEGM signals, may be calculated between each successive pair of P-waves, with the value of the interval then plotted as a function of time or as a function of cardiac cycle number (as in some of the examples described above) so as to track the cyclical features of respiration. As before, the respiration patterns derived in this manner may not closely approximate the actual smooth respiration patterns of patient, but nevertheless provide sufficient information from which respiration rate and relative amplitude can be derived and from which episodes of abnormal respiration may be detected.

The use of changes in R-R and ST intervals derived from V-IEGM signals are described in detail with reference to the Andersson cited above. The technique of FIG. 13, however, is not limited to R-R/ST interval variability derived from V-IEGM signals but, as noted, may be based on either A-IEGM or V-IEGM signals, and may further be based on A-A intervals or AV intervals, or some combination thereof. Unipolar or Bipolar signals may be employed, as well as cross-chamber signals. The respiration patterns derived from cycle-to-cycle changes in intervals may be merged with respiration patterns derived from depolarization events or repolarization events, described above, to provide further specificity.

Abnormal Respiration Detection and Therapy

Figure 14:
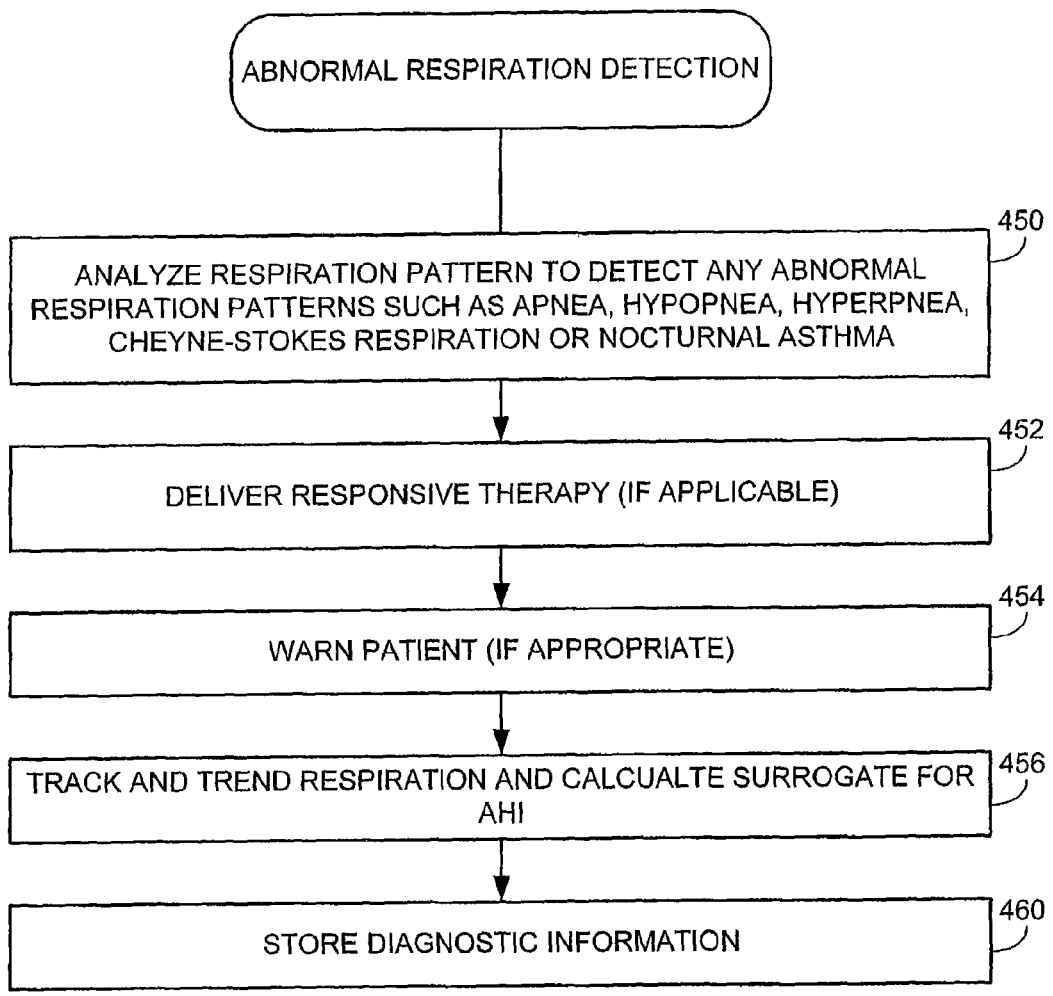
FIG. 14 is a flow chart illustrating abnormal respiration detection techniques, which may be performed by the system of FIG. 1, based on respiration patterns detecting using the techniques of FIGS. 2-13.

What have been described thus far are various techniques for tracking respiration patterns based on features of IEGM signals. With reference to FIG. 14, techniques for detecting episodes of abnormal respiration based on the respiration patterns and delivering therapy will now be described. At step 450, the pacer/ICD analyzes the detected respiration pattern to detect episodes of abnormal respiration such as apnea and hypopnea, hyperpnea, nocturnal asthma, and CSR, based on respiration rate and/or amplitude. In general, otherwise conventional techniques for detecting episodes of abnormal respiration, which use respiration rates or respiration amplitudes, may be employed. Preferably, however, the techniques set forth in FIGS. 18-27 are employed to detect abnormal respiration. These techniques are described below. Once an episode of abnormal respiration is detected, otherwise conventional techniques may be used to identify the particular form of abnormal respiration, i.e. to distinguish between apnea, hypopnea, hyperpnea, CSR, etc.

Briefly, apnea may be detected based upon a lack of any significant amplitude variations within the detected respiration patterns extending over a predetermined period of time. In one example, an apnea detection amplitude threshold value may be specified along with an apnea detection time threshold value. If the respiratory amplitude derived from the respiration patterns does not exceed the amplitude threshold value for at least a period of time greater than the time threshold value, then apnea is presumed. Typically, an episode of apnea is not deemed to have occurred unless there is a lack of respiration for at least ten seconds and so a time threshold of at least ten seconds may be employed. A suitable amplitude threshold value may be determined via routine experimentation for use with respiration patterns derived from particular IEGM parameters. In this regard, the amplitude threshold value for use with the respiration patterns derived from QRS-complexes may differ from one derived from the P-waves or T-waves. The values may also differ from patient to patient. Note that the amplitude and morphology changes may also depend on body position, and also on the rhythm types, i.e. in case of a pacer/ICD, it would be advisable to have different thresholds for different rhythm combinations: A-R, A-V, P-R, P-V. Suitable amplitude threshold values may be specified following implant of device based on the specific characteristics of patient in which the device is implanted or automatically updated during routine working of the algorithm.

More complex techniques may be employed identifying each episode of apnea. In one example, a combination of raw respiration parameters generated above and various thresholds on each parameter are fed into an apnea episode detection system, specifically configured for detecting apnea. Additionally, simple or more complex methods than zero crossings can be used to determine breathing rate. Depth of breathing and effort of breathing can be calculated. The local variability in each parameter as derived from mean and standard-deviations etc. may also be fed as variables into the apnea episode detection system. (Other variables that can be derived include median, peak-to-peak changes, and inter-quartile range.) Using the long term autonomic interval-based variability as well as the individual event-based morphological variability, it is possible to detect differences between obstructive apnea, central apnea, nocturnal apnea, CSA and flow hypopnea etc.

Hypopnea may be detected based upon respiratory amplitude that exceeds the apnea threshold but falls below a separate hypopnea amplitude threshold. As with apnea, a time threshold value (such as 10 seconds) may be specified as well. Hence, if there is at least some respiration, but the amplitude of that respiration falls below an amount deemed healthy for the patient, hypopnea is presumed. As with the various apnea thresholds, separate hypopnea threshold values may be specified for use with different respiration detection techniques (i.e. depolarization-based techniques versus repolarization-based techniques) and for use with different patients, preferably determined on a patient by patient basis following implant of the device. Alternative and more complex hypopnea detection techniques may be employed as well.

Hyperpnea/asthma may be detected based upon a pattern exhibiting excessively rapid respiration (or attempted respiration.) Accordingly, an hyperpnea/asthma amplitude detection threshold may be specified along with a hyperpnea/asthma respiration rate and effort threshold. If amplitude derived from the respiration pattern exceeds the hyperpnea/asthma respiration amplitude detection threshold while the respiration rate (also derived from the respiration pattern) also exceeds it respective threshold, hyperpnea/asthma is thereby presumed. Again, suitable thresholds may be determined on the patient basis following implant of device. Alternative and more complex hyperpnea/asthma or CSR detection techniques may be employed as well.

Hyperpnea usually may be distinguished from asthma based on the presence or absence of normal respiration preceding the attack. Hyperpnea usually follows an episode of apnea/hypopnea; whereas asthma usually follows a period of otherwise normal breathing. Episodes of nocturnal asthma may be distinguished from other asthma attacks merely by determining whether the patient is asleep, using otherwise conventional sleep detection techniques. Examples of sleep detection techniques are set forth in: U.S. Pat. No. 5,476,483, to Bornzin et al., entitled "System and Method for Modulating the Base Rate During Sleep for a Rate-responsive Cardiac Pacemaker" and U.S. Pat. No. 6,128,534 to Park et al., entitled "Implantable Cardiac Stimulation Device And Method For Varying Pacing Parameters To Mimic Circadian Cycles."

CSR may be detected using otherwise conventional techniques based on its characteristic pattern of alternating periods of apnea/hypopnea and hyperpnea. See, e.g., U.S. Pat. No. 6,830,548 to Bonnet, et al., "Active Medical Device Able to Diagnose a Patient Respiratory Profile."

Once an episode of abnormal respiration has been detected then, at step 452, the pacer/ICD delivers appropriate therapy (assuming it is properly equipped). For example, in response to detection of frequent episodes of apnea/hypopnea, atrial overdrive pacing therapy may be applied in an attempt to prevent the onset of additional episodes. A particularly effective atrial overdrive pacing technique, referred to herein as dynamic atrial overdrive (DAO) pacing, is described in U.S. Pat. No. 6,519,493 to Florio et al., entitled "Methods and Apparatus for Overdrive Pacing Heart Tissue Using an Implantable Cardiac Stimulation Device". Routine experimentation may be performed to identify optimal DAO pacing parameters for use with patients with apnea/hypopnea. The aggressiveness of DAO therapy may be adjusted based upon the frequency or duration of episodes of apnea/hypopnea.

Anti-apneic medications may be delivered via an implantable drug pump, if so equipped. Examples of medications that may be helpful in patients with apnea are set forth the following patents: U.S. Pat. No. 6,331,536 to Radulovacki, et al., entitled "Pharmacological Treatment for Sleep Apnea"; U.S. Pat. No. 6,432,956 to Dement, et al., entitled "Method for Treatment of Sleep Apneas"; U.S. Pat. No. 6,586,478 to Ackman, et al., entitled "Methods and Compositions for Improving Sleep"; and U.S. Pat. No. 6,525,073 to Mendel, et al., entitled "Prevention or Treatment of Insomnia with a Neurokinin-1 Receptor Antagonist". Depending upon the particular medication, alternative compounds may be required for use in connection with an implantable drug pump. Routine experimentation may be employed to identify medications for treatment of sleep apnea that are safe and effective for use in connection with an implantable drug pump. Dosages may be titrated based upon the frequency or duration of episodes of apnea.

During the actual episode of apnea/hypopnea, an implantable alarm (such as alarm 18 of FIG. 1) may be activated to awaken the patient (assuming the patient is sleeping) in an attempt to terminate the episode of apnea/hypopnea. Alternatively, a bedside alarm may be activated by transmission of appropriate wireless control signals. Activation of an alarm to awaken the patient is preferably employed only if other therapy is found to be ineffective, since awakening the patient interrupts with the patient's natural sleeping patterns.

If implantable phrenic nerve stimulators are implanted, apnea/hypopnea therapy can also involve delivery of rhythmic electrical stimulation to the phrenic nerves to mimic breathing (assuming the apnea/hypopnea is due to a lack of phrenic nerve signals.) Examples of phrenic nerve stimulators are set forth in U.S. Pat. No. 5,056,519 to Vince, entitled "Unilateral Diaphragmatic Pacer" and in U.S. Pat. No. 6,415,183 to Scheiner, et al., entitled "Method and Apparatus for Diaphragmatic Pacing", which are incorporated by reference herein. Other respiratory nerves may be stimulated as well. U.S. Pat. No. 5,911,218 to DiMarco, entitled "Method and Apparatus for Electrical Stimulation of the Respiratory Muscles to Achieve Artificial Ventilation in a Patient" describes stimulation of nerves leading to intercostal muscles.

If an implantable hypoglossyl nerve stimulator is implanted, therapy can also involve delivery of stimulation to the hypoglossyl nerves in response to obstructive sleep apnea. Examples of hypoglossyl nerve stimulators are set forth in U.S. Patent Application 2003/0216789 of Deem et al., entitled "Method and System for Treating Sleep Apnea."

Insofar as CSR therapy is concerned, CSR often arises due to CHF and so CSR can often be remedied by addressing the underlying CHF. See, e.g. U.S. patent application Ser. No. 10/792,305, filed Mar. 2, 2004, entitled "System And Method For Diagnosing And Tracking Congestive Heart Failure Based On The Periodicity Of Cheyne-Stokes Respiration Using An Implantable Medical Device" (A04P1019). Accordingly, upon detection of episodes CSR, the pacer/ICD preferably employs otherwise conventional techniques to detect CHF and, if CHF is present, any of a variety of therapies directed to mitigating CHF may be implemented by the device. For example, cardiac resynchronization therapy (CRT) may be performed to improve cardiac function. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing". CHF therapy may also include delivery of medications via an implantable drug pump, if so equipped. Exemplary CHF medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of CHF that are safe and effective for use in connection with an implantable drug pump.

Additionally, during an individual episode of CSR, the implantable alarm or external bedside alarm may be triggered to awaken the patient to break the cycle of CSR. Again, activation of an alarm to awaken the patient is preferably employed only if other forms of therapy are found to be ineffective. See, also, U.S. patent application Ser. No. 10/844,023, filed May 11, 2004, entitled "System and Method for Providing Demand-Based Cheyne-Stokes Respiration Therapy Using an Implantable Medical Device" (A04P1042).

Insofar as hyperpnea is concerned, hyperpnea may arise during CSR or may arise during an asthma attack. Hyperpnea arising due to CSR is preferably addressed via CSR therapy. See, also, U.S. patent application Ser. No. 10/829,719, filed Apr. 21, 2004, entitled "System and Method for Applying Therapy during Hyperpnea Phase of Periodic Breathing Using an Implantable Medical Device" (A04P1037). Hyperpnea arising due to asthma may be addressed by addressing the asthma via suitable medications delivered via the implantable drug pump. Examples of asthma medications are set forth, for example, in U.S. Pat. No. 4,089,959 to Diamond, entitled "Long-Acting Xanthine Bronchodilators and Anti-allergy Agents". Depending upon the particular medication, alternative compounds may be required for use in connection with an implantable drug pump. Routine experimentation may be employed to identify medications for treatment of asthma that are safe and effective for use in connection with an implantable drug pump. Dosages may be titrated as needed based on tracking and trending of such breathing patterns.

Additional techniques may be used, if desired, to corroborate the detection of an episode of abnormal respiration made using the techniques of the invention before therapy is delivered. See, e.g., U.S. patent application Ser. No. 10/883,857, filed Jun. 30, 2004, entitled "System And Method For Real-Time Apnea/Hypopnea Detection Using An Implantable Medical System (A04P1057) and U.S. patent application Ser. No. 10/821,241, filed Apr. 7, 2004, entitled "System And Method For Apnea Detection Using Blood Pressure Detected via an Implantable Medical System" (A04P1034).

Continuing with FIG. 14, at step 454, suitable warning signals may be delivered to alert the patient, his/her physician or other medical personnel to any episodes of abnormal breathing.

At step 456, the device also tracks and trends changes in respiration patterns. This may be achieved by continuously monitoring the patient for apneic or hypopneic events and quantifying the amount of apnea based on an index. A commonly used index is the apnea hypopnea index (AHI). This index is based on counting apnea and hypopneas that occur over the entire night and dividing the number of apnea and hypopneas by the total sleep time in hours. This invention provides a surrogate for AHI using the number of IEGM detected apneas and hypopneas divided by the total rest time in hours. The total rest time approximates the total sleep time and is derived measuring the time that a patient is at profound rest by using an activity sensor as set forth in: in aforementioned patent to Bornzin et al. (U.S. Pat. No. 5,476,483.) Alternatively, the total sleep time may be estimated using IEGM based respiratory rate trends. During sleep, the respiration rate diminishes below the wakeful respiration rates and sleep time may be easily determined using the IEGM based breathing rate trend. In fact, by making a histogram of the IEGM breathing rates sampled at equal intervals throughout the day and counting the number of intervals in the lowest mode an estimate of the duration of sleep may be performed. Another method that may be used to estimate the total sleep time throughout the day depends on a direct current (DC) accelerometer to quantify the amount of time that a patient is lying down as set forth in U.S. Pat. No. 6,466,821, to Pianca et al., entitled "AC/DC Multi-Axis Accelerometer for Determining Patient Activity and Body Position". It is also be possible to use Heart rate dynamics to differentiate between awake and sleep state. See, Redmond et al., "Cardiorespiratory-based sleep staging in subjects with obstructive sleep apnea," IEEE Trans Biomed Eng 2005; 53(3):485-96.

Figure 15:
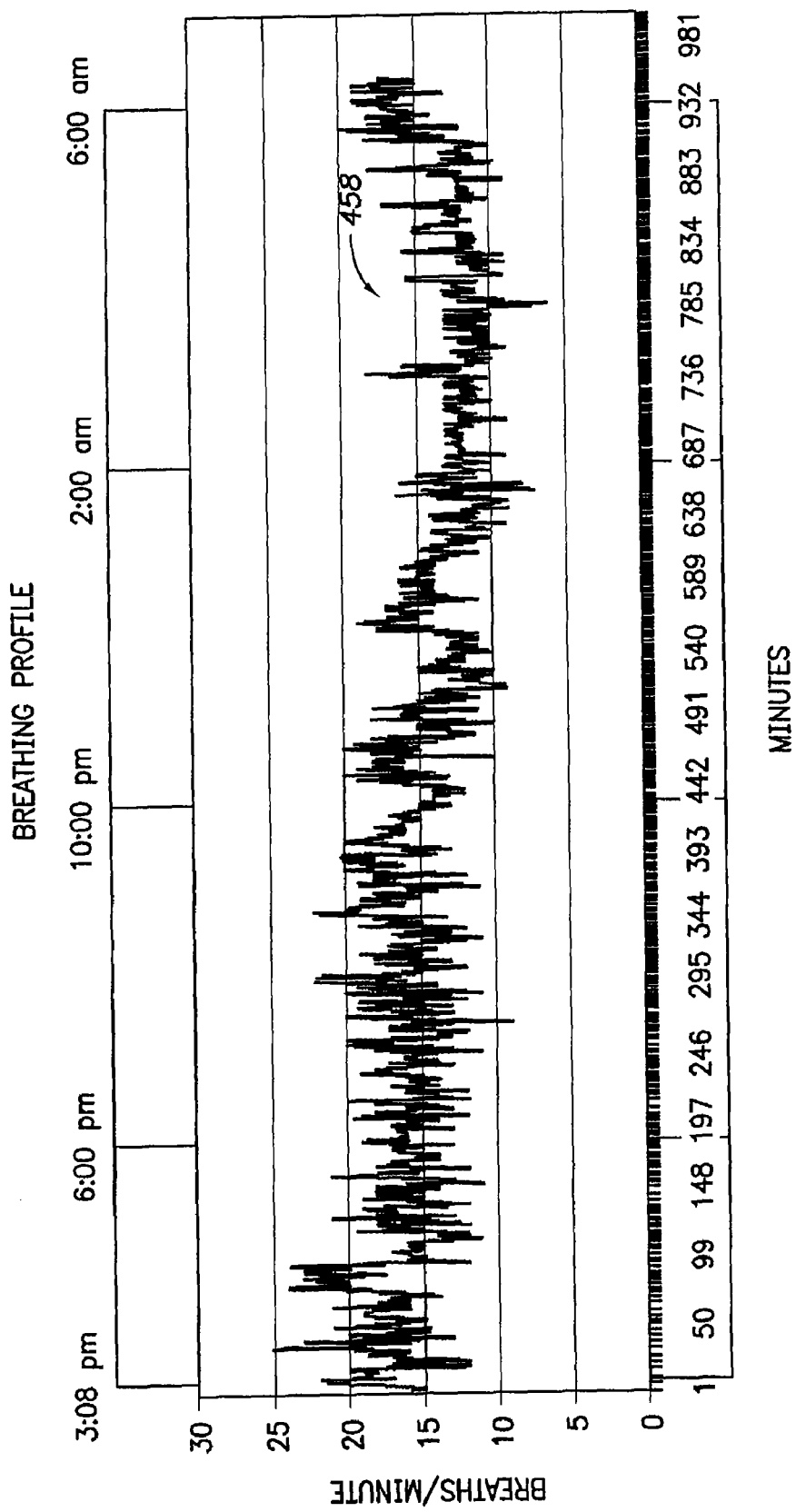
FIG. 15 is a graph illustrating a sixteen hour respiration pattern derived from an analysis of the maximum amplitudes of T-waves for use in identifying trends for use with the method of FIG. 14.

An exemplary trend pattern is illustrated in FIG. 15, which provides an exemplary breathing pattern (in terms of breathes per minute) tracked over a period of about sixteen hours. A portion 458 illustrate respiration rate during sleep. By analyzing trends contained in breathing patterns such as that of FIG. 15, the aforementioned surrogate AHI value can be obtained.

Returning to FIG. 14, appropriate diagnostic information is stored at step 460 so that a medical professional can subsequently review the trend data or any therapy delivered and evaluate its effectiveness.

What have been described are various techniques for tracking respiration via IEGM signals, detecting episodes of abnormal respiration and delivering appropriate therapy. For the sake of completeness, a detailed description of an exemplary pacer/ICD for controlling these functions will now be provided. However, principles of invention may be implemented within other pacer/ICD implementations or within other devices. In particular, techniques of the invention are also applicable to detecting respiration via surface EKG signals and hence are not necessarily limited to use with implantable devices. In this regard, it is known that the mean cardiac axis and EKG morphology is influenced by electrode motion relative to the heart and by changes in thoracic electrical impedance as the lungs fill and empty. The sinus rate is modulated by vagal influences in synchronization with respiration. Pressure changes (i.e. breathing-related as well as cardiac cycle-related pressure changes) influence IEGM morphology.

Pacemaker/ICD

FIG. 16 provides a simplified block diagram of the pacer/ICD, which is a multi-chamber stimulation device capable of treating both fast and slow arrhythmias with stimulation therapy, including cardioversion, defibrillation, and pacing stimulation (as well as capable of tracking respiration, detecting episodes of abnormal respiration and delivering appropriate therapy.) To provide atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 624 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 16, it should also be understood that additional stimulation leads (with one or more pacing, sensing and/or shocking electrodes) may be used in order to efficiently and effectively provide pacing stimulation to the left side of the heart or atrial cardioversion and/or defibrillation. The leads are also employed for sensing ID tag signals from medications equipped with active ID transmitters.

Figure 17:
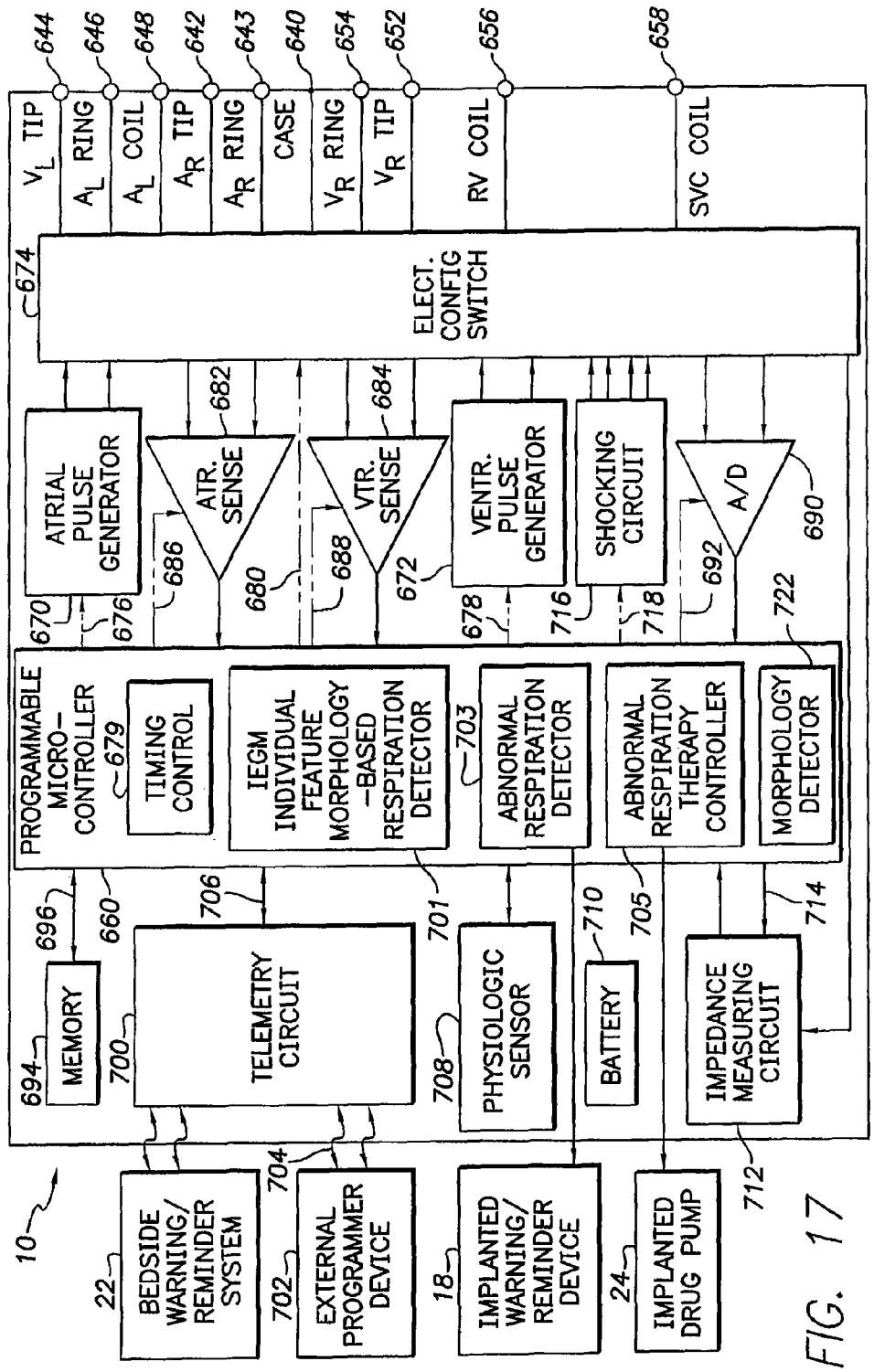
FIG. 17 is a functional block diagram of the pacer/ICD of FIG. 16, illustrating basic circuit elements that provide cardioversion, defibrillation and/or pacing stimulation in four chambers of the heart and particularly illustrating an IEGM-based respiration pattern detector, an IEGM-based abnormal respiration episode detector, and an abnormal respiration therapy controller.

A simplified block diagram of internal components of pacer/ICD 10 is shown in FIG. 16. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 640 for pacer/ICD 10, shown schematically in FIG. 17, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 643. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 632, right ventricular ring electrode 634, the RV coil electrode 636, and the SVC coil electrode 638, respectively. Separate terminals (not shown) may be provided for connecting the implanted warning/reminder device 18 and the implanted drug pump 20, which are instead shown coupled directly to internal functional components of the pacer/ICD that control these devices. (The warning/reminder device is so named as it can be programmed to deliver reminders to the patient to take certain medications, as well as to deliver warnings as to medical conditions such as apnea.)

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry.

Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 17, an atrial pulse generator 670 and a ventricular/impedance pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor 708, commonly referred to as a "rate-responsive" sensor because it is typically used to adjust pacing stimulation rate according to the exercise state of the patient. However, the physiological sensor 708 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV Delay, V-V Delay, etc.) at which the atrial and ventricular pulse generators, 670 and 672, generate stimulation pulses. While shown as being included within pacer/ICD 10, it is to be understood that the sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 17. The battery 710 may vary depending on the capabilities of pacer/ICD 10. If the system only provides low voltage therapy, a lithium iodine or lithium copper fluoride cell may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, pacer/ICD 10 is preferably capable of high voltage therapy and batteries or other power sources appropriate for that purpose are employed.

As further shown in FIG. 17, pacer/ICD 10 is shown as having an impedance measuring circuit 712 which is enabled by the microcontroller 660 via a control signal 714. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Microcontroller 60 also includes an IEGM individual feature morphology-based respiration detector 701 for detecting respiration based upon one or more IEGM channel signals using the techniques described above. An abnormal respiration pattern detector 703 is also provided the purposes of detecting apnea, hypopnea, etc. using techniques described above. Additionally, an abnormal respiration therapy controller 705 is provided for controlling therapy in response to an episode of abnormal respiration, again using techniques already described. Depending upon the implementation, the various components may be implemented as separate software modules. However, the modules may be combined so as to permit single modules to perform multiple functions.

Further Abnormal Respiration Detection Techniques

Turning now to FIGS. 18-27, techniques particularly directed to detecting abnormal respiration will be described. The techniques may be used, for example, by the pacer/ICD of FIGS. 16-17 to implement step 450 of the technique of FIG. 14.

Figure 18:
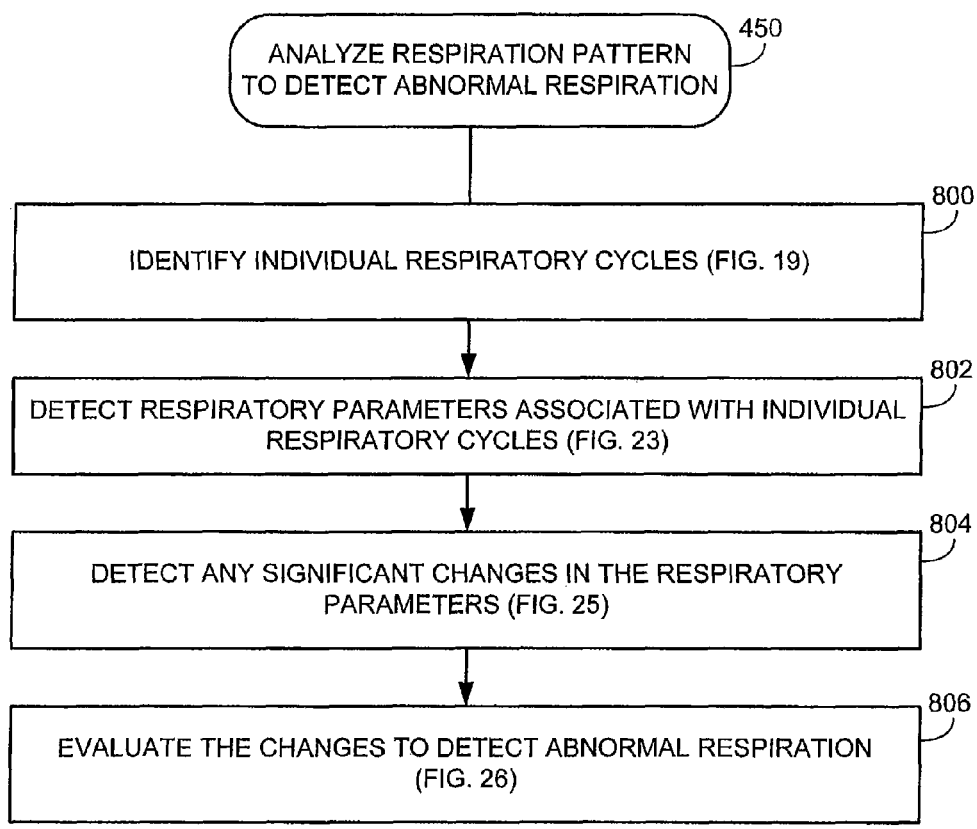
FIG. 18 is a flow chart providing an overview of improved methods for detecting abnormal respiration patterns, which may be performed in furtherance of the techniques of FIG. 14.

An overview of these abnormal respiration detection techniques is set forth in FIG. 18. Initially, at step 800, the pacer/ICD identifies individual respiratory cycles within patient respiration, i.e. the pacer/ICD identifies individual breaths. Specific techniques for identifying individual respiratory cycles are discussed below with respect to FIGS. 19-22. At step 802, the pacer/ICD detects parameters associated with the individual respiratory cycles such as the inter-breath interval, respiration depth, standard deviation of respiration depth, median respiration depth, and respiration power. Specific techniques for detecting such parameters are discussed below with respect to FIGS. 23-24. Next, at step 804, the pacer/ICD detects any significant changes in the parameters associated with the individual respiratory cycles, i.e. the pacer/ICD detects any significant increase or decrease in the parameters. Depending upon the particular respiratory parameters and depending upon the particular form of abnormal respiration, the changes in the respiratory parameters may be abrupt or gradual. Specific techniques for detecting significant changes in respiratory parameters are discussed below with respect to FIG. 25. Finally, at step 806, the pacer/ICD, evaluates the significant changes to detect abnormal respiration. In this regard, normal respiration during sleep is characterized by little or no change in respiratory parameters such as respiration depth (when corrected for patient posture and other non-respiratory factors). Hence, significant changes in respiratory parameters such as respiration depth are indicative of, or associated with, a transition from normal respiration to some form of abnormal respiration. Specific threshold-based techniques for evaluating the changes to detect abnormal respiration are discussed below with respect to FIG. 25. Once abnormal respiration is detected, various techniques may be used to identify the particular form of abnormal respiration, i.e. to distinguish among apnea, hypopnea, hyperpnea, CSR, etc. Exemplary techniques for distinguishing among different forms of abnormal respiration are discussed above in connection with FIG. 14.

Figure 19:
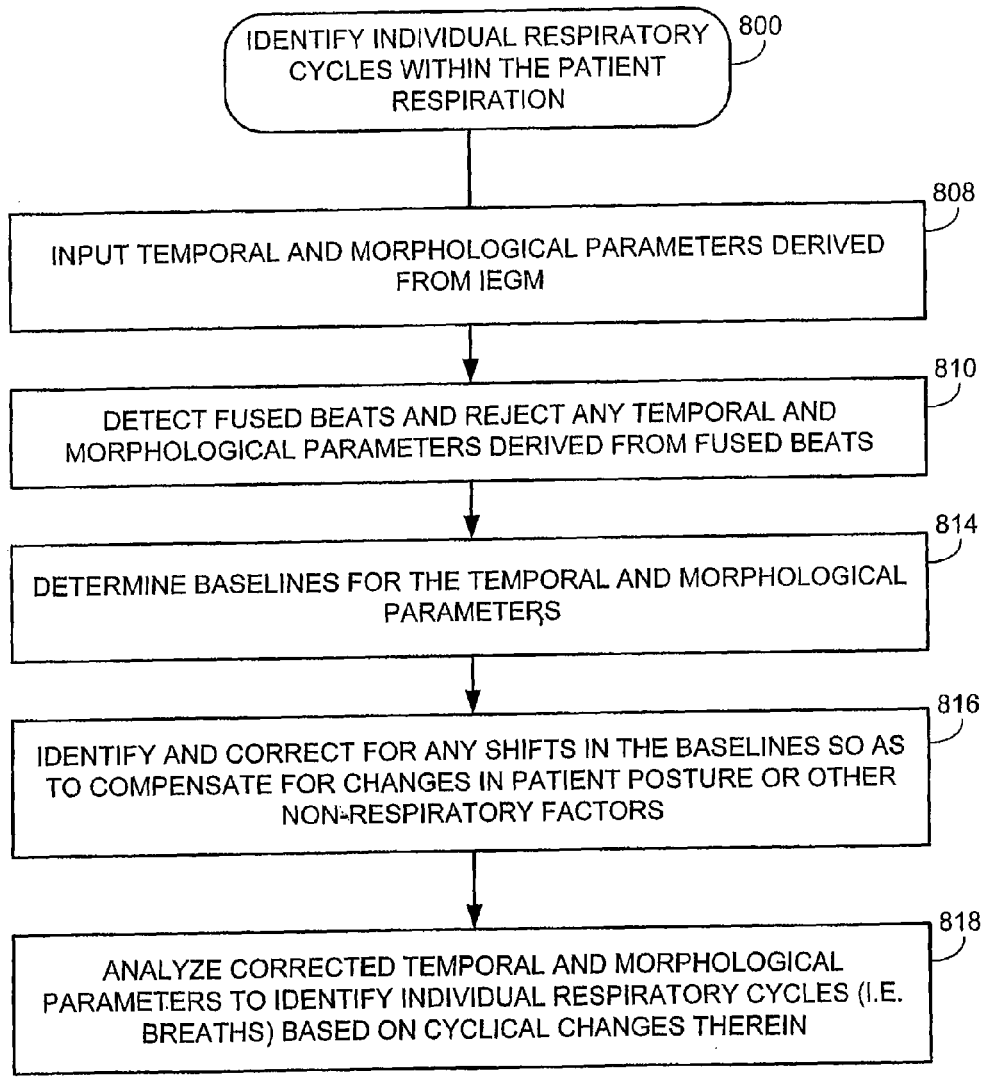
FIG. 19 is a flow chart illustrating exemplary steps directed to identifying individual respiratory cycles in accordance with the technique of FIG. 18.
Figure 20:
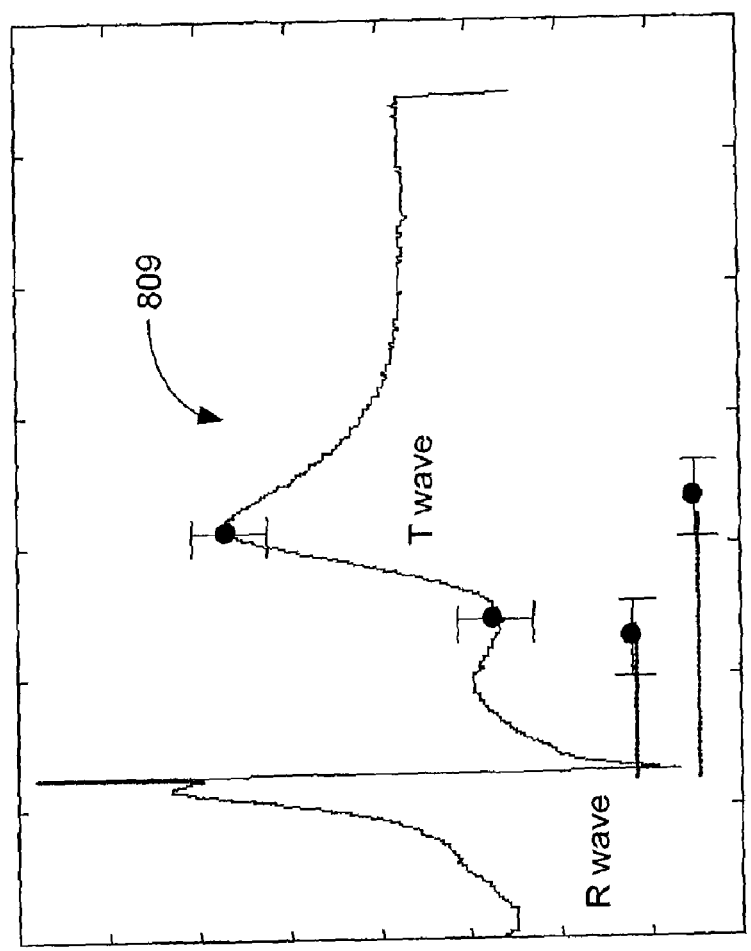
FIG. 20 is a graph illustrating an exemplary cardiac cycle and particularly illustrating historical ranges of values for the T-wave that may used in connection with the techniques of FIG. 19 to extract temporal and morphological parameters.

Turning now to FIGS. 19-20, exemplary techniques for identifying individual respiratory cycles will be described for use at step 800 of FIG. 18. At step 808, the pacer/ICD inputs temporal and morphological parameters derived from the IEGM. This may include, e.g., the maximum amplitude, peak-to-peak amplitude, width and integral of individual features of the IEGM such as the intrinsic atrial depolarization events (P-waves), atrial evoked responses (AER), intrinsic ventricular depolarization events (QRS-complexes), ventricular evoked responses (VER) and premature ventricular events (PVEs). Other exemplary parameters include: the integral of the ventricular post depolarization signal (vPDI), the integral of the atrial post depolarization signal (aPDI), the repolarization integral (tI), a PDI derived from the ventricular far-field post depolarization signal (ffPDI), an integral of the repolarization far-field signal (ffi). Depending upon the signal, it may be appropriate to separately track near-field and far-field signals (particularly with regard to repolarization amplitudes.)

Insofar as temporal parameters are concerned, any of a variety of inter-feature or intra-feature intervals may be tracked, such as, e.g., A-A intervals, AV intervals, R-R intervals, ST intervals, etc. Note that the evaluation of R-R interval is particularly helpful in detecting respiratory sinus arrhythmia (RSA), which is heart rate variability in synchrony with respiration.

It is important to correctly extract morphological and temporal variable from IEGM data to ensure that the variable properly reflects the respiratory modulation. A history of the morphological characteristics can be used to aid in variable extraction. FIG. 20 illustrates an exemplary cardiac cycle 809 including an R-wave (i.e. QRS complex) and a T-wave. Brackets illustrate a historical range of values for T-wave parameters such as T-wave amplitude and ST-interval. Historical ranges such as those illustrated in FIG. 20 may be used by the pacer/ICD to properly identify the parameter to be extract from the IEGM. For example, use of the T-wave amplitude range can be used by the pacer/ICD to correctly extract T-wave amplitude values.

Figure 21:
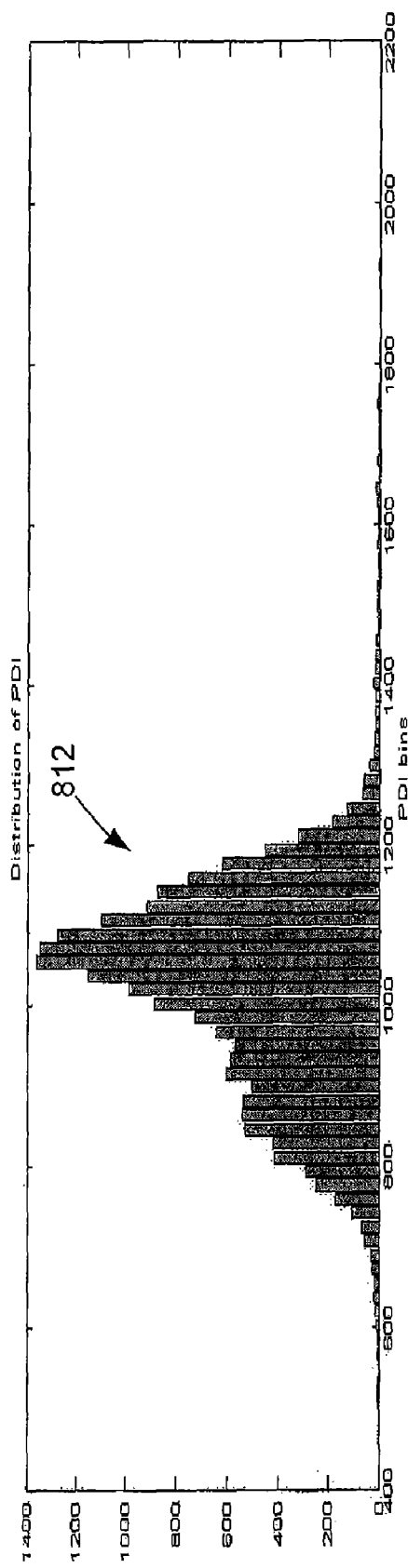
FIG. 21 is a graph illustrating an exemplary distribution of paced depolarization (PDI) values that may be analyzed via the techniques of FIG. 19 to reject fused beats.

At step 810, the pacer/ICD examines the temporal and morphological parameters to detect any fused beats and to reject the parameters derived from fused beats, as these parameters may be anomalous. In one example, various sets of histogram bins are stored in memory and used to track the distribution of parameter values. Each memory bin is associated with a range of values. An exemplary set of bins for use with vPDI is illustrated in FIG. 21. Whenever, a new vPDI value is detected, the pacer/ICD increments the bin corresponding to the new value. The histogram bins thereby quantify the distribution of vPDI values over a period of time. In the specific example of FIG. 21, exemplary vPDI bin values 812 obtained over a six hour period of time are illustrated. (The vertical axis represents bin count. The horizontal axis represents PDI values along an arbitrary scale.) As can be seen, the majority of individual cardiac cycles have vPDI values in the range of 600 and 1200. Any vPDI value that deviates significantly from that range is likely the result of a fused beat and is preferably discarded. Depending upon the implementation, a set of histogram bins such as illustrated in FIG. 21 may be maintained for each temporal and morphological parameter. In other implementations, histogram bins are maintained only for selected cardiac cycle parameters. Otherwise routine experimentation may be employed to identify particular parameters that are advantageously tracked via histogram bins. Preferably, the parameters that are tracked via histogram bins are parameters that are strongly affected by fusion so as to permit fused beat to be readily detected and rejected. Parameters such as vPDI, aPDI, tI, ffPDI, and fftI are typically good candidates. Other techniques for detecting and rejecting fused beats may additionally or alternatively be employed.

At steps 814 and 816 of FIG. 19, the pacer/ICD determines baseline values for the temporal and morphological parameters and corrects for any baseline shifts due to changes in posture. In one example, separate running averages for each of the parameters are tracked. The running average is used as current baseline. Parameters are corrected by subtracting the baseline from the values. Any significant drift in the running average is indicative of a change in posture or other change not due to respiratory variations. Other techniques may be used for detecting changes in posture such as techniques set forth in U.S. patent application Ser. No. 10/329,233, of Koh et al., entitled "System and Method for Determining Patient Posture Based On 3-D Trajectory Using an Implantable Medical Device", filed Dec. 23, 2002. Once a change in posture is detected, a new baseline value is calculated based on a running average of values of the parameter obtained after the change in posture. Preferably, all parameters used in detecting individual respiratory cycles for the purposes of detecting abnormal respiration are corrected for baseline shifts using there or other suitable correction techniques.

At step 818, the pacer/ICD analyzes the corrected temporal and morphological parameters to identify individual respiratory cycles (i.e. breaths) based on cyclical changes therein. As already explained in connection with FIGS. 2-13, the temporal and morphological parameters derived from the IEGM exhibit cyclical variations indicative of respiration. Hence, individual respiratory cycles (i.e. individual breaths) can be detected based on the correct temporal and morphological parameters. Otherwise conventional signal processing techniques may be used to identify cyclical changes in the corrected parameters that are representative of respiration.

Figure 22:
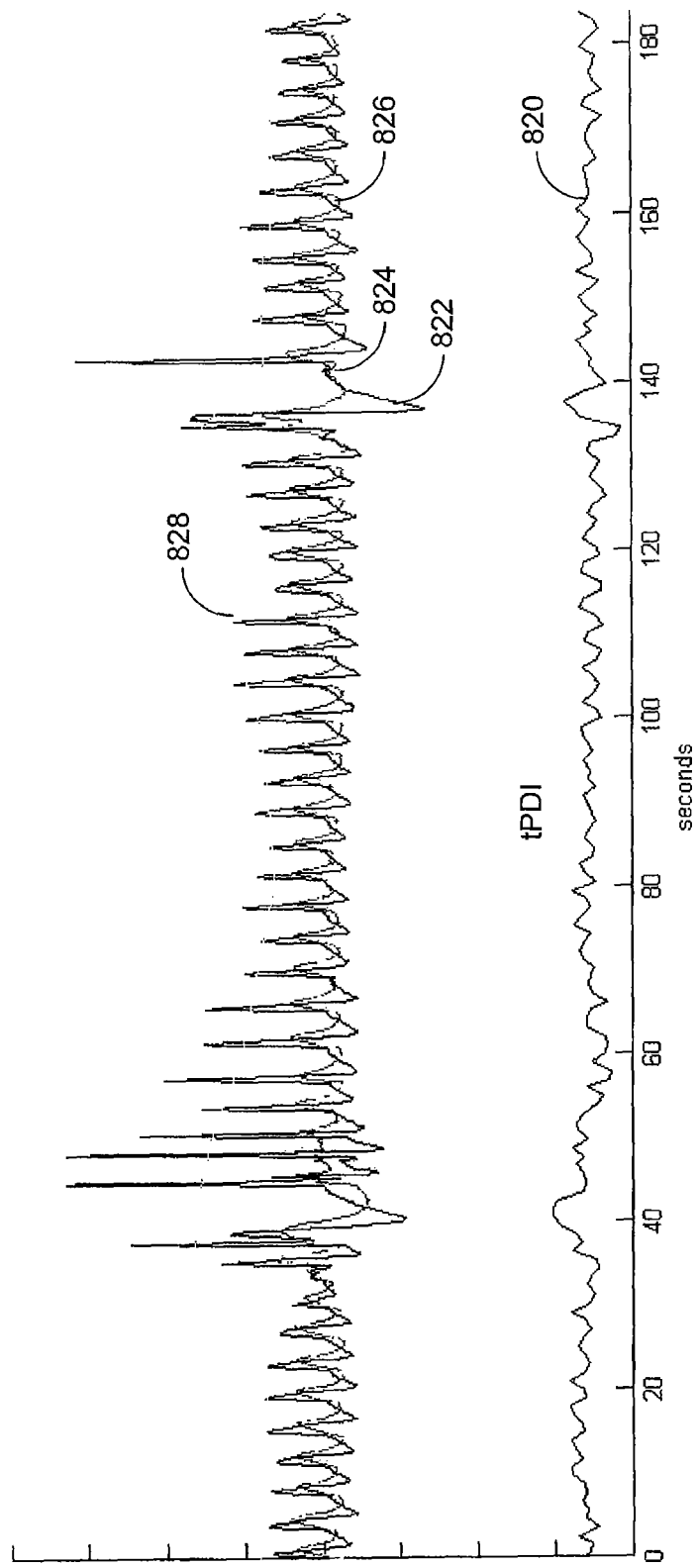
FIG. 22 is a graph illustrating exemplary cardiac cycles and various parameters derived therefrom via the techniques of FIG. 19, along with externally-derived signals representative of patient respiration for comparison.

FIG. 22 illustrates cyclical variations in tPDI (i.e. the paced depolarization integral associated with a T-wave) detected by a pacer/ICD along with externally derived signals representing patient respiration including: nasal flow 822, chest expansion 824, and abdominal expansion 826. As can be seen, the tPDI signal exhibits cyclical variations that are correlated with patient respiration. These cyclical variations are detected to identify the individual respiratory cycles at step 818 of FIG. 19. Note that the particular respiratory pattern shown in FIG. 22 exhibits CSR. The tPDI signal not only permits the individual respiratory cycles to be detected but also permits CSR to be detected, as will be described below with reference to FIGS. 25 and 26. Note also that FIG. 22 additionally illustrates a power value 828 associated with the tPDI signal, which is helpful in detecting abnormal respiration and will also be described below.

Exemplary techniques for detecting respiratory parameters will now be described with respect to FIGS. 23-24. These techniques may be used at step 802 of FIG. 18. At step 830, the pacer/ICD examines the individual respiratory cycles detected via the procedure of FIG. 19 to detect inter-breath intervals, i.e. the interval between peaks of consecutive respiratory cycles. At step 832, the pacer/ICD then integrates the respiration pattern over each individual inter-breath interval to determine depth of respiration for each individual respiratory cycle. The respiratory pattern that is integrated is the signal from which the respiratory cycles were derived and hence can depend on the particular temporal or morphological parameters detected by the device. In the example of FIG. 22, where tPDI is used to detect respiratory cycles, the tPDI signal is integrated over each respiratory cycle found therein. FIG. 24 illustrates an example where a vPDI signal 834 is instead detected during a period of CSR. In that example, the vPDI signal is integrated over each inter-breath interval found therein to obtain a respiration depth signal 835. A single respiration depth value is obtained for each respiratory cycle. Otherwise conventional numerical integration techniques can be employed by the pacer/ICD. For comparison purposes, FIG. 24 also illustrates externally-derived respiratory signals: a chest signal 836, an abdominal signal 838 and a nasal flow signal 840, each tracking the periodic CSR pattern. As can be seen, the respiration depth signal 835 derived by integrating the vPDI signal 834 also exhibits with the CSR cyclical variations found in the externally-derived signals. Accordingly, respiration depth, by itself, can typically be used to detect abnormal respiration. However, to enhance reliability and specificity, the pacer/ICD preferably determines various other respiratory parameters.

Figure 23:
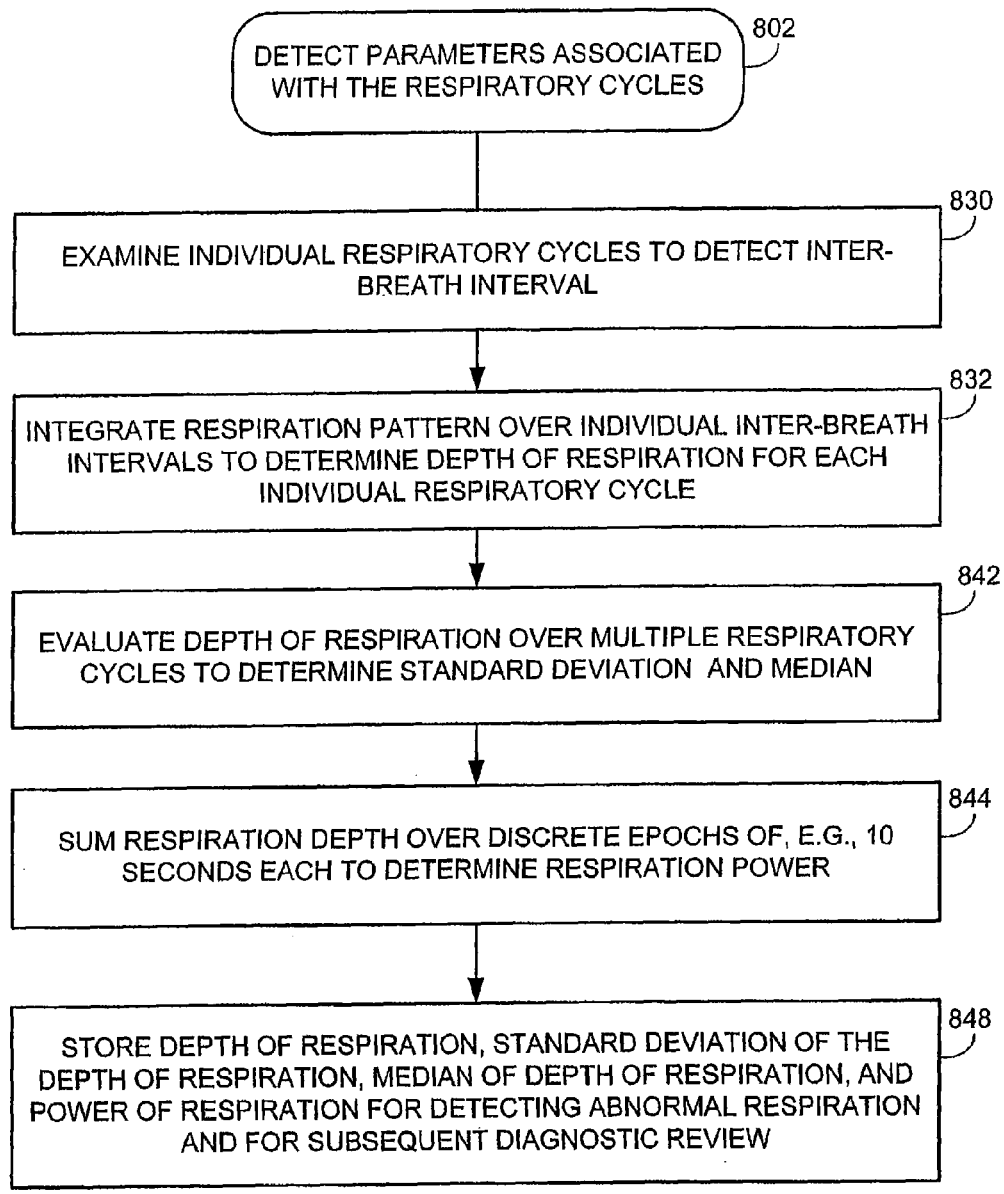
FIG. 23 is a flow chart illustrating exemplary steps directed to deleting parameters associated with individual respiratory cycles in accordance with the technique of FIG. 18.
Figure 24:
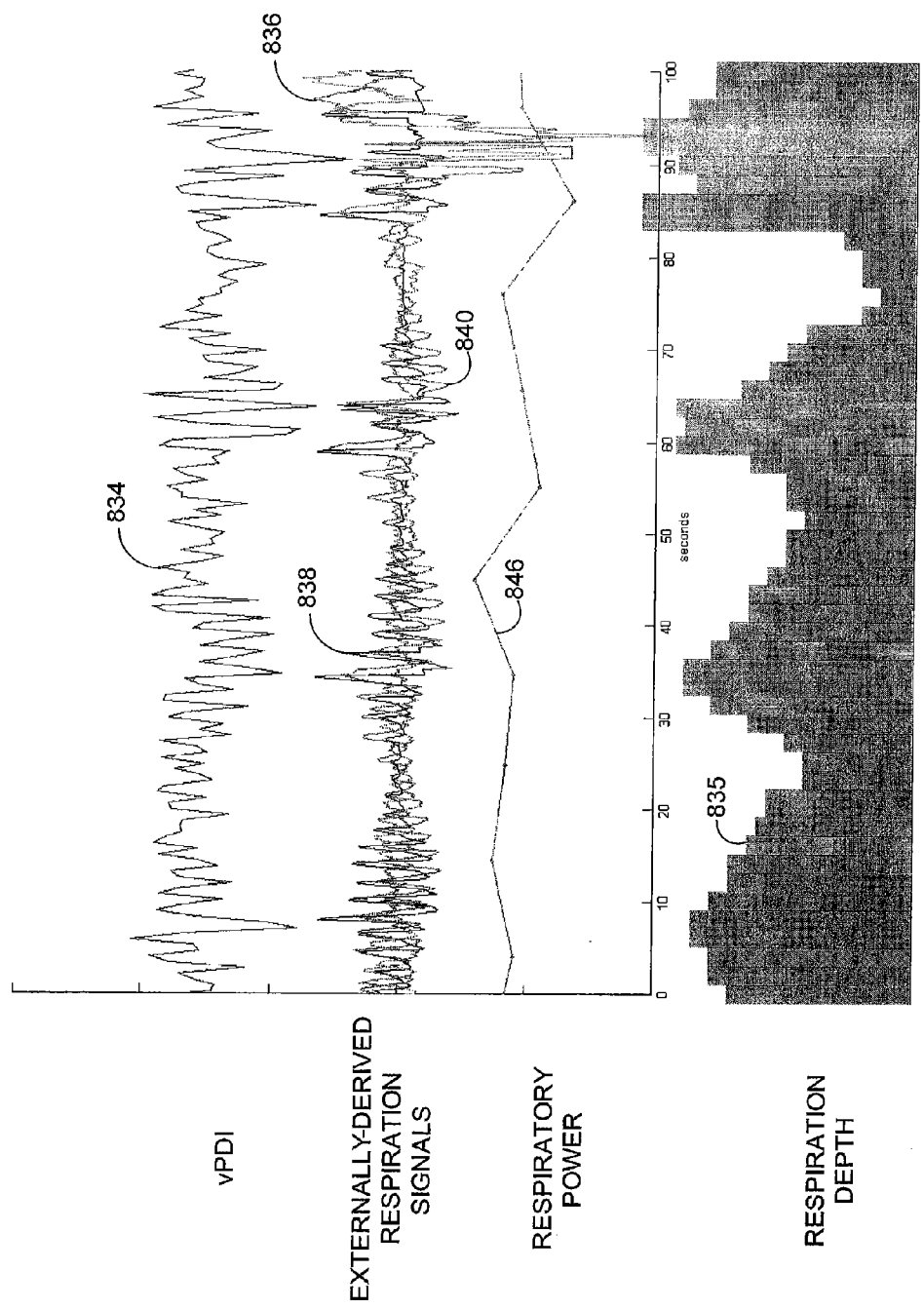
FIG. 24 is a graph illustrating exemplary respiratory cycle parameters that may be analyzed via the techniques of FIG. 19, along with externally-derived signals representative of patient respiration for comparison.

At step 842 of FIG. 23, the pacer/ICD evaluates the depth of respiration over multiple respiratory cycles to determine its standard deviation and median. Otherwise conventional statistical techniques may be employed to evaluate the standard deviation and the median. Other statistical values may additionally or alternatively be evaluated. At step 844, the pacer/ICD determines "respiratory power" by summing respiration depth (835 of FIG. 24) over discrete temporal epochs. The epochs are preferably ten seconds each, but other durations may be used for the epochs such as values in the range of five to fifteen seconds. Hence, in one example, once every ten seconds the pacer/ICD sums the respiration depth values obtained during the previous ten second epoch. An exemplary, resulting respiratory power signal 846 is also shown in FIG. 24. It too exhibits cyclical variations indicative of CSR. Note, however, because the respiratory power is derived based on the preceding ten seconds of respiratory depth signals, its cyclical variations tend to lag those exhibited in the respiration depth signal. At step 848, the pacer/ICD stores the various values it has calculated: depth of respiration, standard deviation of the depth of respiration, median of depth of respiration, and power of respiration for use in detecting abnormal respiration and for subsequent diagnostic review. In addition to calculating a power value from the respiration depth, the pacer/ICD can also calculate a power value associated with each of the temporal and morphological parameters (such as aPDI, vPDI, etc.) by integrating these parameters over the last ten second epoch. (This is discussed further with reference to FIG. 27.) The additional power values may be combined with the respiration power to provide a more robust power value for use in abnormal respiration detection.

Figure 25:
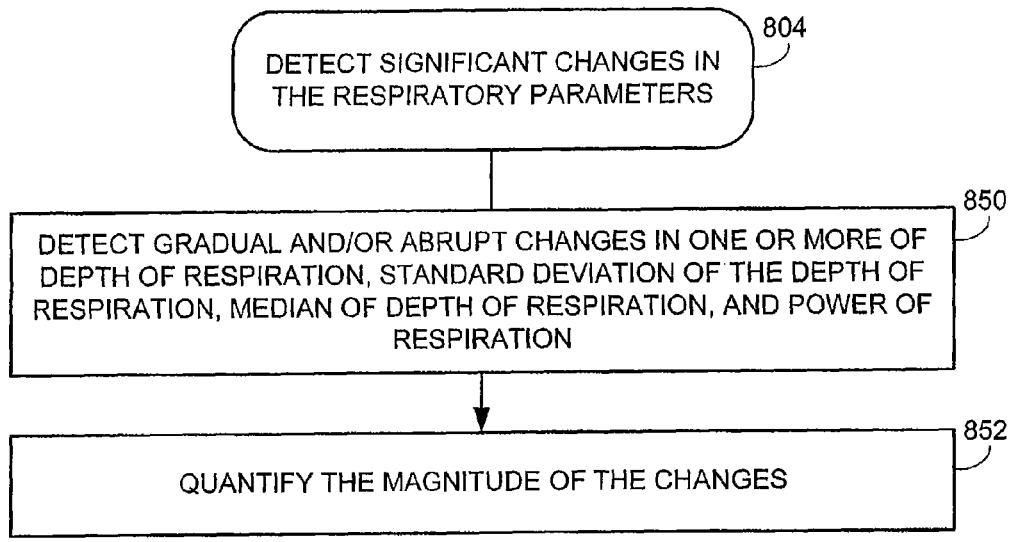
FIG. 25 is a flow chart illustrating exemplary steps directed to detecting significant changes in the respiratory parameters in accordance with the technique of FIG. 18.

Turning now to FIG. 25, exemplary techniques for detecting significant changes in the respiratory parameters will be described for use at step 804 of FIG. 18. At step 850, the pacer/ICD detects gradual and/or abrupt changes in the respiratory parameters, i.e. in one or more of depth of respiration, standard deviation of the depth of respiration, median of depth of respiration, and power of respiration. Otherwise conventional signal processing techniques can be used to detect changes, such as evaluating a time derivative of the signal, which represents a rate of change of the signal with time. The faster the rate of change, the more abrupt the change in the parameter. Depending upon the implementation, it may be desirable to combine two or more respiratory parameters into a signal for evaluation. As noted, however, the respiratory power signal lags the other signals and hence care should be taken if combining the power signal with the other signals. In any case, at step 852, the pacer/ICD quantifies the magnitude of the change. In one example, the magnitude of the change is simply the post-change value of the respiratory parameters (or combination of parameters) minus the pre-change value.

Figure 26:
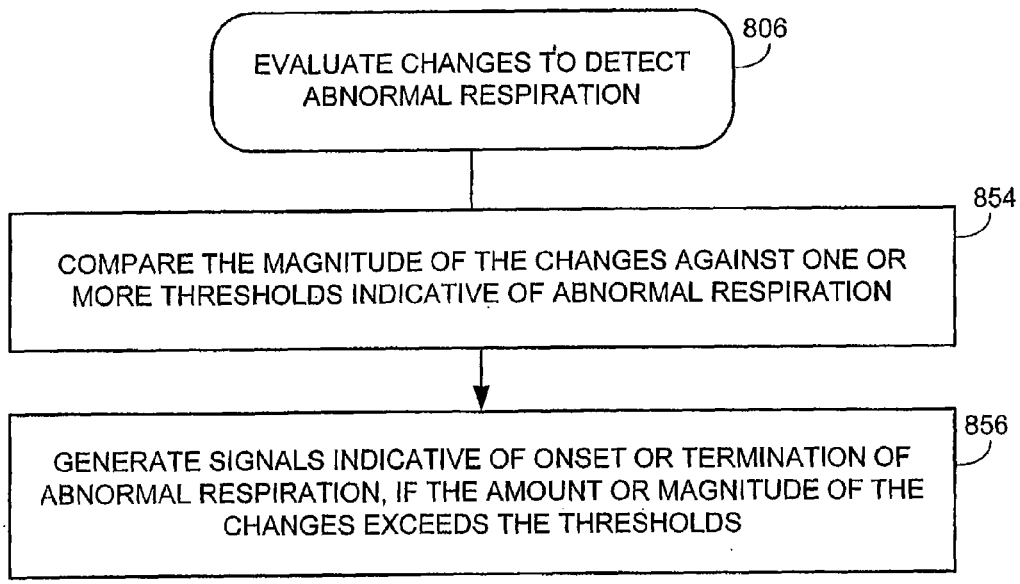
FIG. 26 is a flow chart illustrating exemplary steps directed to evaluating the significant changes to detect abnormal respiration in accordance with the technique of FIG. 18.

FIG. 26 illustrates a technique for evaluating the changes to the respiratory parameters to detect abnormal respiration for use at step 806 of FIG. 18. Ate step 854, the pacer/ICD compares the magnitude of the changes against one or more thresholds indicative of abnormal respiration. For example, if the respiratory parameter being tracked is the depth of respiration, the magnitude of any abrupt change in respiration depth is compared against a predetermined threshold indicative of abnormal respiration. The thresholds depend on the particular parameter being tracked and may further vary from patient to patient. Suitable threshold values may be specified following implant of device based on the specific characteristics of patient in which the device is implanted and/or may be automatically updated during routine working of the algorithm. The direction of the change is also preferably analyzed to determine whether an episode of abnormal respiration is beginning or ending. For example, a sudden drop in respiration depth from a previously normal depth is indicative of the onset of apnea/hypopnea. A sudden increase in respiration depth from a previously abnormally low respiration depth is instead indicative of a return to normal respiration. A still further abrupt increase may be indicative of the onset of hyperpnea. At step 856, the pacer/ICD then generates signals indicative of onset or termination of abnormal respiration. The signals may be used to trigger warning signals or to control therapy, as already described above with reference to FIG. 14. Also, as has already been explained in connection with FIG. 14, the pacer/ICD preferably identifies the particular form of abnormal respiration so as to permit the appropriate therapy and/or warnings to be delivered.

Figure 27:
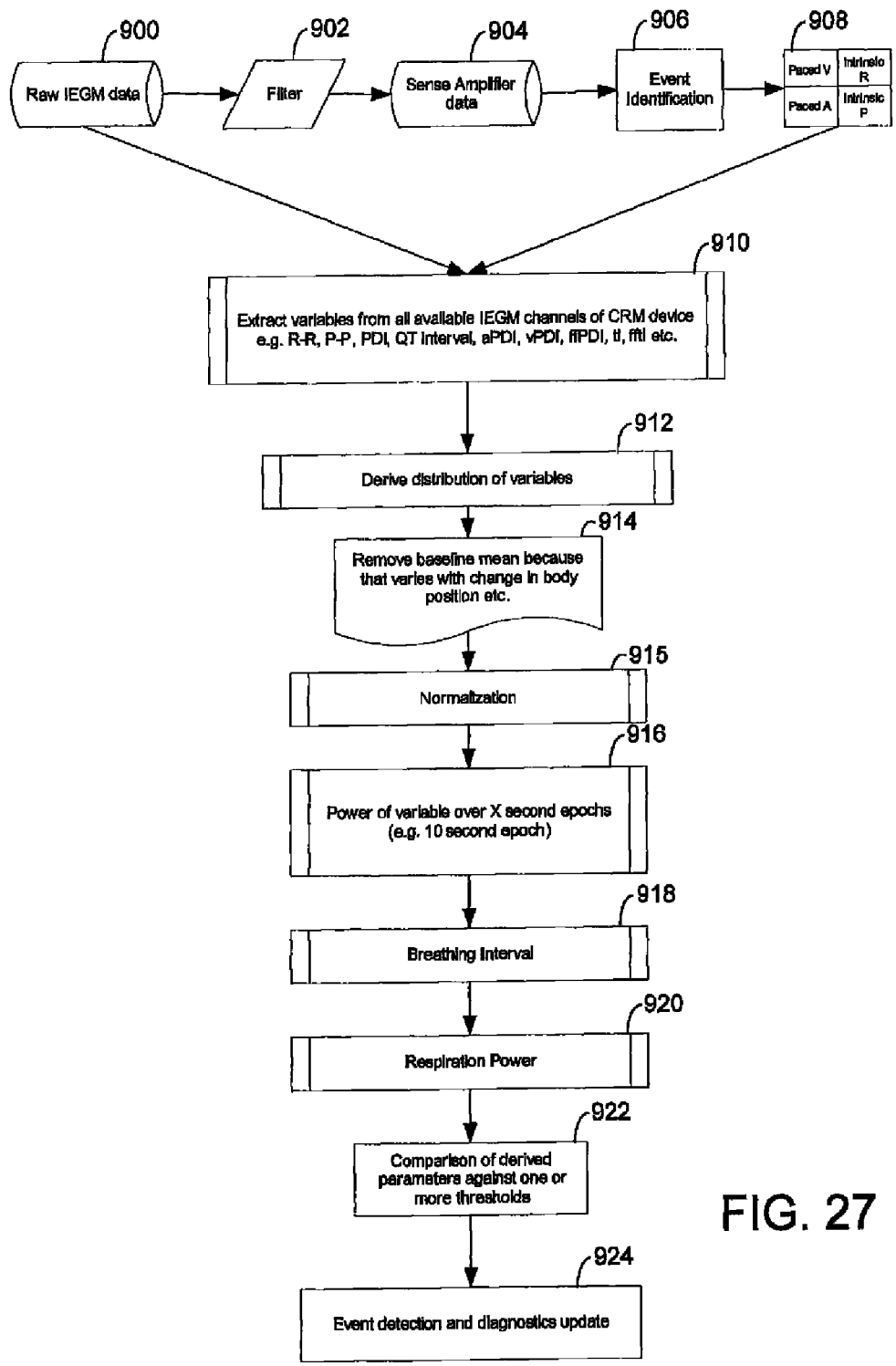
FIG. 27 is a flow chart summarizing the overall abnormal respiration detection procedures of FIGS. 18-26.

FIG. 27 further illustrates and summarizes the components and method steps employed to implement the technique of FIGS. 18-26. As will be explained, the technique of FIG. 27 includes some additional features as well. Briefly, raw IEGM data 900 is filtered via sense amplifiers 902 to yield sense amplifier data 904. The sense amplifier data is analyzed via an event identification block 906 to identify and extract individual events 908, such as paced atrial or ventricular events and intrinsic (i.e. sensed) atrial and ventricular events. These steps/components are conventional. Then, the raw IEGM data and the events found therein are processed at block 910 to extract variables for the purposes of abnormal respiration detection. That is, data and signal from all available IEGM channels of cardiac rhythm management (CRM) device, i.e. the pacer/CD, are extracted. Examples include: R-R, P-P, PDI, QT interval, aPDI, vPDI, ffPDI, tl, fftl etc. At block 912, the pacer/CD derives or calculates distributions for the various variables. The histogram techniques described above with reference to FIG. 21 may be employed to derive the distributions. At block 914, the pacer/CD calculates and removes respective baseline means, preferably using techniques described above with reference to steps 814 an 816 of FIG. 19. At block 915, the pacer/ICD preferably normalizes the variables to remove body position-based variability. In one example, a running average of the mean and the standard-deviation are maintained with a window of width equal to 64 beats, i.e. i−64 to i+64. An i+64 scheme is preferable to using an i−128 to i scheme to prevent lag due to such calculation. The IEGM variables are then normalized by eliminating any variation in the calculated mean and standard-deviation. In one specific example, the following formula is used:

$$x'_i = \frac{x_i - \mu}{\sigma} \quad i \in N$$

where □=local mean, and where the local standard deviations are used. In this manner, a moving window normalization is achieved to remove the mean and standard-deviation changes that occur due to body position changes while retaining the relative variations due to respiration.

At block 916, the pacer/CD calculates the power of each variable over a previous epoch of X seconds (e.g. 10 seconds.) This is performed by integrating the variable over the previous epoch of time. These power values are in addition to the respiration power value that is described above with reference to FIG. 23 and provide a further set of values to aid in detecting abnormal respiration. At block 918, the pacer/ICD evaluates the breathing interval, i.e. the inter-breath interval or interval between peaks of consecutive respiratory cycles. Once the breathing interval is calculated, the pacer/ICD can then evaluate respiratory power, which is a sum of respiration depth over the preceding epoch of time where a single respiration depth value is calculated for each individual breathing interval.

At black 922, the pacer/ICD compares the various derived parameters and one or more thresholds, as described above with reference to FIGS. 25 and 26 to detect abnormal respiration. At block 924, individual events (i.e. individual episodes of abnormal respiration) are detected and appropriate diagnostics are stored. Also, as already explained, appropriate therapy may be applied and/or warning signals may be generated.

The techniques of FIGS. 18-27 are advantageously performed while the patient is asleep to detect nocturnal forms of abnormal respiration, but may potentially be performed while awake. (CSR, for example, can occur while a patient is awake, particularly if CHF is severe.) In implementations wherein the techniques are implemented only while the patient is asleep, otherwise conventional sleep detection techniques may be used to detect the onset and termination of sleep. In addition, the sleep detection techniques of the Bornzin et al. and Park et al., patents, cited above, may be used. Additionally, or in the alternative, respiratory parameters detected by the techniques described herein—such as depth of respiration—may be used to detect sleep. In this regard, sleep, compared with wakefulness is associated with reduced lung ventilation mainly due to decreases in tidal volume. Accordingly, detection of persistent low respiration depth can be used alone, or in combination with other techniques, to detect sleep. (A respiration profile incorporating a period of sleep is illustrated in FIG. 15 and described above.)

Also, whereas the techniques of FIGS. 18-27 are advantageously employed in "real time" (based on IEGM signals as they are sensed), the technique can alternatively be employed based on previously recorded parameters. For example, data may be collected overnight then analyzed later to detect episodes of abnormal respiration that have already occurred for the purpose of generate appropriate diagnostic data for physician review.

Physiologic State Detection and Discrimination Techniques

Turning now to FIGS. 28-34, techniques will be described for detecting physiologic states within the patient (such as abnormal respiration). Among other innovations, these techniques operate to distinguish various cardiac rhythm types for the purpose of detecting physiologic states and/or discriminating different physiologic states.

Figure 28:
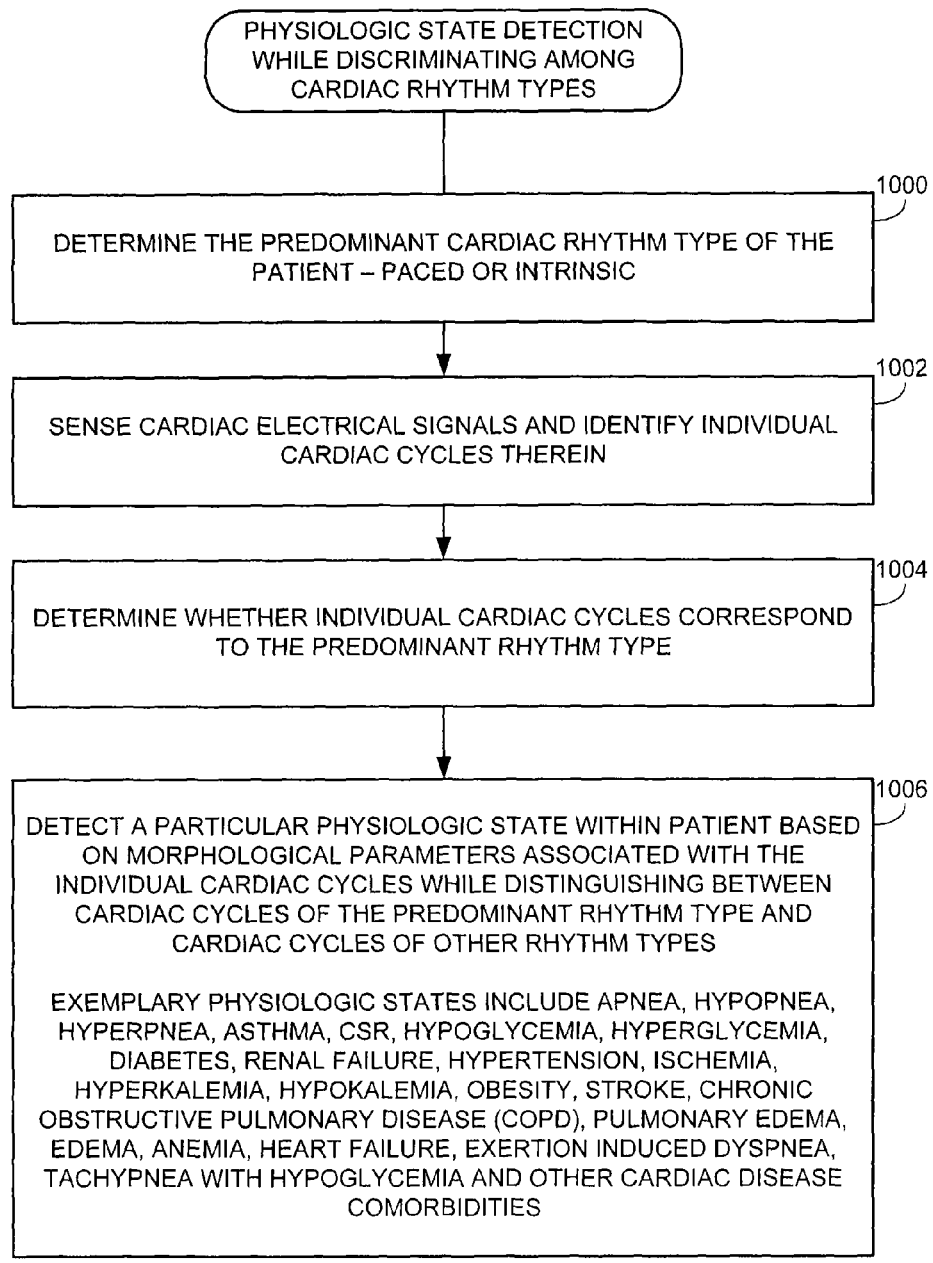
FIG. 28 is a flow chart providing an overview of physiologic state detection techniques that distinguish among various cardiac rhythm types, and which may be implemented by implantable devices such as the pacer/ICD of FIG. 1.

FIG. 28 provides an overview of physiologic state detection techniques employing rhythm-based cardiac cycle discrimination. Beginning at step 1000, the pacer/ICD determines the predominant cardiac rhythm type of the patient. For example, the device determines whether the majority of cardiac cycles (i.e. heartbeats) of the patient are paced or are instead intrinsic. For patients subject to only occasional episodes of bradycardia, the vast majority of cardiac cycles may be intrinsic, and hence the predominant rhythm type is intrinsic. On the other hand, if the patient no longer has a functioning sinus node (perhaps because of ablation or an ischemic attack), then most or all cardiac cycles will be paced, and hence the predominant rhythm type is paced. Also, if the patient is subject to nearly continuous overdrive pacing, then most cycles will be paced. Depending upon the implementation, the pacer/ICD may further distinguish between AR, AV, PR and PV. That is, the pacer/ICD determines which of the four basic cardiac rhythm types is most common in the patient. This can be achieved by tracking the relative numbers of different cardiac rhythm types within the patient, then numerically determining the predominant rhythm type based on relative percentages. Although unlikely, two separate rhythm types may occur with almost identical frequency within at least some patients. In such cases, the pacer/ICD can be programmed to randomly select one of the two rhythm types as the predominant rhythm type. Alternatively, the pacer/ICD may be programmed to suspend its rhythm-based physiologic state detection techniques until a predominant rhythm type emerges within the patient, and to instead use predecessor techniques to detect physiologic states such as the respiration detection techniques described above. Also, the pacer/ICD can normalize for the specific rhythm type, i.e. normalize using mean and standard deviation of each rhythm type.

In one example, step 1000 is performed sometime prior to the point in time when a given physiologic state is to be detected. In one example, the pacer/ICD begins tracking relative percentages of cardiac rhythm types immediately following device implant and then activates its rhythm-based physiologic state detection techniques once a clear predominant rhythm type emerges within the patient. In other examples, the pacer/ICD is programmed to wait until after the post-implant acute phase before tracking the relative percentages of rhythm types. The pacer/ICD can periodically re-determine the predominant rhythm type of the patient so as to account for changes in the predominant rhythm type brought on by, e.g., progression or regression of disease, changes in medications, ischemic attacks, or changes in the programming of the device itself. Also, the device may re-determine the predominant rhythm type of the patient following any major change in the programming of the device, such as following the activation of overdrive pacing or the like. By determining the predominant rhythm type for the patient in advance, real-time or near real-time detection of physiologic states is feasible, at least for some states such as abnormal respiration. Alternatively, the pacer/ICD collects and records IEGM data to be analyzed later. After the IEGM data has been recorded, the pacer/ICD identifies the predominant cardiac rhythm type within the recorded data, then processes the recorded data in accordance with that predominant rhythm type to determine whether the physiologic state of interest occurred during the period of time when the data was recorded. For example, the pacer/ICD can analyze previously recorded IEGM data to determine whether an episode of abnormal respiration occurred within the patient while the IEGM data was being recorded. In the following summary, it is assumed that the predominant rhythm type for the patient is instead determined in advance to permit real-time or near real-time detection.

Once the predominant rhythm type has been determined, step 1002 is performed wherein the pacer/ICD senses IEGM signals (or other appropriate electrical cardiac signals) and identifies individual cardiac cycles therein. (This step is, of course, routinely performed by the pacer/ICD whether or not IEGM-based respiration detection is performed.) At step 1004, the pacer/ICD determines whether or not individual cardiac cycles correspond to the predominant rhythm type. That is, if the predominant rhythm type is paced, the pacer/ICD determines whether each individual heartbeat is paced or not. If the pacer/ICD is programmed to further distinguish between AR, AV, PR and PV heartbeats, and the predominant rhythm type in the patient is AV, then the pacer/ICD determines whether each individual heartbeat is AV or not. The determination made at step 1004 may be accomplished by examining the appropriate registers within the microprocessor of the device that track this information for routine pacing/sensing purposes. Any cardiac cycle not of the predominant rhythm type is referred to herein as a secondary rhythm type. Hence, in the case where the device distinguishes among the four separate rhythm types (AR, AV, PR and PV), one is predominant, the other three are each "secondary".

At step 1006, the pacer/ICD then detects a physiologic state within the patient such as abnormal respiration based on cycle-to-cycle changes in morphological parameters associated with the individual cardiac cycles while distinguishing between cardiac cycles of the predominant rhythm type and cardiac cycles of other rhythm types. Other physiologic states that may be detected, tracked and discriminated include apnea, hypopnea, hyperpnea, asthma, CSR, hypoglycemia, hyperglycemia, diabetes, renal failure, hypertension, ischemia, hyperkalemia, hypokalemia, obesity, stroke, chronic obstructive pulmonary disease (COPD), pulmonary edema, edema, anemia, heart failure, exertion induced dyspnea, and tachypnea with hypoglycemia. That is, the implantable device is equipped to detect a variety of cardiac disease comorbidities. In this regard, if a patient is a predisposed toward one cardiac disease, the patient is also predisposed to other diseases or conditions, referred to as comorbidities. Pacer/ICDs are usually implanted in response to some form of cardiac ailment or disease. Accordingly, patients with pacer/ICDs are often predisposed to the aforementioned comorbidities and hence it is desirable to detect the physiologic states associated therewith.

For the example wherein respiratory states are detected, the pacer/ICD may use the various morphological parameter-based respiration detection techniques described above (particularly with reference to FIGS. 1-13) to detect and track respiration, but with those techniques modified to distinguish among different cardiac rhythm types. In one particular example, the pacer/ICD simply ignores all cardiac cycles that are not of the predominant type for the purposes of tracking respiration. This is particularly appropriate if almost all cycles are of the predominant type with only a few spurious cycles of other rhythm types. This respiration-based example is illustrated by way of graph 1008 of FIG. 29 wherein spurious cardiac cycles 1010 and 1012 are ignored. In this example, the cardiac cycles of the secondary rhythm type are spurious because they appear as single cardiac cycles amid a longer run of cycles 1014 of the predominant rhythm type. Since these spurious cycles are of a different rhythm type (e.g., AV instead of PR), the morphological parameters representative of the cardiac cycle can differ significantly from the parameters of the cycles of the predominant rhythm type. In this regard, a PDI value derived from a paced beat will likely differ significantly from a PDI value derived from an intrinsic beat. (Integrals derived from intrinsic beats are also referred to herein as PDIs, although they are not necessarily "paced" depolarization integrals.) Note that, of course, some of the difference between the numerical values of the cardiac cycles is due to the cyclical effects of respiration. Nevertheless, as can be seen from the figure, the spurious beats deviate significantly from the respiratory curve tracked by the predominant beats. (This difference is exaggerated within the figure to illustrate the effect. In practice, the numerical difference may be less or more than shown.) By rejecting the spurious beats, a more accurate respiratory curve is obtained, permitting respiratory parameters, such as respiration depth and respiration power, to be more precisely and accurate determined.

Figure 29:
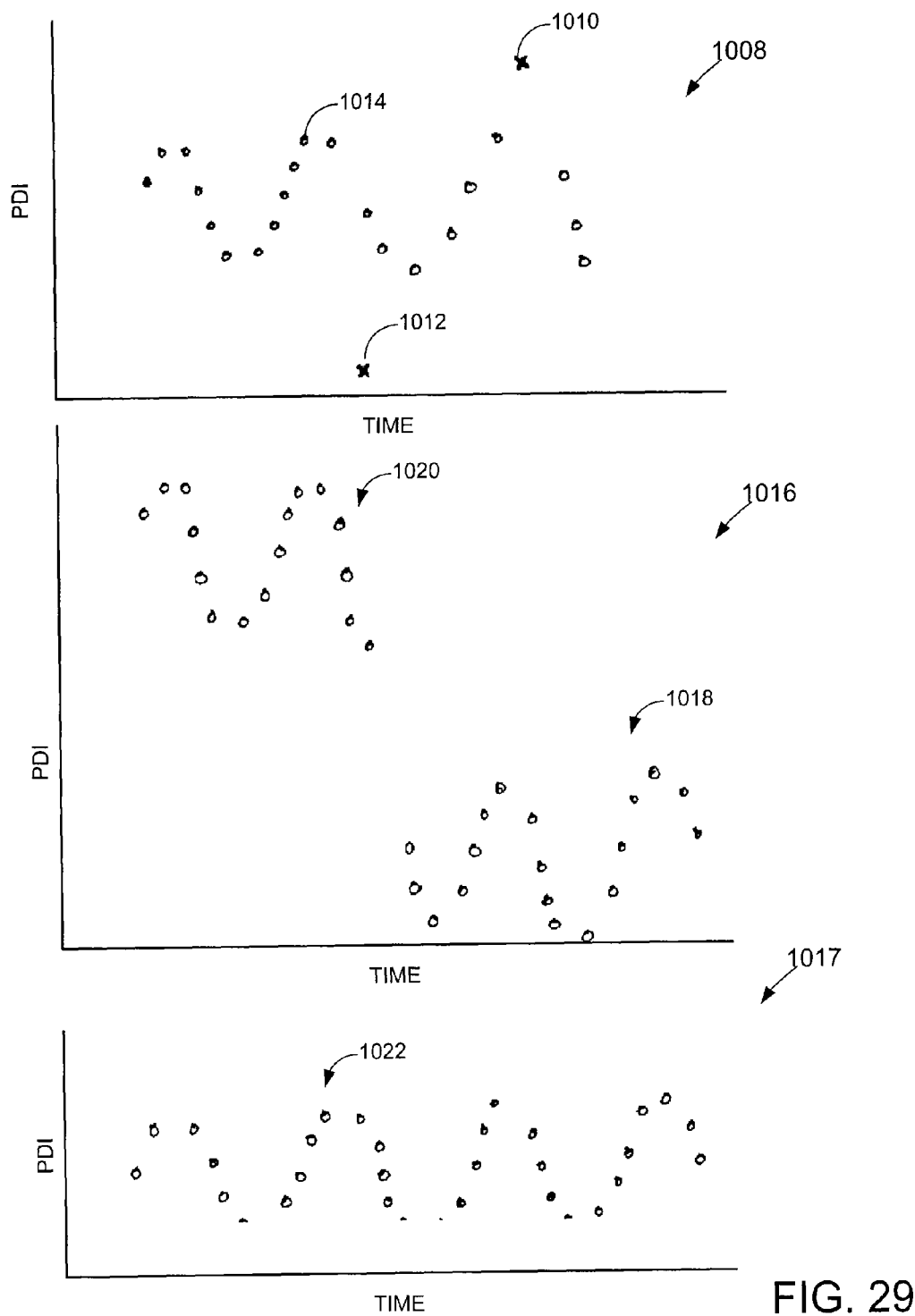
FIG. 29 is a graph illustrating exemplary cardiac cycles that may be analyzed via the techniques of FIG. 28, and particularly illustrating differences between predominant-rhythm and secondary-rhythm cardiac cycles.

In another respiration example, the device renormalizes the morphological parameters of cardiac cycles of secondary rhythms to match the scale of the parameters derived from the cardiac cycles of the predominant rhythm type. This is particularly appropriate if long runs of consecutive cycles of secondary rhythm types occur. This example is illustrated by way of graphs 1016 and 1017 of FIG. 29 wherein PDI values from a consecutive sequence of cycles 1018 of a secondary rhythm type (intrinsic beats) are renormalized based on PDI values derived from cycles 1020 of the predominant rhythm type (paced). The resulting renormalized sequence of cycles 1022 is shown in graph 1017. (Again, differences are exaggerated to illustrate the effect.) As can be seen, the PDI values of the various cardiac cycles now represent a continuous respiratory cyclical variation. Note that, as explained above, the morphological parameters derived from cardiac cycles are preferably initially normalized to remove body position variability. The renormalization of FIG. 29 is an additional step provided to renormalize the secondary cycles to the predominant cycles. This may be achieved, for example, by renormalizing based on mean and standard deviations. In any case, by renormalizing continuous runs of secondary cycles based on the predominant cycles, a more accurate respiratory curve is obtained.

These are just some examples of techniques for distinguishing cardiac cycles of a predominant rhythm type from cardiac cycles of other rhythm types for the purposes of detecting respiration or other physiologic states. As can be appreciated, a variety of techniques may be employed consistent with the general principles described herein, and no attempt is made herein to describe all possible techniques. In some implementations, the techniques for distinguishing cardiac cycles based on rhythm type are applied while discriminating abnormal respiration from normal respiration. Various normal/abnormal respiration discrimination examples will now be described with reference to FIGS. 30-33. It should be understood that these are just examples of the general physiologic state detection and discrimination techniques provided in accordance with the invention.

Figure 30:
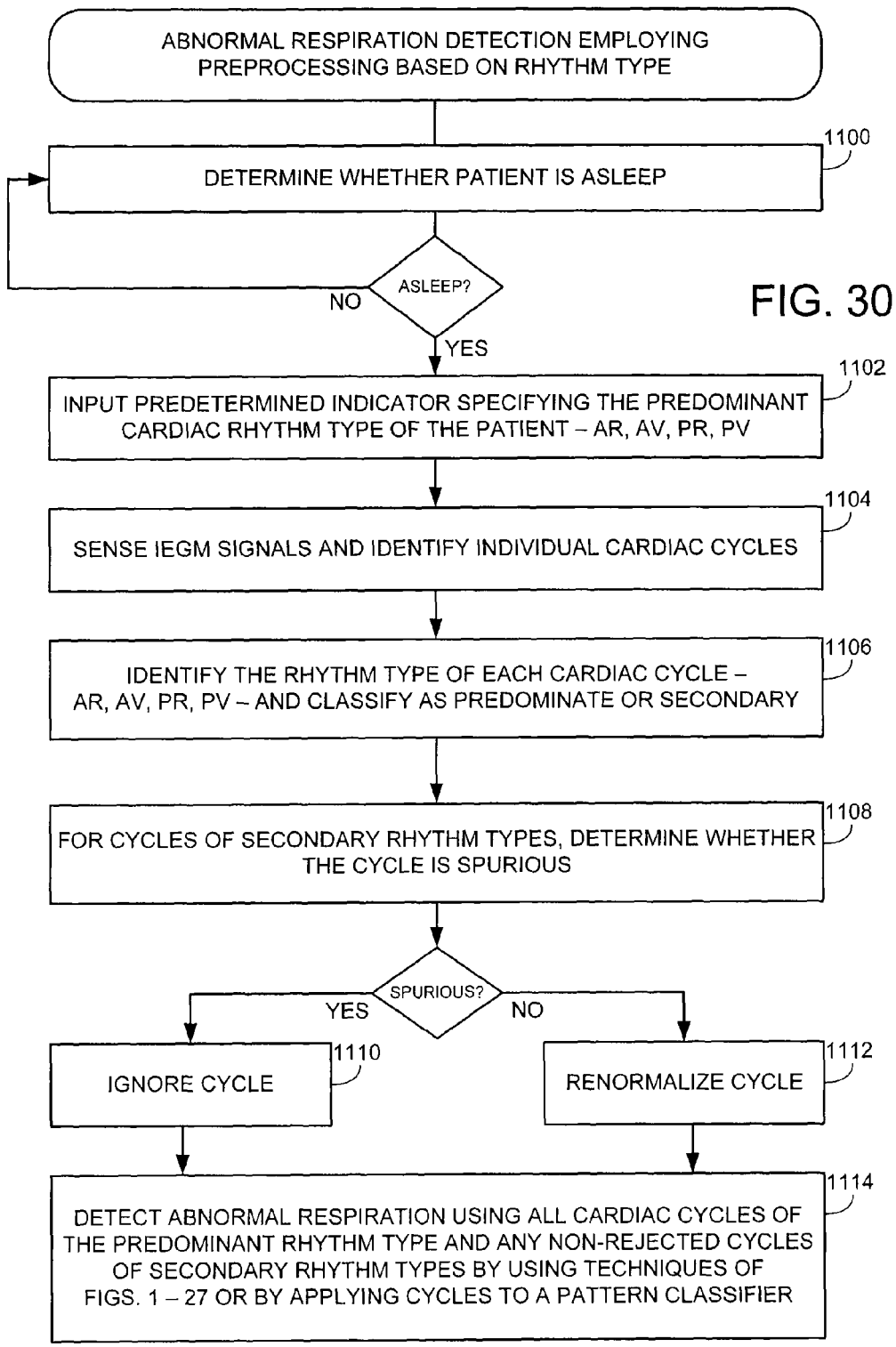
FIG. 30 is a flow chart illustrating a first exemplary technique for detecting abnormal respiration in accordance with the general physiologic state detection technique of FIG. 28, wherein preprocessing of cardiac cycles is performed based on rhythm type.

FIG. 30 illustrates an abnormal respiration detection example wherein cardiac cycles are "preprocessed" based on their rhythm type prior to discriminating normal from abnormal respiration. Beginning at step 1100, the pacer/ICD first determines whether the patient is asleep (and hence subject to sleep apnea or other abnormal respiration disorders occurring during sleep.)

This step need not be performed when detecting forms of abnormal respiration that are not necessarily associated with sleep. Otherwise conventional sleep detection techniques may be used. Assuming the patient is asleep, the pacer/ICD, at step 1102, then inputs an indicator value from memory specifying the predominant cardiac rhythm type of the patient: AR, AV, PR or PV. This indicator value is initially set by the pacer/ICD when it first determines the predominant rhythm type (and whenever the device subsequently re-determines the rhythm type for any reason.) At step 1104, the pacer/ICD senses IEGM signals and identifies individual cardiac cycles. At step 1106, the pacer/ICD identifies the rhythm type of each cardiac cycle: AR, AV, PR or PV. For any cycles of secondary rhythm types (i.e. non-predominant rhythm types), the pacer/ICD, at step 1108, determines whether the cycle is spurious. If spurious, the cycle is ignored, at step 1110, at least for the purposes of abnormal respiration detection. (It is not ignored for the purposes of the routine triggering or inhibiting of pacing pulses.) If the secondary cycle is not spurious, i.e. it is part of run of two or more cycles of the same rhythm type, then the cycle is renormalized, at step 1112, using techniques discussed above.

At step 1114, the pacer/ICD then detects abnormal respiration using all cardiac cycles of the predominant rhythm type and any non-rejected cycles of secondary rhythm types by using techniques of FIGS. 1-27 or by applying cycles to a pattern classifier (such as the pattern classifiers described in the de Chazal et al. patent cited above or in the co-pending patent application filed contemporaneously herewith, which also cited above.) By rejecting spurious secondary cycles and renormalizing all other secondary cycles, the pacer/ICD is capable of more reliably discriminating between abnormal and normal respiratory patterns. Depending upon the particular abnormal recognition technique that is employed, the pacer/ICD may be able to further specify the type of abnormal respiration (i.e. OSA, CSA, or CSR) and/or evaluate its severity.

Although not shown in FIG. 30, the device preferably applies therapy and/or generates warning signals in response to detection of abnormal respiration. Suitable techniques are described above, particularly with reference to FIG. 14. Also, note that, rather than distinguish between single spurious cycles and runs of two more consecutive cycles, the pacer/ICD may instead be programmed to distinguish between a sequence of N or fewer spurious cycles and sequences of N+1 or more consecutive cycles, wherein N is programmable. So, for example, with N=2, the pacer/ICD ignores spurious cycles that appear individually or in pairs, while renormalizing cycles of secondary rhythms that appear in runs of three or more. As can be appreciated, a variety of specific techniques may be employed that discriminate among different runs of secondary rhythm cycles based on the type of cycle and the number of cycles in the run. Also, note that, although the techniques of FIG. 30 are implemented while the patient is asleep, similar techniques may be employed to detect abnormal respiration occurring while a patient is awake (such as any episodes of CSR that might occur within a patient that is awake.)

Figure 31:
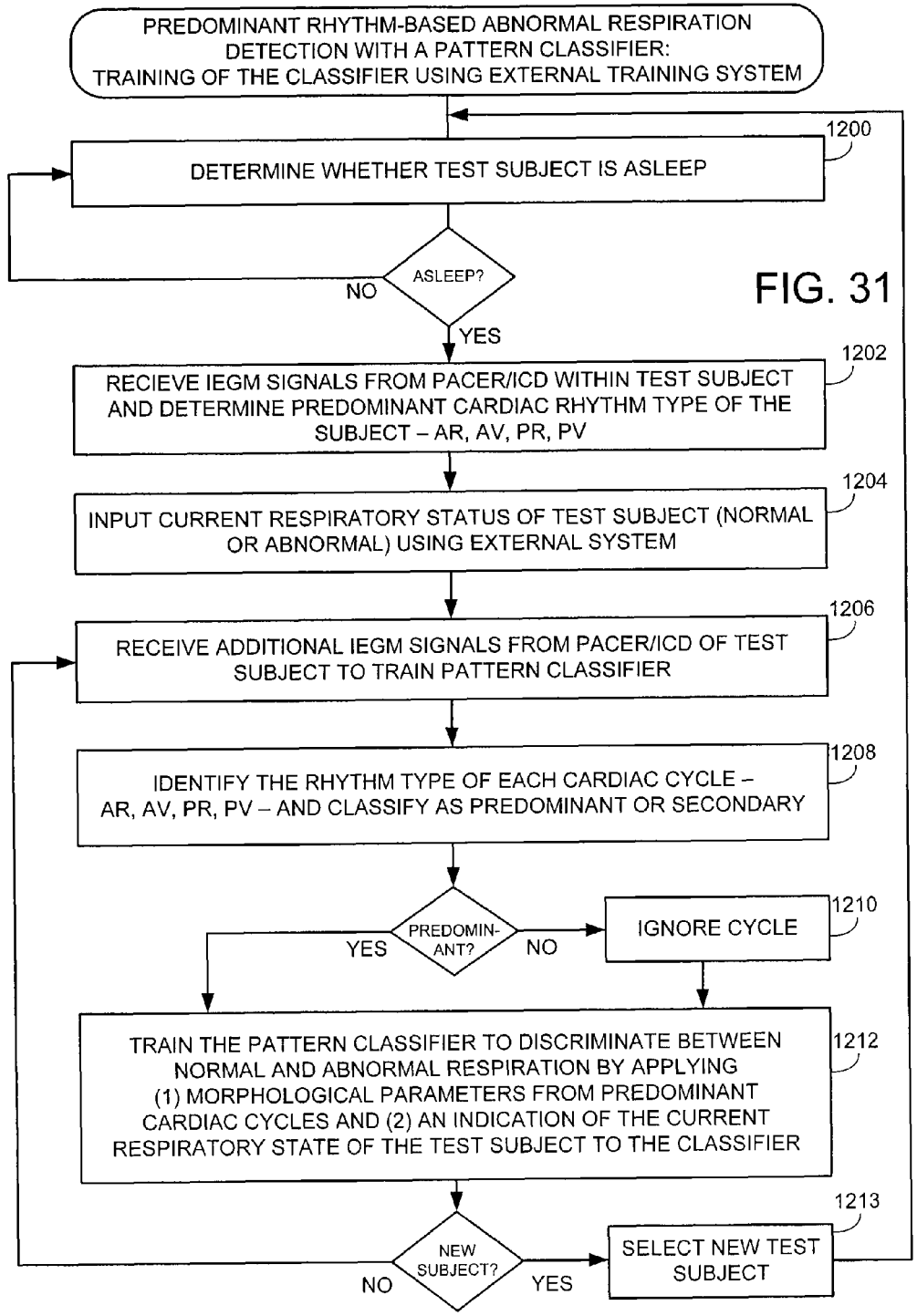
FIG. 31 is a flow chart illustrating a second exemplary technique for detecting abnormal respiration in accordance with the general physiologic state detection technique of FIG. 28, wherein a pattern classifier is trained based only on cardiac cycles of the predominant rhythm type.
Figure 32:
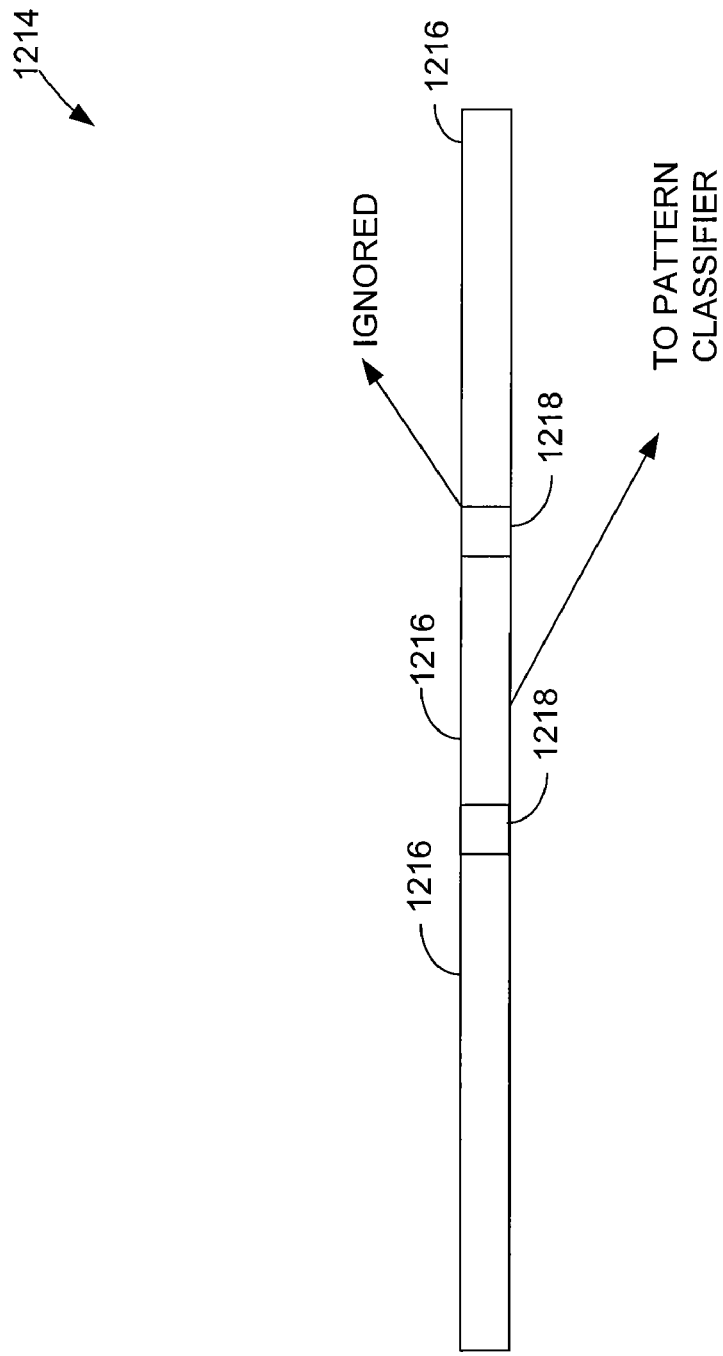
FIG. 32 is a graph illustrating the separate processing of predominant and secondary rhythm types employed during training via the techniques of FIG. 31.
Figure 33:
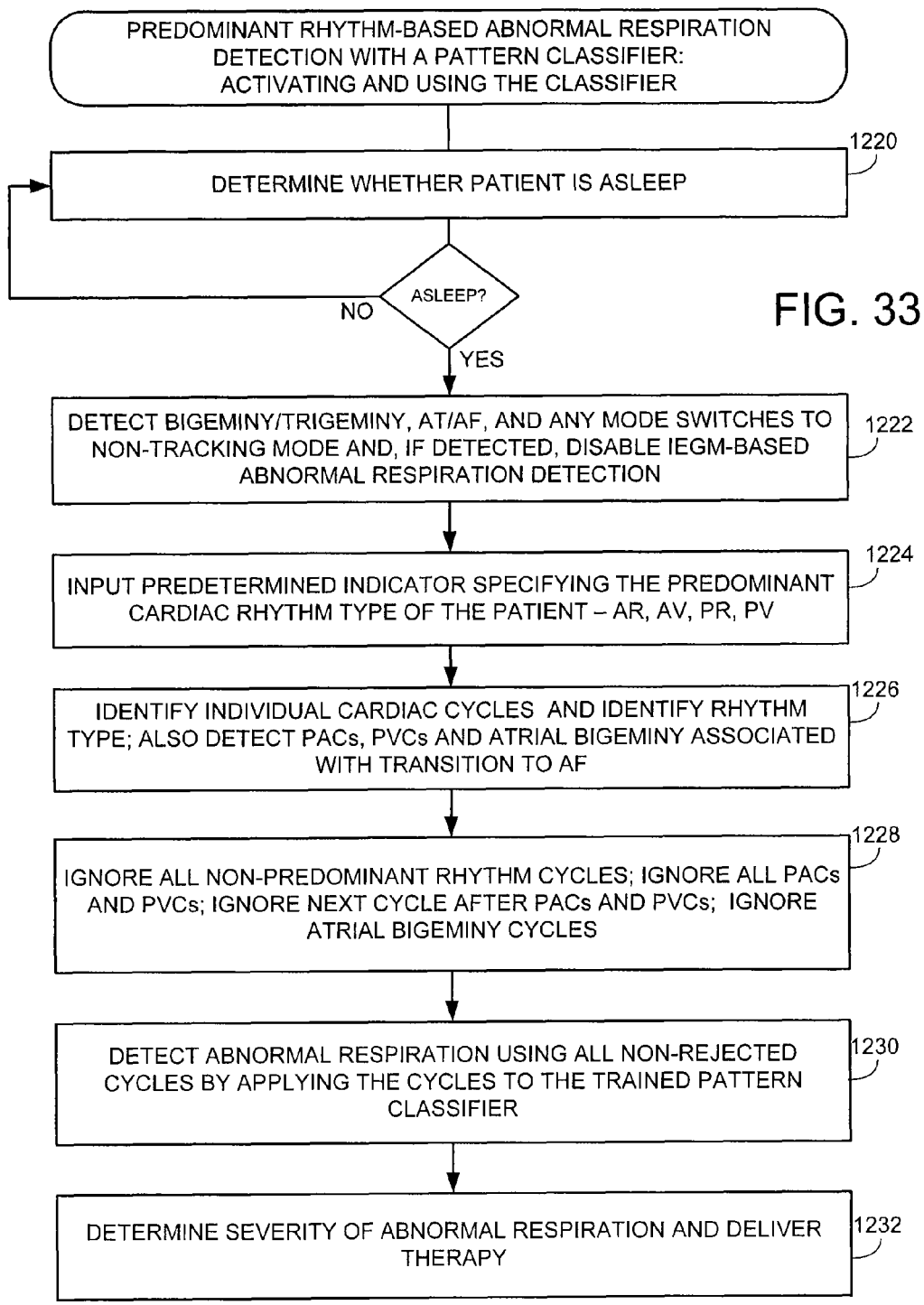
FIG. 33 is a flow chart further illustrating the second exemplary technique of FIG. 28, wherein a previously trained pattern classifier is exploited to discriminate normal and abnormal respiration.

FIGS. 31-33 illustrates an abnormal respiration detection example wherein a pattern classifier or other pattern recognition device is employed that is trained to discriminate normal and abnormal respiration based only on cardiac cycles of the predominant rhythm type. FIGS. 31-32 illustrate the training of the pattern classifier; FIG. 33 illustrates its use. Training is preferably performed prior to device implant. That is, a single pattern classifier is trained in advance using IEGM data collected from a population of test subjects, then individual trained classifiers are installed in various pacer/ICDs for use with individual patients. Alternatively, the pattern classifier of a particular pacer/ICD is trained for the particular patient in whom it is implanted based on IEGM data sensed within that particular patient. The examples of FIGS. 31-33 are directed to implementations where a single classifier is trained in advance based on IEGM data collected from a population of test subjects. As explained in the co-pending application, two general implementations for training and using the pattern classifier are covered. In a first implementation, the pattern classifier is trained to determine whether or not a patient suffers from abnormal physiologic states (such as abnormal respiration.) In a second implementation, the pattern classifier is instead trained to identify individual episodes of abnormal physiologic states, such as individual episodes of apnea. In the following examples, it is assumed that the first implementation is employed, unless indicated otherwise. Beginning at step 1200 of FIG. 31, a training system begins a training session why determining whether a particular test subject is asleep. (In this example, the pattern classifier is only employed to detect abnormal respiration occurring while patients are asleep and so training is only performed based on cardiac cycles detected while the test subjects are also asleep. In other examples, it may not be necessary to wait until the patients and test subjects are asleep.) Assuming the test subject is asleep, the training system, at step 1202, then receives IEGM signals initially sensed within the test subject (by, for example, a conventional pacemaker already implanted therein) and determines the predominant rhythm type of the test subject from the IEGM signals. (This corresponds to step 1000 of FIG. 28. If the predominant rhythm type has already been determined for the particular test subject, the training system merely inputs that information from memory at step 1202.) At step 1204, the training system inputs the respiratory status of the test subject (i.e. whether the test subject generally suffers from abnormal respiration). This is appropriate if the pattern classifier is to be trained to determine whether a patient is subject to abnormal respiration without necessarily detecting individual episodes. The diagnosis of abnormal respiration can be achieved using an otherwise conventional external respiration detection system. (Alternatively, the training system inputs an indication of whether the test subject is currently suffering from an episode of abnormal respiration so it can be trained to specifically detect individual episodes.) At step 1206, the training system then senses additional IEGM signals for use in training the pattern classifier and, at step 1208, identifies the rhythm type of each individual cardiac cycle therein: AR, AV, PR or PV. If a cardiac cycle is not of the predominant type, it is ignored, step 1210. Otherwise, the cardiac cycle is retained for use in training the pattern classifier. That is, at step 1212, the pattern classifier is trained to discriminate between normal and abnormal respiration by applying (1) morphological parameters (such as PDI values) from all predominant cardiac cycles and (2) the indication of the current respiratory state of the test subject to the classifier. Thus, the pattern classifier is trained using only cardiac cycles of the predominant type, while all other cardiac cycles are ignored. This is illustrated within FIG. 32 by way of graph 1214, which shows cardiac cycles 1216 of the predominant rhythm type being sent to a pattern classifier whereas all cardiac cycles of secondary types 1218 are ignored by the pattern classifier.

Although not shown in FIG. 31 or 32, the training system also preferably ignores (for the purposes of training the pattern classifier) any cardiac cycles associated with ventricular bigeminy/trigeminy, AT/AF, and any mode switches to non-tracking modes. (Bigeminy is an arrhythmia wherein abnormal heartbeats occur every other beat and is typically characterized by two beats in rapid succession followed by a pause. Trigeminy is an arrhythmia in which heartbeats occur in groups of threes, usually composed of a sinus beat followed by two extrasystolic beats.) The training system also preferably ignores PACs, PVCs, as well as the next cardiac cycle after PACs and PVCs. The training system also preferably ignores atrial bigeminy cycles associated with a transition to AF. Insofar as AF is concerned, if AF is not found to add a significant confounding component to the Ventricular channel IEGM morphology, then the training system need not exclude the AF data. E.g. If the ventricular pacing and rate is maintained during episodes of AF, and if the respiration component is still visible from the ventricular IEGM morphology metrics, the training system preferably does not exclude data collected during AF.

Once a sufficient amount of data has been processed for a particular test subject, a new test subject is selected, at step 1213, and the training procedure is repeated for the new test subject. Typically, a fairly large number of cardiac cycles from a large number of test subjects—some detected during periods of normal respiration and others detected during abnormal respiration—should be applied to the pattern classifier during the technique of FIG. 31 to train the classifier to properly discriminate between abnormal and normal respiration. Particular pattern classifier training techniques are discussed in the de Chazal et al. patent cited above and in the co-pending patent application filed contemporaneously herewith, also cited above. Eventually, once training is complete (and the classifier has been properly tested to verify its reliability), the classifier is installed within pacer/ICDs for implant within patients so that the pattern classifier may then be employed to detect abnormal respiration within individual patients. That is, the trained classifier parameters are hard-coded into a device for implant. In some implementations, however, the trained classifier parameters are merely used as initial parameters within each individual patient. The particular classifier within a given patient can then be further trained based on IEGM signals detected within that patient or biased based on clinical signals so as to optimize the classifier for that patient. Other aspects of training are discussed in the related application, filed contemporaneously herewith. See, also, U.S. Patent Application 2006/0184056 of de Chazal et al., entitled "Apparatus for Detecting Sleep Apnea using Electrocardiogram Signals."

FIG. 33 illustrates the use of a pattern classifier trained by the techniques of FIG. 31. Within FIG. 33, beginning at step 1220, a pacer/ICD that has a trained pattern classifier installed therein determines whether the patient (in which it has been installed) is asleep to trigger activation of the pattern classifier installed therein to begin discriminating between normal and abnormal respiration. To help ensure reliable detection of abnormal respiration based on IEGM signals, the pacer/ICD also monitors for various cardiac rhythm disorders (or other events) and disables the pattern classifier if such events are detected. In particular, at step 1222, the pacer/ICD detects ventricular bigeminy/trigeminy, AT/AF, and any mode switches to non-tracking modes and, if detected, the pacer/ICD disables IEGM-based abnormal respiration detection using the pattern classifier (subject to the AF considerations discussed above). Preferably, the pattern classifier is reactivated once ventricular bigeminy/trigeminy or the AT/AF has subsided or once the pacer/ICD switches back to a tracking mode. Assuming the pattern classifier is active, step 1224 is then performed wherein the pacer/ICD inputs an indicator specifying the predominant cardiac rhythm type of the patient, assuming the predominant cardiac rhythm type has already been determined.

At step 1226, the pacer/ICD senses IEGM signals, identifies individual cardiac cycles and identifies rhythm type and also detect PACs, PVCs and atrial bigeminy associated with transition to AF. At step 1228, the pacer/ICD ignores (for the purposes of abnormal respiration detection) all cardiac cycles of non-predominant rhythm cycles and also ignores all PACs and PVCs, as well ignoring the next cycle after PACs and PVCs, and any atrial bigeminy cycles associated with a transition to AF. At step 1230, the pacer/ICD then detects abnormal respiration (if occurring within the patient) by applying all non-rejected cardiac cycles to the pattern classifier trained via the technique of FIG. 31. At step 1232, the pacer/ICD then determines the severity of the abnormal respiration and delivers appropriate therapy, generates warning signals, and/or records diagnostic information. The severity of the abnormal respiration may be ascertained using otherwise conventional techniques, such as by determining the duration of each period of apnea. The co-pending patent application filed contemporaneously herewith discusses techniques wherein the pattern classifier itself determines severity.

Thus, FIG. 33 illustrates an abnormal respiration detection example employing a pattern classifier specifically trained to recognize abnormal respiration and wherein all cardiac cycles of secondary rhythm types are ignored (along with various other cycles such as PACs and PVCs). In other examples, the pattern classifier may instead be trained in accordance with the technique of FIGS. 29-30, wherein spurious secondary beats are ignored but whereas continuous runs of secondary beats are normalized prior to training. As can be appreciated, a variety of training/usage techniques may be employed in accordance with the principles of the invention. To detect other physiologic states and/or comorbidities, a pattern classifier is specifically trained in advance using IEGM data derived from test subjects having those physiologic states/comorbidities. To detect a plurality of physiologic states, a set of pattern classifiers may be installed within the pacer/ICD, with each classifier separately trained to recognize a particular physiologic state. In other words, various pattern classifiers may be provided, each trained to recognize one or more of: apnea, hypopnea, hyperpnea, asthma, CSR, hypoglycemia, hyperglycemia, diabetes, renal failure, hypertension, ischemia, hyperkalemia, hypokalemia, obesity, stroke, chronic obstructive pulmonary disease (COPD), pulmonary edema, edema, anemia, heart failure, exertion induced dyspnea, and tachypnea with hypoglycemia based on IEGM signals derived from test subjects.

Although the training techniques described herein employ an external training system, training may instead be performed within the pacer/ICD, if so equipped. In other words, the pacer/ICD may be provided with a pattern classifier not yet trained (or only partially trained). Following device implant, the pacer/ICD then trains its pattern classifier using IEGM signals sensed by the pacer/ICD along with signals from another (non-pattern recognition-based) apnea detector. Examples of non-pattern recognition-based apnea detectors are described in U.S. patent application Ser. Nos. 10/883,857 and 10/821,241 cited above.

The various detection and discrimination techniques of FIGS. 28-30 and 33 may be implemented within any appropriate implantable medical device. In some implementations, the techniques are performed substantially in real-time to promptly detect episodes of abnormal respiration or other physiological states. However, as noted, the techniques may instead be applied to stored IEGM data to detect episodes of abnormal respiration (or other physiological states) that have already occurred within the patient. Moreover, principles of the invention are also applicable to external devices when used in conjunction with implanted devices. For example, an external programmer device may be equipped to detect physiological states within a patient based on IEGM data sensed by a device implanted within the patient and sent via telemetry to the programmer for processing.

Figure 34:
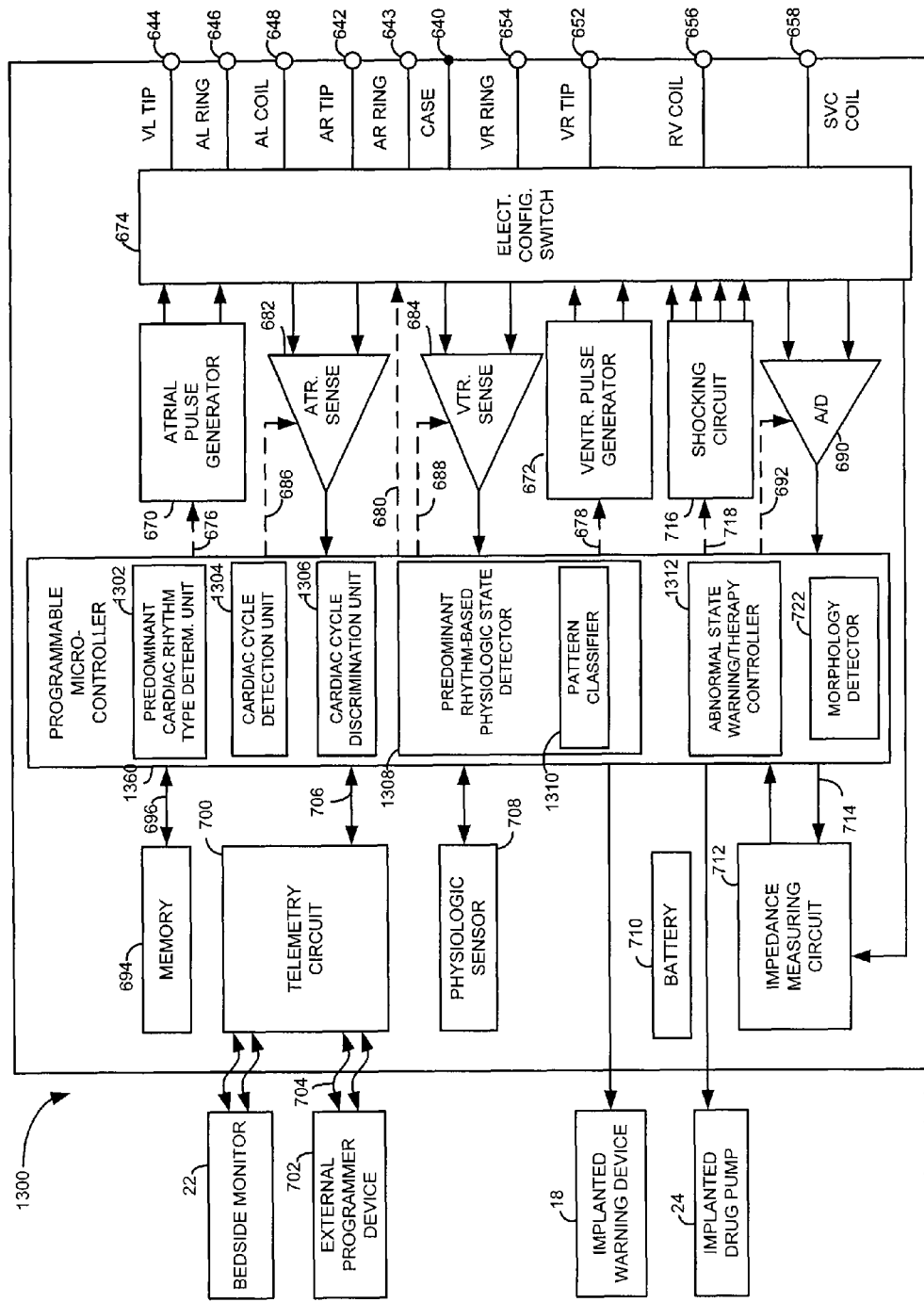
FIG. 34 is a functional block diagram of an alternative implementation of the pacer/ICD of FIG. 16, illustrating basic circuit elements that provide cardioversion, defibrillation and/or pacing stimulation in four chambers of the heart and particularly illustrating predominant cardiac rhythm-based components for detecting and discriminating physiologic states within the patient.

For the sake of completeness, an exemplary pacer/ICD employing components for implementing the techniques of FIGS. 28-30 and 33 is illustrated in FIG. 34. Most of the components of the pacer/ICD of FIG. 34 are the same as that of FIG. 17 and will not be re-described. Only pertinent differences will be discussed. Pacer/ICD 1300 of FIG. 34 includes a microcontroller 1360, which incorporates a predominant cardiac rhythm type determination unit 1302 operative to determine a predominant cardiac rhythm type of the patient; a cardiac cycle detection unit 1304 operative to sense cardiac electrical signals and identify individual cardiac cycles therein; a cardiac cycle discrimination unit 1306 operative to determine whether individual cardiac cycles correspond to the predominant rhythm type; a predominant rhythm-based physiologic state detector 1308 operative to detect a physiologic state within the patient based morphological parameters associated with the individual cardiac cycles while distinguishing between cardiac cycles of the predominant rhythm type and cardiac cycles of other rhythm types (as summarized in FIG. 28). The physiologic state detector 1308 may include a pattern classifier 1310 or other pattern recognition device (as summarized in FIGS. 31-32).

An abnormal state warning/therapy controller 1312 is provided to generate warning signals and/or control therapy in response to detection of an abnormal physiologic state, such as abnormal respiration. Specific forms of therapy to apply in response to abnormal respiration are discussed above. Insofar as the other comorbidities discussed herein are concerned, otherwise conventional therapies may be applied, if the pacer/ICD is so equipped. If the pacer/ICD is not equipped to deliver therapy for particular comorbidities, warning signals and/or diagnostic data is instead preferably generated.

These microcontroller components are preferably provided in addition to the various microcontroller components shown in FIG. 17, which are not repeated within FIG. 34. Components 1306, 1308, 1310 and 1312 may alternatively be implemented within external programmer 702 and/or bedside monitor 22 for detecting respiration and discriminating normal respiration from abnormal respiration within the patient based on data detected within the patient and transmitted via telemetry circuit 700.

What have been described are various systems and methods for tracking respiration, detecting episodes of abnormal respiration and delivering therapy in response thereto using an implantable system controlled by a pacer or ICD. However, principles of the invention may be exploiting using other implantable systems or in accordance with other techniques. Thus, while the invention has been described with reference to particular exemplary embodiments, modifications can be made thereto without departing from the scope of the invention.

What is claimed is:

1. A method for detecting physiologic states within a patient using an implantable medical device, the method comprising:
   determining a predominant cardiac rhythm type of the patient;
   determining a secondary cardiac rhythm type of the patient, the secondary rhythm type differing from the predominant rhythm type;
   sensing cardiac electrical signals via one or more electrodes coupled to a detector incorporated into a housing of the implantable medical device and identifying individual cardiac cycles therein using a predominant cardiac rhythm type determination unit incorporated into a housing of the implantable medical device;
   determining whether individual cardiac cycles correspond to the predominant rhythm type; and
   detecting a physiologic state within the patient based on changes in morphological parameters associated with the individual cardiac cycles while excluding all cardiac cycles of the secondary rhythm type for the purposes of physiologic state detection.

2. The method of claim 1 wherein determining the predominant rhythm type of the patient is performed to determine whether the cardiac cycles of the patient are predominantly paced or intrinsic.

3. The method of claim 1 wherein determining the predominant rhythm type of the patient is performed to determine whether the cardiac cycles of the patient are predominantly one of the following: paced atrial beats with intrinsic ventricular beats (AR); paced atrial beats with paced ventricular beats (AV); intrinsic atrial beats with intrinsic ventricular beats (PR); and intrinsic atrial beats with paced ventricular beats (PV).

4. The method of claim 1
   wherein identifying individual cardiac cycles includes identifying consecutive cycles of the secondary rhythm type; and
   wherein detecting the physiologic state while distinguishing between cardiac cycles of different rhythm types includes renormalizing cardiac cycles of the secondary rhythm type for the purposes of detecting the physiologic state.

5. The method of claim 1 wherein detecting the physiologic state includes detecting one or more of respiration, apnea, hypopnea, hyperpnea, asthma, Cheyne-Stokes Respiration (CSR), hypoglycemia, hyperglycemia, diabetes, renal failure, hypertension, ischemia, hyperkalemia, hypokalemia, obesity, stroke, chronic obstructive pulmonary disease (COPD), pulmonary edema, edema, anemia, heart failure, exertion induced dyspnea, and tachypnea with hypoglycemia.

6. The method of claim 5 wherein detecting respiration includes detecting one or more of a respiration rate, an inter-breath interval, a depth of respiration, a standard deviation of the depth of respiration, and a median of the depth of respiration.

7. The method of claim 5 wherein abnormal respiration is detected based on detected respiration.

8. The method of claim 7 further including evaluating a severity of abnormal respiration.

9. The method of claim 5 wherein detecting apnea is performed only while the patient is asleep.

10. The method of claim 1 further including delivering therapy based on the physiologic state.

11. A method for detecting physiologic states within a patient using an implantable medical device, the method comprising:
    determining a predominant cardiac rhythm type of the patient;
    determining a secondary cardiac rhythm type of the patient, the secondary rhythm type differing from the predominant rhythm type;
    detecting spurious cardiac cycles of the secondary rhythm type;
    sensing cardiac electrical signals via one or more electrodes coupled to a detector incorporated into a housing of the implantable medical device and identifying individual cardiac cycles therein using a predominant cardiac rhythm type determination unit incorporated into a housing of the implantable medical device;
    determining whether individual cardiac cycles correspond to the predominant rhythm type; and
    detecting a physiologic state within the patient based on changes in morphological parameters associated with the individual cardiac cycles while excluding spurious cardiac cycles of the secondary rhythm type for the purposes of respiration detection.

12. A method for detecting physiologic states within a patient using an implantable medical device, the method comprising:
    determining a predominant cardiac rhythm type of the patient;
    sensing cardiac electrical signals via one or more electrodes coupled to a detector incorporated into a housing of the implantable medical device and identifying individual cardiac cycles therein using a predominant cardiac rhythm type determination unit incorporated into a housing of the implantable medical device;
    determining whether individual cardiac cycles correspond to the predominant rhythm type;
    detecting abnormal patient respiration based on cycle-to-cycle changes in parameters associated with individual cardiac cycles; and training the device to discriminate between normal and abnormal respiration within the patient based on individual cardiac cycles within the patient, the training step distinguishing between cardiac cycles of the predominant rhythm type and cardiac cycles of other rhythm types.

13. The method of claim 12 wherein training the device includes excluding all cardiac cycles not corresponding to the predominant rhythm of the patient during training.

14. The method of claim 12 wherein the trained device is a component of the implanted device and wherein detecting abnormal respiration using the trained device is performed by the implanted device.

15. The method of claim 12 wherein the trained device is a component of a system external to the patient and wherein detecting abnormal respiration using the trained device is performed by the external system based on cardiac signals originally sensed by the implanted device and transmitted to the external system.

16. A system for detecting physiologic states within a patient using an implantable medical device, the system comprising:
    a predominant cardiac rhythm type determination unit operative to determine a predominant cardiac rhythm type of the patient;
    a secondary cardiac rhythm type determination unit operative to determine a secondary cardiac rhythm type of the patient the secondary rhythm type differing from the predominant rhythm type;
    a cardiac cycle detection unit operative to sense cardiac electrical signals and identify individual cardiac cycles therein;
    a cardiac cycle discrimination unit operative to determine whether individual cardiac cycles correspond to the predominant rhythm type; and
    a predominant rhythm-based detector operative to detect a physiologic state within the patient based on morphological parameters associated with the individual cardiac cycles while excluding all cardiac cycles of the secondary rhythm type for the purposes of physiologic state detection.

17. The system of claim 16 wherein the predominant rhythm-based detector includes a respiration detector operative to detect respiration based on cycle-to-cycle changes in morphological parameters associated with the individual cardiac cycles while distinguishing between cardiac cycles of the predominant rhythm type and cardiac cycles of other rhythm types.

18. A system for detecting physiologic states within a patient using an implantable medical device, the system comprising:
    means for sensing cardiac electrical signals and identifying individual cardiac cycles therein;
    means for determining whether individual cardiac cycles correspond to a predetermined predominant rhythm type within the patient;
    means for determining whether individual cardiac cycles correspond to a secondary cardiac rhythm type within the patient, the secondary rhythm type differing from the predominant rhythm type; and
    means for detecting a physiologic state within the patient based on morphological parameters associated with the individual cardiac cycles while excluding all cardiac cycles of the secondary rhythm type for the purposes of physiologic state detection.

* * * * *